United States Patent
Achilefu et al.

(10) Patent No.: US 10,806,804 B2
(45) Date of Patent: Oct. 20, 2020

(54) COMPOUNDS HAVING RD TARGETING MOTIFS AND METHODS OF USE THEREOF

(71) Applicant: Washington University, St. Louis, MO (US)

(72) Inventors: Samuel Achilefu, St. Louis, MO (US); Kexian Liang, St. Louis, MO (US); Rui Tang, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/572,087

(22) PCT Filed: May 5, 2016

(86) PCT No.: PCT/US2016/030893
§ 371 (c)(1),
(2) Date: Nov. 6, 2017

(87) PCT Pub. No.: WO2016/179350
PCT Pub. Date: Nov. 10, 2016

(65) Prior Publication Data
US 2018/0289842 A1   Oct. 11, 2018

Related U.S. Application Data

(60) Provisional application No. 62/157,667, filed on May 6, 2015.

(51) Int. Cl.
| | | |
|---|---|---|
| A61K 51/08 | (2006.01) | |
| A61K 49/00 | (2006.01) | |
| C07K 7/06 | (2006.01) | |
| G01N 33/574 | (2006.01) | |
| A61K 38/00 | (2006.01) | |

(52) U.S. Cl.
CPC ...... *A61K 49/0056* (2013.01); *A61K 49/0032* (2013.01); *A61K 49/0054* (2013.01); *A61K 51/088* (2013.01); *C07K 7/06* (2013.01); *G01N 33/57438* (2013.01); *G01N 33/57492* (2013.01); *A61K 38/00* (2013.01)

(58) Field of Classification Search
CPC .... A61K 49/00; A61K 38/00; A61K 2123/00; A61K 2121/00; A61K 51/08; A61K 51/088; A61K 49/0054; A61K 49/0032; A61K 49/0056; G01N 33/57492; G01N 33/57438; C07K 7/06
USPC .............. 424/1.11, 1.65, 1.69, 9.1, 9.2, 9.6; 530/300; 514/1, 1.1; 534/7, 10–16
See application file for complete search history.

(56) References Cited

U.S. PATENT DOCUMENTS

| | | |
|---|---|---|
| 4,987,021 A | 1/1991 | Kanno et al. |
| 5,107,063 A | 4/1992 | West et al. |
| 5,254,852 A | 10/1993 | Filipovich et al. |
| 5,268,486 A | 12/1993 | Waggoner et al. |
| 5,290,670 A | 3/1994 | Delprato et al. |
| 5,453,505 A | 9/1995 | Lee et al. |
| 5,506,705 A | 4/1996 | Yamamoto et al. |
| 5,508,161 A | 4/1996 | Miyake et al. |
| 5,518,934 A | 5/1996 | Forrest et al. |
| 5,589,250 A | 12/1996 | Asai et al. |
| 5,955,224 A | 9/1999 | Caspar et al. |
| 5,959,705 A | 9/1999 | Fergason |
| 5,972,890 A | 10/1999 | Lees |
| 6,027,709 A | 2/2000 | Little et al. |
| 6,180,085 B1 * | 1/2001 | Achilefu ............ A61K 41/0033 424/1.11 |
| 6,180,086 B1 * | 1/2001 | Achilefu ............ A61K 41/0033 424/1.11 |
| 6,217,848 B1 * | 4/2001 | Achilefu ................ A61K 41/00 424/1.11 |
| 6,272,374 B1 | 8/2001 | Flock et al. |
| 6,358,920 B1 | 3/2002 | Blaschuk |
| 6,395,257 B1 * | 5/2002 | Achilefu ............ A61K 41/0033 424/1.65 |
| 6,487,428 B1 | 11/2002 | Culver et al. |
| 6,491,894 B1 | 12/2002 | Ruoslahti |
| 6,554,444 B2 | 4/2003 | Shimada et al. |
| 6,585,660 B2 | 7/2003 | Dorando et al. |
| 6,610,651 B1 | 8/2003 | Ruoslahti |
| 6,652,835 B1 | 11/2003 | Lauffer et al. |
| 6,663,847 B1 * | 12/2003 | Achilefu .............. C07D 209/08 424/1.11 |

(Continued)

FOREIGN PATENT DOCUMENTS

| | | |
|---|---|---|
| JP | 06-145539 | 5/1994 |
| WO | 1996017628 A1 | 6/1996 |

(Continued)

OTHER PUBLICATIONS

Office Action dated Nov. 7, 2018 from related U.S. Appl. No. 15/090,055; 10 pgs.
Achilefu, S. et al., "Synergistic effects of light-emitting probes and peptides for targeting and monitoring integrin expression," PNAS, May 31, 2005, pp. 7976-7981, vol. 102, No. 22, with Supporting Methods, 17 pgs.
Achilefu, S. et al., "Novel Receptor-Targeted Fluorescent Contrast Agents for In Vivo Tumor Imaging," Invest. Radial., Aug. 2000, pp. 479-485, vol. 35, No. 8, Lippincott Williams & Wilkins, Inc.
Agrapidis-Paloympis, L. et al., "The effect of solvents on the ultraviolet absorbance of sunscreens," J. Soc. Cosmet. Chem., Jul./Aug. 1987, pp. 209-221, vol. 38.

(Continued)

*Primary Examiner* — D. L. Jones
(74) *Attorney, Agent, or Firm* — Global Patent Group, LLC; Dennis Bennett; Clifford Schlecht

(57) ABSTRACT

The present invention provides compounds that have motifs that target the compounds to cells that express integrins. In particular, the compounds have peptides with one or more RD motifs conjugated to an agent selected from an imaging agent and a targeting agent. The compounds may be used to detect, monitor and treat a variety of disorders mediated by integrins.

14 Claims, 21 Drawing Sheets
(15 of 21 Drawing Sheet(s) Filed in Color)
Specification includes a Sequence Listing.

(56) References Cited

U.S. PATENT DOCUMENTS

| | | | |
|---|---|---|---|
| 6,733,744 B1* | 5/2004 | Achilefu | A61K 31/405 424/1.11 |
| 6,747,159 B2 | 6/2004 | Caputo et al. | |
| 6,761,878 B2* | 7/2004 | Achilefu | A61K 41/0057 424/1.11 |
| 6,804,549 B2 | 10/2004 | Hayashi | |
| 6,887,854 B2* | 5/2005 | Achilefu | C07D 209/08 514/27 |
| 6,944,493 B2 | 9/2005 | Alam et al. | |
| 7,128,896 B2* | 10/2006 | Achilefu | A61K 41/0057 424/9.6 |
| 7,134,994 B2 | 11/2006 | Alpert et al. | |
| 7,172,907 B2 | 2/2007 | Chen et al. | |
| 7,175,831 B2* | 2/2007 | Achilefu | A61K 49/0032 424/1.11 |
| 7,201,892 B2* | 4/2007 | Achilefu | A61K 41/0057 424/1.11 |
| 7,211,778 B1 | 5/2007 | Smith et al. | |
| 7,252,815 B2* | 8/2007 | Achilefu | A61K 41/0057 424/1.11 |
| 7,510,700 B2* | 3/2009 | Achilefu | A61K 41/0057 424/1.11 |
| 7,547,721 B1 | 6/2009 | Miwa et al. | |
| 7,556,797 B2* | 7/2009 | Achilefu | A61K 31/405 424/1.11 |
| 7,826,890 B1 | 11/2010 | Winchester, Jr. et al. | |
| 7,850,946 B2* | 12/2010 | Achilefu | A61B 5/0059 424/1.11 |
| 8,053,415 B2* | 11/2011 | Achilefu | A61K 49/0002 424/9.3 |
| 8,199,189 B2 | 6/2012 | Kagenow et al. | |
| 8,318,133 B2* | 11/2012 | Achilefu | A61B 5/0059 424/1.11 |
| 8,344,158 B2* | 1/2013 | Achilefu | C22B 3/02 548/427 |
| 8,498,694 B2 | 7/2013 | McGuire et al. | |
| 8,556,820 B2 | 10/2013 | Alpert et al. | |
| 8,562,537 B2 | 10/2013 | Alpert et al. | |
| 8,586,924 B2 | 11/2013 | Demos | |
| 8,636,659 B2 | 1/2014 | Alpert et al. | |
| 9,687,567 B2 | 6/2017 | Frangioni et al. | |
| 10,230,943 B2 | 3/2019 | Achilefu | |
| 10,652,527 B2 | 5/2020 | Achilefu | |
| 2002/0028474 A1 | 3/2002 | Shibamura et al. | |
| 2002/0030163 A1 | 3/2002 | Zhang | |
| 2002/0041898 A1 | 4/2002 | Linger | |
| 2003/0105299 A1 | 6/2003 | Achilefu et al. | |
| 2004/0014981 A1 | 1/2004 | Lugade et al. | |
| 2004/0087778 A1 | 5/2004 | Feige | |
| 2004/0215081 A1 | 10/2004 | Crane et al. | |
| 2006/0173351 A1 | 8/2006 | Marcotte et al. | |
| 2006/0173360 A1 | 8/2006 | Kalafut et al. | |
| 2007/0042398 A1 | 2/2007 | Peng et al. | |
| 2007/0084985 A1 | 4/2007 | Smith et al. | |
| 2008/0204361 A1 | 8/2008 | Scales et al. | |
| 2009/0028788 A1 | 1/2009 | Achilefu | |
| 2009/0074672 A1* | 3/2009 | Faris | A61K 49/0032 424/9.6 |
| 2009/0093761 A1 | 4/2009 | Sliwa et al. | |
| 2009/0124792 A1 | 5/2009 | Achilefu et al. | |
| 2009/0137908 A1 | 5/2009 | Patwardhan | |
| 2009/0214436 A1 | 8/2009 | Achilefu et al. | |
| 2009/0234225 A1 | 9/2009 | Martin et al. | |
| 2009/0242797 A1 | 10/2009 | Yazdanfar et al. | |
| 2009/0268983 A1 | 10/2009 | Stone et al. | |
| 2010/0110308 A1 | 5/2010 | Nicholson et al. | |
| 2010/0113940 A1 | 5/2010 | Sen et al. | |
| 2010/0215585 A1 | 8/2010 | Frangioni | |
| 2010/0240988 A1 | 9/2010 | Varga et al. | |
| 2010/0323389 A1 | 12/2010 | Xu et al. | |
| 2011/0123450 A1 | 5/2011 | Achilefu et al. | |
| 2011/0213625 A1 | 9/2011 | Joao et al. | |
| 2011/0297815 A1 | 12/2011 | Tian et al. | |
| 2012/0026308 A1 | 2/2012 | Johnson et al. | |
| 2013/0116403 A1 | 5/2013 | Achilefu et al. | |
| 2013/0175430 A1 | 7/2013 | Cunningham et al. | |
| 2013/0317368 A1 | 11/2013 | Warren et al. | |
| 2014/0039309 A1 | 2/2014 | Harris et al. | |
| 2014/0046291 A1 | 2/2014 | Harris et al. | |
| 2014/0121475 A1 | 5/2014 | Alpert et al. | |
| 2014/0152467 A1 | 6/2014 | Spencer et al. | |
| 2014/0155753 A1 | 6/2014 | McGuire, Jr. et al. | |
| 2014/0180032 A1 | 6/2014 | Millett et al. | |
| 2014/0180034 A1 | 6/2014 | Hoseit et al. | |
| 2014/0180056 A1 | 6/2014 | Hoseit | |
| 2014/0180087 A1 | 6/2014 | Millett et al. | |
| 2014/0180135 A1 | 6/2014 | Hoseit et al. | |
| 2014/0180316 A1 | 6/2014 | Hoseit | |
| 2014/0194704 A1 | 7/2014 | Millett et al. | |
| 2014/0200438 A1 | 7/2014 | Millett et al. | |
| 2014/0218210 A1 | 8/2014 | De Jong et al. | |
| 2014/0258743 A1 | 9/2014 | Nool et al. | |
| 2014/0275844 A1 | 9/2014 | Hoseit et al. | |
| 2014/0275950 A1 | 9/2014 | Hoseit | |
| 2014/0276110 A1 | 9/2014 | Hoseit | |
| 2015/0166791 A1 | 2/2015 | Achilefu et al. | |
| 2016/0206758 A1 | 7/2016 | Achilefu et al. | |
| 2016/0347727 A1 | 12/2016 | Frangioni et al. | |
| 2016/0370349 A1 | 12/2016 | Hoppin et al. | |

FOREIGN PATENT DOCUMENTS

| | | |
|---|---|---|
| WO | 1998022146 A2 | 5/1998 |
| WO | 1998048838 A1 | 11/1998 |
| WO | 1998048846 A1 | 11/1998 |
| WO | 2000016810 A1 | 3/2000 |
| WO | 2001005161 A1 | 1/2001 |
| WO | 2001043781 A1 | 6/2001 |
| WO | 2003074091 A2 | 9/2003 |
| WO | 2004065491 A1 | 8/2004 |
| WO | 2005000218 A1 | 1/2005 |
| WO | 2006/078914 A1 | 7/2006 |
| WO | 2006078914 A1 | 7/2006 |
| WO | 2008017074 A2 | 2/2008 |
| WO | 2011002209 A2 | 1/2011 |
| WO | 2013112554 A1 | 8/2013 |
| WO | 2016179350 A1 | 11/2016 |

OTHER PUBLICATIONS

Becker, A. et al., "Transferrin-mediated tumor delivery of contrast media for optical imaging and magnetic resonance imaging," Part of the SPIE Conference on Molecular Imaging: Reporters, Dyes, Markers and Instrumentation, Jan. 1999, pp. 142-150, vol. 3600.

Becker, A. et al., "Receptor-targeted optical imaging of tumors with near-infrared fluorescent ligands," Nat. Biotechnol., Apr. 2001, pp. 327-331, vol. 19, Nature Publishing Group.

Becker, A. et al., "Cyanine Dye Labeled Vasoactive Intestinal Peptide and Somatostatin Analog for Optical Detection of Gastroenteropancreatic Tumors," Annals New York Academy of Sciences, 2000, pp. 275-278, vol. 921, No. 1.

Berezin, M. et al., "Ratiometric Analysis of Fluorescence Lifetime for Probing Binding Sites in Albumin with Near-Infrared Fluorescent Molecular Probes," Photochem. Photobiol., Nov./Dec. 2007, pp. 1371-1378, vol. 83, No. 6.

Definition of "Biomolecules," dated Jan. 2, 2014, from thefreedictionary.com; 2 pgs.

Bouteiller, C. et al., "Novel Water-Soluble Near-Infrared Cyanine Dyes: Synthesis, Spectral Properties, and Use in the Preparation of Internally Quenched Fluorescent Probes," Bioconjugate Chem., 2007, pp. 1303-1317, vol. 18, No. 4.

Braeckmans, K. et al., "Three-Dimensional Fluorescence Recovery after Photobleaching with the Confocal Scanning Laser Microscope," Biophys. J., Oct. 2003, pp. 2240-2252, vol. 85, No. 4.

Braga, J. et al., "Intracellular Macromolecular Mobility Measured by Fluorescence Recovery after Photobleaching with Confocal Laser Scanning Microscopes," Mol. Biol. Cell, Oct. 2004, pp. 4749-4760, vol. 15.

Bremer, C. et al., "Imaging of Differential Protease Expression in Breast Cancers for Detection of Aggressive Tumor Phenotypes," Radiology, Mar. 2002, pp. 814-818, vol. 222, No. 3.

(56) References Cited

OTHER PUBLICATIONS

Brinkley, M., "A Brief Survey of Methods for Preparing Protein Conjugates with Dyes, Haptens, and Cross-Linking Reagents," Bioconjugate Chem., 1992, pp. 2-13, vol. 3, No. 1.

Bugaj, J. et al., "Novel fluorescent contrast agents for optical imaging of in vivo tumors based on a receptor-targeted dye peptide conjugate platform," J. Biomed. Optics, Apr. 2001, pp. 122-133, vol. 6, No. 2.

Chipon, B. et al., "Synthesis and post-synthetic derivatization of a cyanine-based amino acid. Application to the preparation of a novel water-soluble NIR dye," Tetrahedron Letters, 2006, pp. 8279-8284, vol. 47.

Cooper, S., "Polyurethane Biomaterials," Abstract of video lecture; presented Nov. 9, 2011, online at http://hdl.handle.net/1853/42056; downloaded Jul. 22, 2016 from https://smartech.gatech.edu/handle/1853/42056; 3 pgs.

De Jong, M. et al., "Comparison of 111In-labeled Somatostatin Analogues for Tumor Scintigraphy and Radionuclide Therapy," Cancer Res., Feb. 1, 1998, pp. 437-441, vol. 58.

Gordon, G. et al., "Analysis of Simulated and Experimental Fluorescence Recovery After Photobleaching. Data for Two Diffusing Components," Biophys. J., Mar. 1995, pp. 766-778, vol. 68.

Haraguchi, T., "Live Cell Imaging: Approaches for Studying Protein Dynamics in Living Cells," Cell Structure and Function, 2002, pp. 333-334, vol. 27, Japan Society for Cell Biology.

Hilderbrand, S. et al., "Monofunctional Near-Infrared Fluorochromes for Imaging Applications," Bioconjugate Chem., 2005, pp. 1275-1281, vol. 16, No. 5.

International Search Report and Written Opinion dated Dec. 27, 2004 from related International Patent Application No. PCT/US2004/017142; 6 pgs.

International Search Report and Written Opinion dated Sep. 9, 2016 from related International Patent Application No. PCT/US2016/030893; 13 pgs.

Ito, S. et al., "Development of Fluorescence-Emitting Antibody Labeling Substance for Near-Infrared Ray Excitation," Bioorg. Med. Chem. Lett., 1995, pp. 2689-2694, vol. 5, No. 22, Elsevier Science Ltd., Great Britain.

Jain, R., "Barriers to Drug Delivery in Solid Tumors," Scientific American, Jul. 1994, pp. 58-65, vol. 271.

Lee, H. et al., "Heptamethine Cyanine Dyes with a Robust C—C Bond at the Central Position of the Chromophore", J. Org. Chem., 2006, pp. 7862-7865, vol. 71.

Lee, H. et al., "Synthesis and Spectral Properties of Near-Infrared Aminophenyl-, Hydroxyphenyl- and Phenyl-Substituted Heptamethine Cyanines," J. Org. Chem., 2008, pp. 723-725, vol. 73.

Lenhard, J. et al., "Electrochemistry and Electronic Spectra of Cyanine Dye Radicals in Acetonitrile," J. Phys. Chem., 1993, pp. 4916-4925, vol. 97.

Lewis, J. et al., "Comparison of Four 64Cu-Labeled Somatostatin Analogues in Vitro and in a Tumor-Bearing Rat Model: Evaluation of New Derivatives for Positron Emission Tomography Imaging and Targeted Radiotherapy," J. Med. Chem., 1999, pp. 1341-1347, vol. 42.

Licha, K. et al., "Hydrophilic Cyanine Dyes as Contrast Agents for Near-infrared Tumor Imaging: Synthesis, Photophysical Properties and Spectroscopic In vivo Characterization," Photochem. Photobiol., Sep. 2000, pp. 392-398, vol. 72, No. 3.

Lukevits, E. et al., "Catalytic Synthesis and Reactions of Nitrogen Heterocycles (Review)," Chem. Heterocyclic Compounds, 1994, pp. 1284-1307, vol. 30, Nos. 11-12, Plenum Publishing Corporation.

Mujumdar, R. et al., "Cyanine Dye Labeling Reagents: Sulfoindocyanine Succinimidyl Esters," Bioconjugate Chem., Mar./Apr. 1993, pp. 105-111, vol. 4, No. 2.

Notice of Allowance dated Aug. 2, 2010 from related U.S. Appl. No. 10/559,000; 4 pgs.

Notice of Allowance dated Sep. 4, 2012 from related U.S. Appl. No. 12/192,480; 7 pgs.

Notice of Allowance dated Jul. 23, 2012 from related U.S. Appl. No. 12/938,086; 7 pgs.

Office Action dated Mar. 10, 2009 from related U.S. Appl. No. 10/559,000; 8 pgs.

Office Action dated Oct. 14, 2009 from related U.S. Appl. No. 10/559,000; 10 pgs.

Office Action dated Mar. 3, 2010 from related U.S. Appl. No. 10/559,000; 4 pgs.

Office action dated Aug. 19, 2011 from related U.S. Appl. No. 12/192,480; 10 pgs.

Office action dated Dec. 13, 2011 from related U.S. Appl. No. 12/192,480; 9 pgs.

Office action dated Mar. 7, 2011 from related U.S. Appl. No. 12/192,480; 13 pgs.

Office Action dated May 1, 2012 from related U.S. Appl. No. 12/192,480; 12 pgs.

Office Action dated May 25, 2012 from related U.S. Appl. No. 12/370,758; 12 pgs.

Office Action dated Sep. 30, 2011 from related U.S. Appl. No. 12/370,758; 12 pgs.

Office Action dated Aug. 28, 2014 from related U.S. Appl. No. 12/370,758; 10 pgs.

Office Action dated Dec. 4, 2015 from related U.S. Appl. No. 12/370,758; 10 pgs.

Office Action dated Apr. 3, 2012 from related U.S. Appl. No. 12/938,086; 8 pgs.

Office Action dated Jan. 17, 2014 from related U.S. Appl. No. 13/712,317; 15 pgs.

Office Action dated Nov. 4, 2016 from related U.S. Appl. No. 14/624,532; 11 pgs.

Office Action dated Jul. 5, 2017 from related U.S. Appl. No. 14/624,532; 9 pgs.

Office Action dated Apr. 6, 2017 from related U.S. Appl. No. 15/090,055; 17 pgs.

Office Action dated Jul. 24, 2017 from related U.S. Appl. No. 15/090,055; 16 pgs.

Office Action dated Dec. 1, 2017 from related U.S. Appl. No. 14/624,532; 8 pgs.

Ogul'Chansky, T. et al., "Interactions of cyanine dyes with nucleic acids. XXIV. Aggregation of monomethine cyanine dyes in the presence of DNA and its manifestation in absorption and fluorescence spectra," Spectrochimica Acta Part A, 2001, pp. 1525-1532, vol. 57, Elsevier Science B.V.

Patonay, G. et al., "Near-Infrared Fluorogenic Labels: New Approach to an Old Problem," Analytical Chemistry, Mar. 15, 1991, pp. 321A-327A, vol. 63, No. 6.

Pretsch, E et al., "UV-Absorption of alpha,beta-Unsaturated Carbonyl Compounds; UV-Absorption of Dienes and Polyenes; UV-Absorption of Aromatic Carbonyl Compounds; UV-Absorption of Aromatic Compounds," Spectral Data for Structure Determination of Organic Compounds, Chemical Laboratory Practice, 1989, Second ed., pp. U20, U25, U30, U35, U40, U45, U50, ISBN 3-540-512102-0, Springer-Verlag, Berlin, Heidelberg.

Registry No. 70446-35-4, Nov. 16, 1984, 1 pg.

Sigma Production Information for Sodium dodecyl sulfate, Product No. L 3771, Oct. 2002, 1 pg., available at https://www.sigmaaldrich.com/content/dam/sigma-aldrich/docs/Sigma/Product_Information_Sheet/2/l3771pis.pdf.

Weissleder, R., "A clearer vision for in vivo imaging," Nat. Biotechnology, Apr. 2001, pp. 316-317, vol. 19.

Ye, Y. et al., "Integrin Targeting for Tumor Optical Imaging," Theranostics, 2011, pp. 102-126, vol. 1.

European Search Report dated Sep. 18, 2019 in related European Application No. 19152382.8, 7 pages.

Liu, Hands-free, Wireless Goggles for Near-infrared Fluorescence and Real-time Image-guided Surgery, Surgery, May 2011, vol. 149(5), 16 pps.

Ye, Integrin Targeting for Tumor Optical Imaging, Theranostics, 2011, vol. 1, pp. 102-126.

International Search Report and Written Opinion dated Apr. 18, 2013 from related Patent Application No. PCT/US2013/022704; 6 pgs.

(56) References Cited

OTHER PUBLICATIONS

Qin, R., "Intraoperative Fluorescence Surgical Goggle," Apr. 2009; 9 pgs.

Rolland, J. et al., "Optical Versus Video See-Through Head-Mounted Displays in Medical Visualization," Presence, Jun. 2000, pp. 287-309, vol. 9, No. 3.

Troyan, S. et al., "The Flare Intraoperative Near-Infrared Fluorescence Imaging System: A First-in-Human Clinical Trial in Breast Cancer Sentinel Lymph Node Mapping," Ann. Surg. Oncol., 2009, pp. 2943-2952, vol. 16.

Office Action dated Aug. 9, 2019 from related U.S. Appl. No. 15/090,055; 9 pgs.

Office Action dated Jul. 11, 2014 from related U.S. Appl. No. 13/712,317; 12 pgs.

Office Action dated May 21, 2015 from related U.S. Appl. No. 13/712,317; 14 pgs.

Office Action dated Jul. 15, 2016 from related U.S. Appl. No. 14/624,532; 12 pgs.

Achilefu, S. et al., "Synthesis, in Vitro Receptor Binding, and in Vivo Evaluation of Fluorescein and Carbocyanine Peptide-Based Contrast Agents", J Med Chem., 45(10):2003-15, (2002).

Achilefu, S., "Lighting up Tumors with Receptor-Specific Optical Molecular Probes", Technol Cancer Res Treat., 3 (4):393-409, (2004).

Allman, R. et al., "In Vitro and in Vivo Effects of a Cyclic Peptide With Affinity for the alpha(nu)beta3 Integrin in Human Melanoma Cells", Eur J Cancer, 36(3):410-22, (2000).

Arap, W. et al., "Cancer Treatment by Targeted Drug Delivery to Tumor Vasculature in a Mouse Model", Science, 279(5349):377-80, (1998).

Arnaout, M. et al., "Coming to Grips With Integrin Binding to Ligands", Curr Opin Biol., 14(5):641-51, (2002).

Arnaout, M., "Integrin Structure: New Twists and Turns in Dynamic Cell Adhesion", Immunol Rev., 186:125-40, :2002).

Bloch, S. et al., "Targeting Beta-3 Integrin Using a Linear Hexapeptide Labeled with a Near-Infrared Fluorescent Molecular Probe", Mol Pharm., 3(5):539-49, (2006).

Bloch, S. et al., "Whole-Body Fluorescence Lifetime Imaging of a Tumor-Targeted Near-Infrared Molecular Probe in Mice", J Biomed Opt., 10(5):054003, (2005).

Enablement Decision Tree, accessed on Aug. 18, 2019, at Url: https://www.uspto.gov/web/offices/pacidapp/1pecba.htm#7, Example F, situation 1.

EP Patent Application No. 19152382.8; Extended European Search Report, dated Aug. 14, 2019; 7 pages.

Haubner, R. et al., "Glycosylated Rgd-containing Peptides: Tracer for Tumor Targeting and Angiogenesis Imaging Nith Improved Biokinetics", J Nucl Med., 42(2):326-36, (2001).

Haubner, R. et al., "Noninvasive Imaging of alpha(v)beta3 Integrin Expression Using 18F-labeled RGD-containing Glycopeptide and Positron Emission Tomography", Cancer Res., 61(5):1781-5, (2001).

Haubner, R. et al., "Radiolabeled alpha(v)beta3 Integrin Antagonists: A New Class of Tracers for Tumor Targeting", J Nucl Med., 40(6):1061-71, (1999).

International Application No. PCT/US2006/002056; International Preliminary Report on Patentability, date of issuance Jul. 24, 2007; 6 pages.

International Application No. PCT/US2006/002056; International Search Report and Written Opinion of the International Searching Authority, dated May 24, 2006; 7 pages.

International Application No. PCT/US2013/022704; International Preliminary Report on Patentability, dated Jul. 29, 2014; 5 pages.

International Application No. PCT/US2016/030893; International Preliminary Report on Patentability, dated Nov. 7, 2017; 9 pages.

International Appliction No. PCT/US2006/002056; International Preliminary Report on Patentability, dated Jul. 24, 2007, (mailing date Aug. 2, 2007); 7 pages.

Janssen, M. et al., "Tumor Targeting With Radiolabeled alpha(v)beta(3) Integrin Binding Peptides in a Nude Mouse Model", Cancer Res., 62(21):6146-51, (2002).

Jones, J. et al., "Evaluation of a Tumor-Targeting, Near-Infrared Fluorescent Peptide for Early Detection and Endoscopic Resection of Polyps in a Rat Model of Colorectal Cancer", Mol Imaging, 17:1-9, (2018).

National Institute of Cancer—Understanding and Related Topics, accessed Aug. 18, 2019 at URL: https://www.cancer.gov/about-cancer/understanding/what-is-cancer; 9 pages.

Qin, R., "Intraoperative Fluorescence Surgical Goggle", Knowledge Bank Osu.Edu, 9 pages, (2009).

Roland, J. et al., "Optical Versus Video See-Through Head-Mounted Displays in Medical Visualization", Presence, 9(3):287-309, (2000).

Shen, D. et al., "Selective Imaging of Solid Tumours Via the Calcium-Dependent High Affinity Binding of a Cyclic Dctapeptide to Phosphorylated Annexin A2", Nat Biomed Engin., 4:298-313, (2020).

Sivolapenko, G. et al., "Imaging of Metastatic Melanoma Utilising a technetium-99m Labelled RGD-containing Synthetic Peptide ", Eur J Nucl Med, 25(10):1383-9, (1998).

Troyan, S. et al., "The Flare Intraoperative Near-Infrared Fluorescence Imaging System: A First-in-Human Clinical Trial in Breast Cancer Sentinel Lymph Node Mapping", Ann Surg Oncol., 16(10):2943-52, (2009).

U.S. Appl. No. 16/189,551; Notice of Allowance, dated Jan. 20, 2020; 5 pages.

Van Hagen, P. et al., "Evaluation of a Radiolabelled Cyclic DTPA-RGD Analogue for Tumour Imaging and Radionuclide Therapy", Int J Cancer, 90(4):186-98, (2000).

Yang, L. et al., "Hands-Free, Wireless Goggles for Near-Infrared Fluorescence and Real-Time Image-Guided Surgery", Surgery, 149(5):689-98, (2011).

Ye, Y. et al., "Design, Synthesis, and Evaluation of Near Infrared Fluorescent Multimeric RGD Peptides for Targeting Tumors ", J Med Chem., 49(7):2268-75, (2006).

Ye, Y. et al., "Multivalent Carbocyanine Molecular Probes: Synthesis and Applications", Bioconjug Chem, 16(1):51-61, :2005).

Ye, Y. et al., "Novel Near-Infrared Fluorescent Integrin-Targeted DFO Analogue", Bioconjug Chem., 19(1):225-34, :2008).

Ye, Y. et al., "Polyvalent Carbocyanine Molecular Beacons for Molecular Recognitions", J Am Chem, 126(25):7740-1, :2004).

Zhang, Z. et al., "Monomolecular Multimodal Fluorescence-Radioisotope Imaging Agents", Bioconjug Chem., 16(5):1232-9, (2005).

* cited by examiner

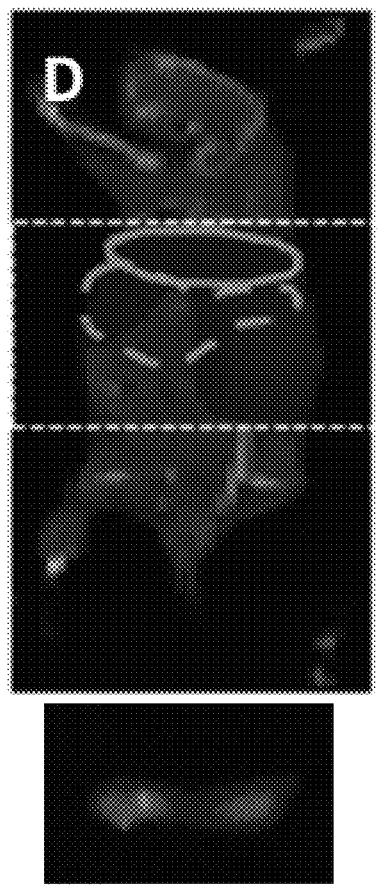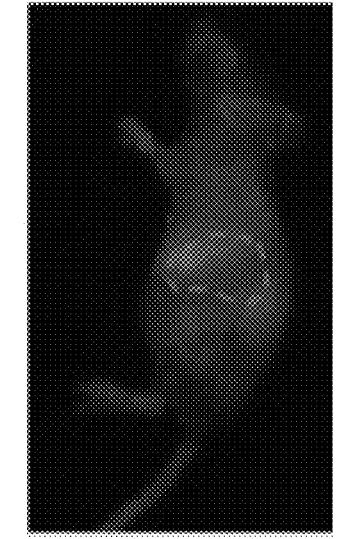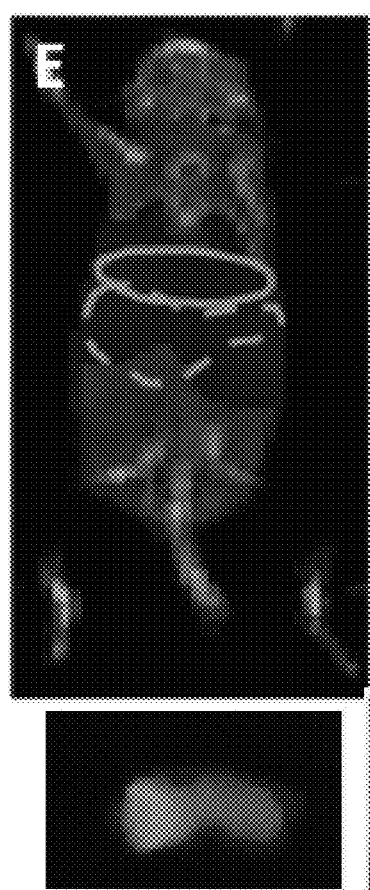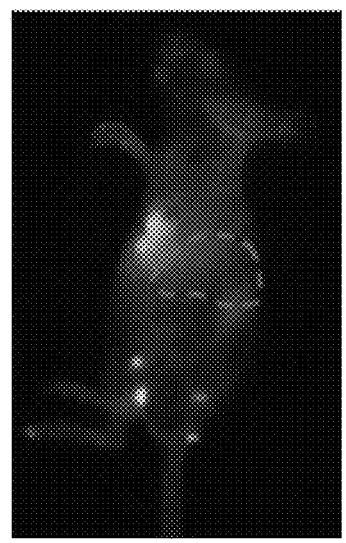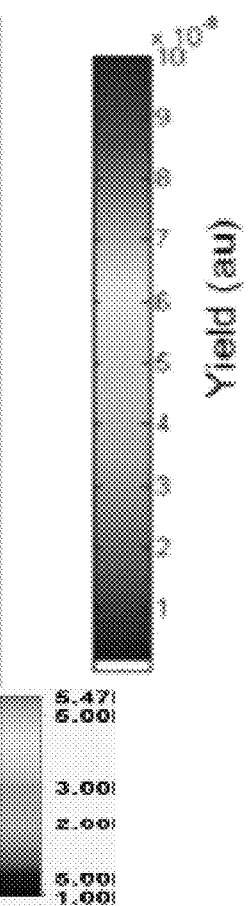
FIG. 9D
FIG. 9E

COMPOUNDS HAVING RD TARGETING MOTIFS AND METHODS OF USE THEREOF

CROSS REFERENCE TO RELATED APPLICATIONS

This application claims the benefit of PCT Application PCT/US2016/030893, filed May 5, 2016, which claims the benefit of U.S. Provisional Application No. 62/157,667, filed May 6, 2015, each of the disclosures of which is hereby incorporated by reference in its entirety.

GOVERNMENTAL RIGHTS

This invention was made with government support under CA171651 awarded by the NIH/NCI. The government has certain rights in the invention.

FIELD OF THE INVENTION

The present invention provides compounds that have motifs that target the compounds to cells that express integrins. In particular, the compounds have peptides with one or more RD motifs conjugated to an agent selected from an imaging agent and a targeting agent. The compounds may be used to detect, monitor and treat a variety of disorders mediated by integrins.

BACKGROUND OF THE INVENTION

Angiogenesis, the formation of new blood vessels, is the cardinal feature of virtually all malignant tumors and because of its commonality, probing tumor-induced angiogenesis and associated proteins is a viable approach to detect and treat a wide range of cancers. Angiogenesis is stimulated by integrins, a large family of transmembrane proteins that mediate dynamic linkages between extracellular adhesion molecules and the intracellular actin skeleton. Integrins are composed of two different subunits, α and β, which are non-covalently bound into αβ complexes. Particularly, the expression of $\alpha_v\beta_3$ integrin (ABI) in tumor cells undergoing angiogenesis and on the epithelium of tumor-induced neovasculature alters the interaction of cells with the extracellular matrix, thereby increasing tumorigenicity and invasiveness of cancers.

Numerous studies have shown that ABI and more than 7 other heterodimeric integrins recognize proteins and low molecular weight ligands containing RGD (arginine-glycine-aspartic acid) motifs in proteins and small peptides. Based on structural and bioactivity considerations, cyclic RGD peptide ligands are preferred as delivery vehicles of molecular probes for imaging and treating ABI-positive tumors and proliferating blood vessels. Until recently, most of the in vivo imaging studies were performed with radiopharmaceuticals because of the high sensitivity and clinical utility of nuclear imaging methods. Particularly, the use of small monoatomic radioisotopes does not generally interfere with the biodistribution and bioactivity of ligands. Therefore, once a high affinity ligand for a target receptor is identified, the radiolabeled analogue is typically used to monitor the activity, pharmacokinetics and pharmacodynamics of the drug or imaging agent. Despite these advantages, nuclear imaging is currently performed in specialized centers because of regulatory, production and handling issues associated with radiopharmaceuticals. Optical imaging is an alternative, but complementary method to interrogate molecular processes in vivo and in vitro.

Optical imaging for biomedical applications typically relies on activating chromophore systems with low energy radiation between 400 and 1500 nm wavelengths and monitoring the propagation of light in deep tissues with a charge-coupled device (CCD) camera or other point source detectors. Molecular optical imaging of diseases with molecular probes is attractive because of the flexibility to alter the detectable spectral properties of the beacons, especially in the fluorescence detection mode. The probes can be designed to target cellular and molecular processes at functional physiological concentrations. For deep tissue imaging, molecular probes that are photoactive in the near infrared (NIR) instead of visible wavelengths are preferred to minimize background tissue autofluorescence and light attenuation caused by absorption by intrinsic chromophores. In contrast to radioisotopes, the NIR antennas are usually large heteroatomic molecules that could impact the biodistribution and activity of conjugated bioactive ligands. However, previous studies have shown that conjugating small peptide carriers with NIR molecular probes successfully delivered the beacons to target proteins in vivo, and the nonspecific distribution of the conjugate in non-target tissues can be minimized by adjusting the net lipophilicity and ionic character of the conjugate.

A need, however, exists for additional compounds that can target and monitor integrin expression. In particular, a need exists for compounds that can target, monitor and/or treat a variety of integrin-mediated disorders.

SUMMARY OF THE INVENTION

In an aspect, the disclosure provides a compound having the formula:

wherein:
$R^1$ is a carbocyanine dye or derivative thereof;
$R^2$ is selected from the group consisting of a treatment agent, hydrogen, hydroxyl, $NH_2$, hydrocarbyl, and substituted hydrocarbyl;
$X^1_m$—R-D-$X^2_p$ together form a linear or cyclic peptide;
$X^1$ and $X^2$ are independently selected from any amino acid residue;
m is an integer from 1 to about 10;
n is an integer from 1 to about 10;
p is an integer from 1 to about 10; and
a dash (-) represent a covalent bond.

In another aspect, the disclosure provides a compound having formula (II):

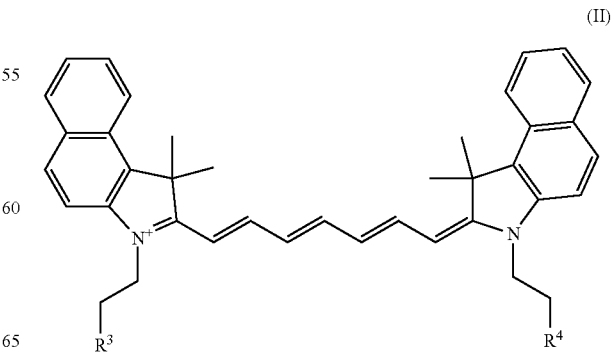

wherein:
R³ is selected from the group consisting of nanoparticles, small organic molecules, peptides, organometallics, metal chelates, proteins, drugs, antibiotics, and carbohydrates; and
R⁴ is $[X^1_m\text{—R-D-}X^2_p]_n\text{—Y—}R^2$, wherein:
R² is independently selected from the group consisting of a hydrogen, hydroxyl, NH₂, hydrocarbyl, and substituted hydrocarbyl;
X¹ and X² are independently selected from any amino acid residue;
$X^1_m\text{—R-D-}X^2_p$ together form a linear or cyclic peptide;
m is an integer from 1 to about 10;
n is an integer from 1 to about 10;
p is an integer from 1 to about 10; and
a dash (-) represent a covalent bond.

In still another aspect, the disclosure provides a compound having formula (II):

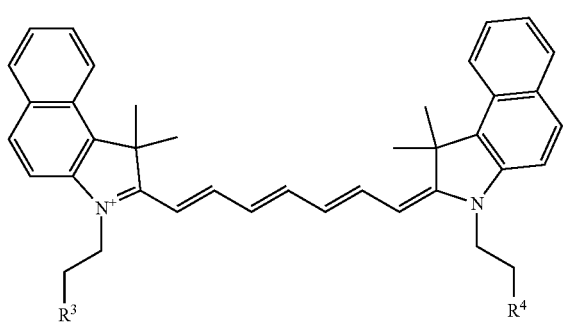

(II)

wherein:
R³ is selected from the group consisting of nanoparticles, small organic molecules, peptides, organometallics, metal chelates, proteins, drugs, antibiotics, and carbohydrates; and
R⁴ is selected from the group consisting of:

| SEQ ID NO: | R⁴ |
|---|---|
| 8 | CONH-[<sub>D</sub>Cys-Gly-Arg-Asp-Ser-Pro-Cys]-Lys-Tyr-OH |
| 9 | CONH-[<sub>D</sub>Cys-Gly-Arg-Asp-Ser-Pro-Cys]-Tyr-OH |
| 10 | CONH-[<sub>D</sub>Cys-Gly-Arg-Asp-Ser-Pro-Cys]-Tyr-Lys-OH |
| 11 | CONH-[<sub>D</sub>Cys-Gly-Arg-Asp-Ser-Pro-<sub>D</sub>Cys]-Tyr-OH |
| 12 | CONH-[Cys-Gly-Arg-Asp-Ser-Pro-Cys]-Tyr-OH |
| 13 | CONH-[Cys-Arg-Gly-Asp-Ser-Pro-Cys]-Tyr-OH |
| 14 | CONH-[<sub>D</sub>Cys-Arg-Gly-Asp-Ser-Pro-Cys]-Tyr-OH |
| 15 | CONH-[<sub>D</sub>Cys-Arg-Gly-Asp-Ser-Pro-<sub>D</sub>Cys]-Tyr-OH |
| 17 | CONH-Gly-[<sub>D</sub>Cys-Gly-Arg-Asp-Ser-Pro-Cys]-Tyr-OH |
| 18 | CONH-Gly-[<sub>D</sub>Cys-Gly-Arg-Asp-Ser-Pro-Cys]-<sub>D</sub>Tyr-OH |
| 19 | CONH-Gly-[<sub>D</sub>Cys-Gly-Arg-Asp-Ser-Pro-Cys]-<sub>D</sub>Tyr-Lys-OH |
| 20 | CONH-Gly-[Cys-Gly-Arg-Asp-Ser-Pro-Cys]-<sub>D</sub>Tyr-Lys-OH |
| 21 | CONH-Gly-[<sub>D</sub>Cys-Gly-Arg-Asp-Ser-Pro-<sub>D</sub>Cys]-Tyr-OH |
| 22 | CONH-Gly-[Cys-Gly-Arg-Asp-Ser-Pro-<sub>D</sub>Cys]-Tyr-OH |
| 23 | CONH-Gly-[<sub>D</sub>Cys-Gly-Arg-Asp-Ser-Pro-<sub>D</sub>Cys]-<sub>D</sub>Tyr-OH |

In still yet another aspect, the disclosure provides a method for detecting expression of a β3 subunit of integrin in a cell, the method comprising: (a) contacting a population of cells with a compound of the disclosure; and detecting the presence of a signal emitted from the carbocyanine dye of the compound of the disclosure in the population of cells, the signal being emitted from a cell expressing a β3 subunit of integrin.

In a different aspect, the disclosure provides a method for detecting cancer, the method comprising: (a) administering a composition comprising an effective amount of a compound of the disclosure to a subject; and (b) detecting the presence of a signal emitted from the carbocyanine dye of the compound of the disclosure in the subject, wherein detection of signal above baseline indicates cancer.

In other aspects, the disclosure provides a method for detecting pancreatic cancer, the method comprising: (a) administering a composition comprising an effective amount of a compound of the disclosure to a subject; and (b) detecting the presence of a signal emitted from the carbocyanine dye of the compound of the disclosure in the subject, wherein detection of signal above baseline indicates pancreatic cancer.

In yet other aspects, the disclosure provides a method for detecting early stage pancreatic ductal adenocarcinoma (PDAC) or precursor pancreatic intraepithelial neoplasia (PanIN), the method comprising: (a) administering a composition comprising an effective amount of a compound of the disclosure to a subject; and (b) detecting the presence of a signal emitted from the carbocyanine dye of the compound of the disclosure in the subject, wherein detection of signal above baseline indicates early stage pancreatic ductal adenocarcinoma (PDAC) or precursor pancreatic intraepithelial neoplasia (PanIN).

In still yet other aspects, the disclosure provides a method for differentiating pancreatic ductal adenocarcinoma (PDAC) and precursor pancreatic intraepithelial neoplasia (PanIN) from pancreatitis, the method comprising: (a) administering a composition comprising an effective amount of a compound of the disclosure to a subject; and (b) detecting the presence of a signal emitted from the carbocyanine dye of the compound of the disclosure in the subject, wherein detection of signal above baseline indicates PDAC or PanIN and detection of a signal at or below baseline indicates pancreatitis.

In certain aspects, the disclosure provides a method for differentiating pancreatic ductal adenocarcinoma (PDAC) and PanIN-3 from PanIN-1/2 and ductal hyperplasia/metaplasia, the method comprising: (a) administering a composition comprising an effective amount of a compound of the disclosure to a subject; and (b) detecting the presence of a signal emitted from the carbocyanine dye of the compound of the disclosure in the subject, wherein detection of signal above baseline indicates PDAC or PanIN-3 and detection of a signal at or below baseline indicates PanIN-1/2 or ductal hyperplasia/metaplasia.

BRIEF DESCRIPTION OF THE FIGURES

The application file contains at least one drawing executed in color. Copies of this patent application publication with color drawing(s) will be provided by the Office upon request and payment of the necessary fee.

(FIG. 2A) LS288; (FIG. 2B) LS798; (FIG. 2C) LS276; and (FIG. 2D) LS843.

(FIG. 3A) Cypate (cypate 4); (FIG. 3B) Cypate 3; and (FIG. 3C) Cypate 2.

(FIG. 4A) Cypate4; (FIG. 4B) Cypate3; (FIG. 4C) Cypate2.

(FIG. 7A) (1) ICG: $R_1=R_2=SO_3$; (2) Cypate: $R_1=R_2=CO_2H$; (3) LS838: $R_1=CO_2H$; $R_2=CONH$-cyclo-($_D$Cys-Gly-Arg-Asp-Ser-Pro-Cys)-Tyr-OH (SEQ ID NO:9). (FIG. 7B) LS276; (FIG. 7C) LS288.

FIG. 9A, FIG. 9B, FIG. 9C, FIG. 9D and FIG. 9E depict noninvasive FMT (top), corresponding ex vivo (middle), and side-view of the pancreas from planar fluorescence imaging of pancreatic lesions in mouse models (bottom). FIG. 9A, Advanced KPC; FIG. 9B, 1 week PDAC; FIG. 9C, 2 weeks PDAC; FIG. 9D, pancreatitis; and FIG. 9E, sham surgery using orthotopic Matrigel implant demonstrated selective uptake of LS838 in PDAC, but not in non-tumor controls. The reconstructed yield is superimposed with the corresponding CT data 10 mm below from the dorsal side. Dotted red circles: PDAC; solid red circles in C: positive nodules indicated by white arrow.

FIG. 10A, 1 week after orthotopic PDAC implant; FIG. 10B, 2-week orthotopic PDAC implant; FIG. 10C, advanced spontaneous KPC model showing high fluorescence uptake in tumor tissue; FIG. 10D, chronic pancreatitis showing low fluorescence overall but significant fluorescence in regions suspected to progress toward malignancy; probably PanIN-3; FIG. 10E, sham surgery demonstrating minimal LS838 fluorescence.

DETAILED DESCRIPTION OF THE INVENTION

Figure 1:
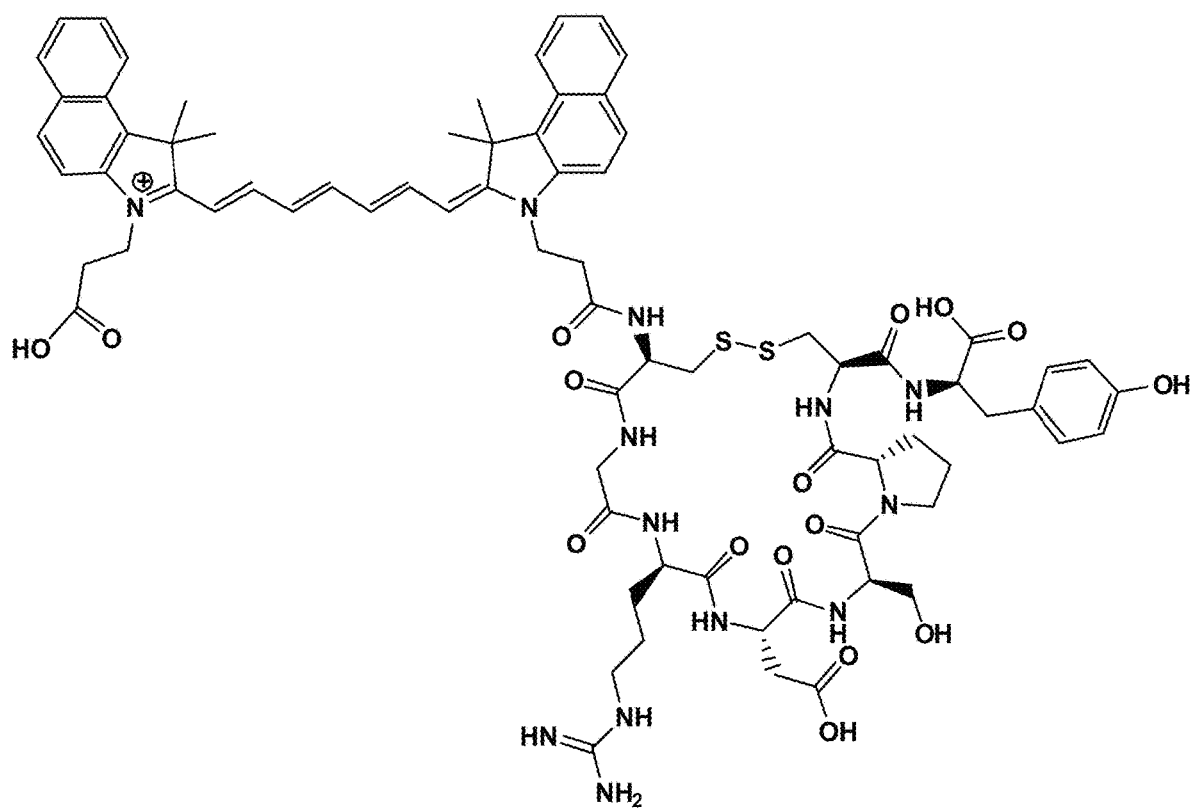
FIG. 1 depicts the structure of LS838.
Figure 2B:
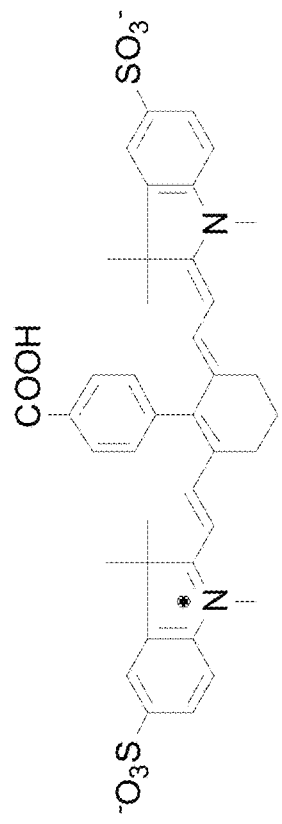
FIG. 2A, FIG. 2B, FIG. 2C and FIG. 2D depict the structures of NIR dyes with different hydrophobicity.
Figure 2D:
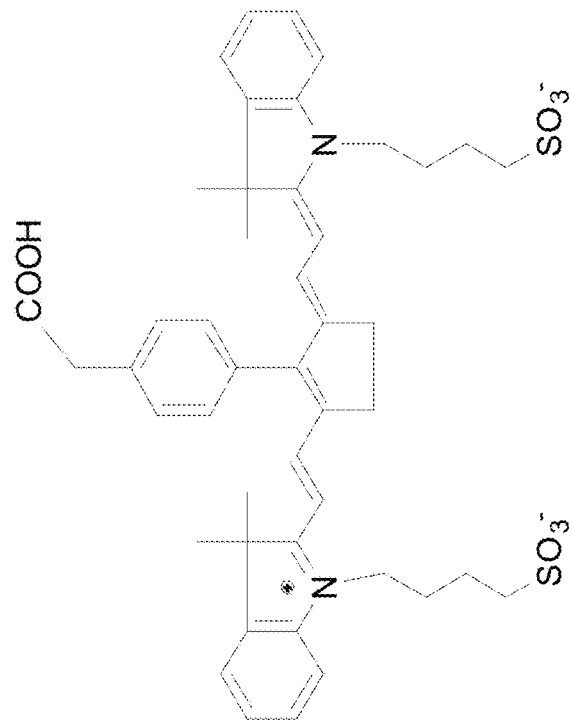
Figure 2A:
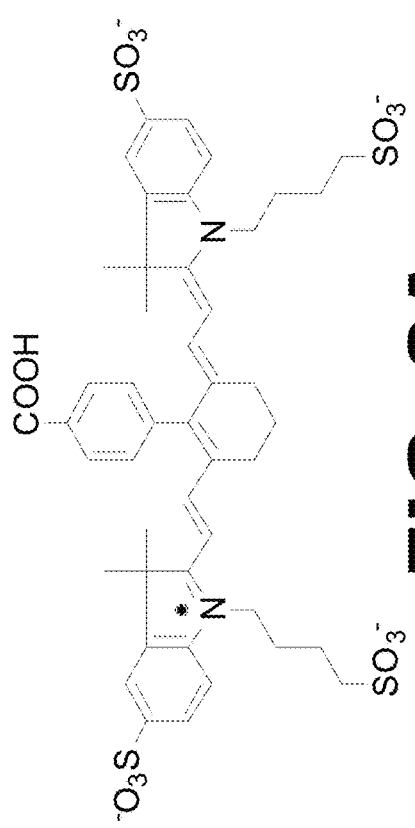
Figure 2C:
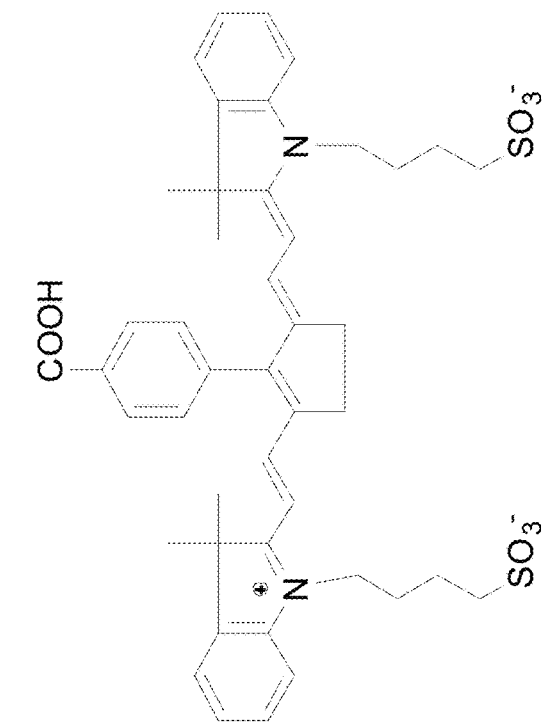
Figure 3A:
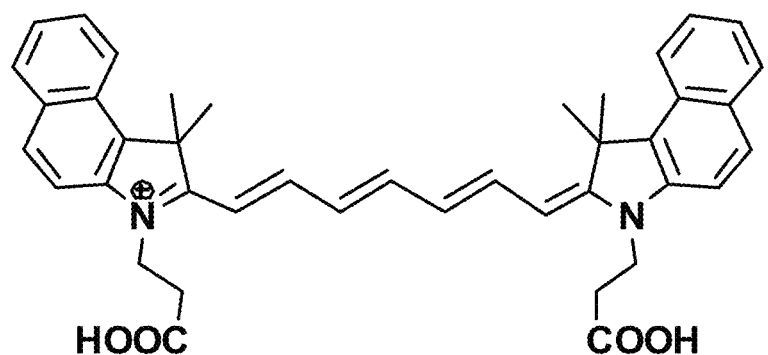
FIG. 3A, FIG. 3B and FIG. 3C depict the structure of cypates.
Figure 3B:
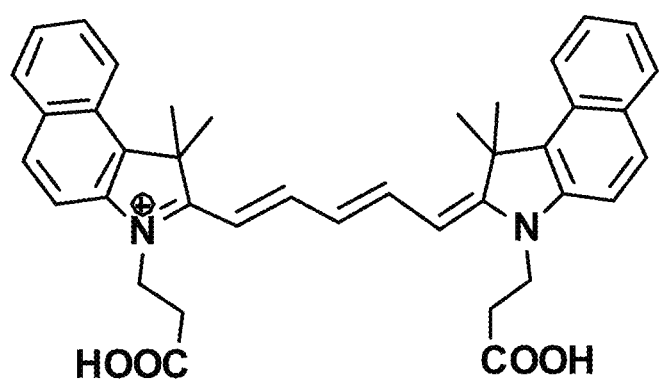
Figure 3C:
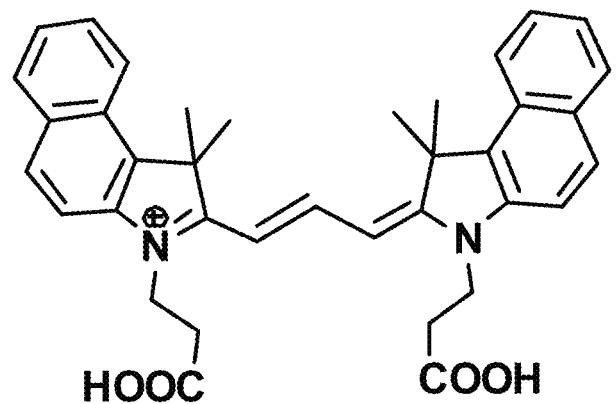

It has been discovered, as detailed in the examples, that a compound comprising a peptide having a RD motif and a tyrosine that is not adjacent to an imaging agent targets to a cell that expresses integrins. Unexpectedly, a peptide comprising a tyrosine non-adjacent to a carbocyanine dye conferred enhanced brightness relative to the same peptide without a tyrosine. Further, a peptide comprising a tyrosine adjacent to a carbocyanine dye resulted in a compound that was rapidly lost and was not retained in the tumor. Thus, the presence and location of the tyrosine is an essential feature of a compound of the disclosure that unexpectedly improves the properties of the carbocyanine dye comprising the peptide.

The present invention, accordingly, provides compounds that may be used to detect, monitor, and treat a variety of integrin-mediated biological processes, including the progression of disease states such as diabetes, cardiovascular disease, inflammation and cancer. Specifically a compound of the invention may be used in pancreatic cancer, for example to detect small or microscopic disease as well as differentiate between pancreatic cancer and pancreatitis.

I. Compounds

The compounds of the invention typically comprise at least one linear or cyclic peptide conjugated to an imaging agent and, optionally, a treatment agent, wherein the peptide comprises an RD motif and a tyrosine non-adjacent to the imaging agent. The peptide may be conjugated to the imaging agent and/or treatment agent directly by a covalent bond. Alternatively, the peptide may be conjugated to the imaging agent and/or treatment agent by a linker. Suitable linkers are described below. In a specific embodiment, the imaging agent is a carbocyanine dye.

(a) Peptide Regions of the Compound

Generally, the peptide portion of the compound minimally has a size that includes at least one RD motif and a tyrosine that is non-adjacent to an imaging agent. In an alternative embodiment, the peptide portion of the compound minimally has a size that includes at least one RGD motif and a tyrosine that is non-adjacent to an imaging agent. In some embodiments, the peptide may be linear. In other embodiments, the peptide may be cyclic. Typically, the peptide will have from about 3 to about 50 amino acid residues. In another embodiment, the peptide will have from about 3 to about 30 amino acid residues. In a further embodiment, the peptide will have from about 3 to about 20 amino acid residues. In yet another embodiment, the peptide will have from about 3 to about 15 amino acid residues. In still another embodiment, the peptide will have from about 4 to about 12 amino acid residues. In a further embodiment, the peptide will have from about 4 to about 8 amino acid residues. In a specific embodiment, the peptide will have from about 8 to about 10 amino acid residues. In another embodiment, the peptide will have 4 amino acid residues. In an additional embodiment, the peptide will have 5 amino acid residues. In still another embodiment, the peptide will have 6 amino acid residues. In an additional embodiment, the peptide will have 7 amino acid residues. In yet another embodiment, the peptide will have 8 amino acid residues. In a different embodiment, the peptide will have 9 amino acid residues. In other embodiments, the peptide will have 10 amino acid residues. In each of the aforementioned embodiments, the peptide, irrespective of its length, has at least one RD motif and a tyrosine that is not adjacent to an imaging agent. It will be appreciated by the skilled artisan that it is possible and, depending upon the embodiment, it may be desirable to have more than one RD motif or RGD motif within a peptide. For example, it is envisioned, depending upon the length of the peptide, that there may be from 2 to about 5 RD motifs or RGD motifs in a given peptide.

The choice of amino acid residues, in addition to the RD motif or RGD motif, that will comprise the peptide will vary greatly depending upon the particular application for the compound. For example, it may be desirable in certain imaging or treatment applications that the compound be substantially hydrophilic. In other imaging or treatment applications, it may be desirable for the compound to be substantially hydrophobic. Generally, the amino acids may be selected from any amino acid residue including hydrophobic amino acids (e.g., L, A, P, V, M, F, W, and I), polar, uncharged amino acids (e.g., G, S, N, Q, T, Y, and C), acidic amino acids (e.g., D and E) and basic amino acids (e.g., K, H, and R). The amino acid residues may also be modified amino acid residues that are commonly known in the art. For embodiments in which a hydrophobic compound is desired, typically the amino acid residues comprising the peptide will be predominantly selected from hydrophobic amino acids. In embodiments in which a hydrophilic compound is desired, typically the amino acid residues comprising the peptide will be predominantly polar, uncharged or polar, charged amino residues. An amino acid may be a naturally occurring L-amino acid or a non-natural D-amino acid. In certain embodiments, the D-amino acid is D-cysteine and/or D-tyrosine. In a specific embodiment, the D-cysteine is linked to an imaging agent. In other specific embodiments, the D-cysteine is linked to a carbocyanine dye. The inventors have shown that the unnatural D-cysteine linked to a carbocyanine dye confers high stability on the compound. Without wishing to be bound by theory, it is believed that this is because of the resistance of the compound to degradation by proteases. In an embodiment, a peptide of the invention is a cyclic peptide, wherein the peptide comprises two cysteines which cyclize the peptide by forming a disulfide bridge. In a specific embodiment, a peptide of the invention is a cyclic peptide comprising $_D$Cys-Gly-Arg-Asp-Ser-Pro-Cys (SEQ ID NO:24) or $_D$Cys-Gly-Arg-Asp-Ser-Pro-$_D$Cys (SEQ ID NO:25). Following the cyclic peptide, the peptide further comprises a tyrosine (Tyr). The Tyr residue unexpectedly increases the brightness of the compound such that smaller amounts are needed. Further, the location of the Tyr residue is important, as it was discovered that positioning the Tyr next to the carbocyanine dye led to rapid loss of retention of the compound in vivo. In a specific embodiment, a peptide of the invention may comprise Cyclo($_D$Cys-Gly-Arg-Asp-Ser-Pro-Cys)-Tyr (SEQ ID NO:9).

Further, the peptide may comprise additional amino acids before and/or after the cyclic peptide and tyrosine. For example, the peptide may comprise 1, 2, 3, 4, or 5 amino acids prior to the cyclic peptide. Additionally, the peptide may comprise 1, 2, 3, 4, or 5 amino acids after the Tyr. Non-limiting examples of peptides for use in a compound of the disclosure include those listed in Table A. In a specific embodiment, a peptide for use in a compound may be selected from the peptides of Table A.

TABLE A

| SEQ ID NO: | Peptide |
|---|---|
| 8 | $_D$Cys-Gly-Arg-Asp-Ser-Pro-Cys-Lys-Tyr |
| 9 | $_D$Cys-Gly-Arg-Asp-Ser-Pro-Cys-Tyr |
| 10 | $_D$Cys-Gly-Arg-Asp-Ser-Pro-Cys-Tyr-Lys |
| 11 | $_D$Cys-Gly-Arg-Asp-Ser-Pro-$_D$Cys-Tyr |
| 12 | Cys-Gly-Arg-Asp-Ser-Pro-Cys-Tyr |
| 13 | Cys-Arg-Gly-Asp-Ser-Pro-Cys-Tyr |
| 14 | $_D$Cys-Arg-Gly-Asp-Ser-Pro-Cys-Tyr |
| 15 | $_D$Cys-Arg-Gly-Asp-Ser-Pro-$_D$Cys-Tyr |
| 17 | Gly-$_D$Cys-Gly-Arg-Asp-Ser-Pro-Cys-Tyr |
| 18 | Gly-$_D$Cys-Gly-Arg-Asp-Ser-Pro-Cys-$_D$Tyr |
| 19 | Gly-$_D$Cys-Gly-Arg-Asp-Ser-Pro-Cys-$_D$Tyr-Lys |
| 20 | Gly-Cys-Gly-Arg-Asp-Ser-Pro-Cys-$_D$Tyr-Lys |
| 21 | Gly-$_D$Cys-Gly-Arg-Asp-Ser-Pro-$_D$Cys-Tyr |
| 22 | Gly-Cys-Gly-Arg-Asp-Ser-Pro-$_D$Cys-Tyr |
| 23 | Gly-$_D$Cys-Gly-Arg-Asp-Ser-Pro-$_D$Cys-$_D$Tyr |

In an alternative embodiment, the compound may have more than one peptide having a RD motif or RGD motif with the size (i.e., number of amino acid residues) and amino acid composition detailed above. For applications involving more than one peptide, the individual peptides may form a single continuous chain with each individual peptide attached together either directly by a covalent bond or they may be separated by a linker. The single continuous chain of individual peptides may then be conjugated to the agent either directly via a covalent bond or by a linker. Alternatively, individual peptides may each be conjugated directly to the agent by either a covalent bond or by a linker. The number of individual peptides can and will vary. Typically, there may be from about 1 to about 15 peptides having a RD motif or RGD motif. In another embodiment, there may be from about 1 to about 12 peptides. In a further embodiment, there may be from about 1 to about 10 peptides. In yet another embodiment, there may be from about 1 to about 5 peptides. In a further embodiment, there is one peptide. In yet another embodiment, there are two peptides. In an additional embodiment, there are 3 peptides. In an additional embodiment, there are 4 peptides. In still another embodiment, there are 5 peptides.

(b) Imaging Agents and Treatment Agents

The compound of the invention includes at least one imaging agent and, optionally, a treatment agent. In one embodiment, the compound may comprise an imaging agent. In an alternative embodiment, the compound may comprise an imaging agent and a treatment agent. Irrespective of the embodiment, the agent(s) may be either conjugated to the compound by a covalent bond or conjugated via a linker.

Several imaging agents are suitable for use to the extent that they provide the ability to detect or monitor the localization of the compound(s) of the present invention. In one embodiment, the imaging agent comprises an optical imaging agent. Optical imaging agents suitable for use in the invention can and will vary depending on the embodiment, but include fluorophores, organic fluorescent dyes, luminescent imaging agents, fluorescent lanthanide complexes, and fluorescent semiconductor nanocrystals. Examples of suitable visible (400-700 nm) fluorescent dyes include fluorescein, FITC, rhodamine, Texas Red, CyDyes (e.g., Cy3, Cy5, Cy5.5), Alexa Fluors (e.g., Alexa$^{488}$, Alexa$^{555}$, Alexa$^{594}$; Alexa$^{647}$) and DyDelight Dyes. Examples of suitable near infrared (NIR) (700-900 nm) fluorescent dyes include carbocyanine dyes, such as cypate and its derivatives. Luminescence imaging agents include luminescent lanthanide chelates and bioluminescence compounds (e.g., bacterial Lux, eukaryotic Luc or Ruc systems). In a specific embodiment, an imaging agent is a carbocyanine dye or a derivative thereof. Suitable carbocyanine dyes are known in the art or as described in the Examples. Non-limiting examples of carbocyanine dyes include those depicted in FIG. 1, FIG. 2A, FIG. 2B, FIG. 2C, FIG. 2D, FIG. 3A, FIG. 3B, FIG. 3C, FIG. 7A, FIG. 7B, FIG. 7C, and FIG. 13. In a specific embodiment, a compound of the disclosure comprises a carbocyanine dye selected from those depicted in FIG. 1, FIG. 2A, FIG. 2B, FIG. 2C, FIG. 2D, FIG. 3A, FIG. 3B, FIG. 3C, FIG. 7A, FIG. 7B, FIG. 7C, and FIG. 13. In another specific embodiment, a compound of the disclosure comprises a carbocyanine dye selected from the group consisting of Cypate (cypate 4), LS288, LS798, LS276, LS843, Cypate 3, and Cypate 2. A derivative of a carbocyanine dye may comprise a nonionic group (i.e. polyethylene glycol) or a positively charged moiety (i.e. $^+$NMe$_3$) conjugated to a free carboxylic acid group of a cypate. Alternatively, a derivative of a carbocyanine dye may comprise a functional group for conjugation of a radioisotope, treatment agent or other biologically active molecule. Non-limiting examples of biologically active molecules include nanoparticles, small organic molecules, peptides, proteins, organometallics, drugs, antibiotics, and carbohydrates. In certain embodiments, the biologically active molecule is <500 Da. Exemplary functional groups are depicted in Table 4 and FIG. 13. In a specific embodiment, a functional group is selected from the group consisting of an alkyne, azido (N$_3$), and a chelating agent. As used herein, a "chelating agent" is a molecule that forms multiple chemical bonds with a single metal atom. Examples of chelating agents include, but are not limited to, iminodicarboxylic and polyaminopolycarboxylic reactive groups, diethylenetriaminepentaacetic acid (DTPA), 1,4,7,10-tetraazacyclododecane-1,4,7,10-tetraacetic acid (DOTA), tetramethyl heptanedionate (TMHD), 2,4-pentanedione, ethylenediamine-tetraacetic acid disodium salt (EDTA), ethyleneglycol-O,O'-bis(2-aminoethyl)-N, N, N', N'-tetraacetic acid (EGTA), N-(2-hydroxyethyl) ethylenediamine-N,N',N'-triacetic acid trisodium salt (HEDTA), nitrilotriacetic acid (NTA), and 1,4,8,11-tetraazacyclotetradecane-N,N',N'',N'''-tetraacetic acid (TETA), deferoxamine (DFO), and derivatives thereof. A radioisotope, treatment agent and biologically active molecule are described below.

In an alternative embodiment, the imaging agent is a radiological imaging agent. In certain embodiments, a compound of the invention comprises two imaging agents: a carbocyanine dye or derivative thereof and a radioisotope. The radioisotope may be conjugated to the carbocyanine dye or may be conjugated to the Tyr of the peptide. A variety of radioisotopes that are capable of being detected, such as in a PET or SPECT diagnostic imaging procedure, are suitable for use in the present invention. Suitable examples of radiological imaging agents include Antimony-124, Antimony-125, Arsenic-74, Barium-103, Barium-140, Beryllium-7, Bismuth-206, Bismuth-207, Cadmium-109, Cadium-115, Calcium-45, Cerium-139, Cerium-141, Cerium-144, Cesium-137, Chromium-51, Gadolinium-153, Gold-195, Gold-199, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185, Palladium-103, Platinum-195, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110, Silver-111, Sodium-22, Strontium-85, Strontium-89, Strontium-90, Sulfur-35, Tantalum-182, Technetium-99, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. In a further alternative embodiment, the radiological imaging agent is selected from the group consisting of Technecium-99, Indium-111, Strontium-90, Iodine-125, Thallium-201, fluorine-18, carbon-11, carbon-13, nitrogen-13, Oxygen-15, Copper-64, Lutetium-177, Yttrium-90, and Iodine-123, Iodine-124, Iodine-125, and Iodine-131. In certain embodiments, a radioisotope may be used as an imaging agent and as a treatment agent. It is known in the art which radioisotopes function as both imaging agents and treatment agents. For example, since Iodine-131 has both a beta and gamma decay mode, it can be used for radiotherapy or for imaging.

A variety of other imaging agents are suitable for use in the invention. For example, other imaging agents include, gadolinium, metalloporphyrins, ferric chloride, ferric ammonium citrate, and ferrioxamine methanesulfonate for magnetic resonance imaging.

An imaging agent emits a signal that can be detected by a signal transducing machine. In some cases, imaging agent can emit a signal spontaneously, such as when the detectable label is a radionuclide. In other cases the imaging agent emits a signal as a result of being stimulated by an external field such as when the imaging agent is a relaxivity metal. Examples of signals include, without limitation, gamma rays, X-rays, visible light, infrared energy, and radiowaves. Non-limiting examples of modalities of imaging may include magnetic resonance imaging (MRI), ultrasound (US), computed tomography (CT), Positron Emission Tomography (PET), Single Photon Emission Computed Tomography (SPECT), and optical imaging (01, bioluminescence and fluorescence).

The compound of the invention optionally includes one or more treatment agents, such as a drug or hormone. In certain embodiments, a compound of the invention comprises an imaging agent and a treatment agent. In other embodiments, a compound of the invention comprises a carbocyanine dye or derivative thereof and a treatment agent. As will be appreciated by the skilled artisan, the choice of a particular treatment agent can and will vary depending upon the indication to be treated and its stage of progression. Because the compounds of the invention are selectively targeted to cells that express integrins, the treatment agents are generally directed toward treatment of an intregrin-mediated disorder such as diabetes, inflammation, cardiovascular disease, and cancer. For example, when the indication is diabetes, the treatment agent may be sulfonylureas, biguanides, thiazolidinediones, meglitinides, D-phenylalanine derivatives, amylin synthetic derivatives, and incretin mimetics. In a further embodiment, when the indication is inflammation, the treatment agent may be an NSAID such as aniline derivatives (acetaminophen), indole-3-acetic acid derivatives (indomethacin), specific Cox-2 inhibitors (Celebrex), and aspirin. By way of further example, when the indication is cardiovascular disease, the treatment agent may include sodium-channel blockers (e.g., quinidine), beta-blockers (e.g., propranolol), calcium-channel blockers (e.g., diltiazen), diuretics (e.g., hydrochlorothiazide), ACE inhibitors (e.g., captopril), and thrombolytic agents (e.g., tissue plasminogen activator and streptokinase). In an additional embodiment when the indication is cancer, the treatment agent may include DNA synthesis inhibitors (e.g., daunorubicin, and adriamycin), mitotic inhibitors (e.g., the taxanes, paclitaxel, and docetaxel), the vinca alkaloids (e.g., vinblastine, vincristine, and vinorelbine), antimetabolites (e.g., 5-fluorouracil, capecitabine, 6-mercaptopurine, methotrexate, gemcitabine, cytarabine (ara-C), fludarabine, pemetrexed, cytosine arabinoside, methotrexate, and aminopterin), alkylating agents (e.g., busulfan, cisplatin, carboplatin, chlorambucil, cyclophosphamide, ifosfamide, dacarbazine (DTIC), mechlorethamine (nitrogen mustard), melphalan, and temozolomide), nitrosoureas (e.g., carmustine (BCNU) and lomustine (CCNU) anthracyclines (e.g., daunorubicin, doxorubicin (Adriamycin), epirubicin, idarubicin, and mitoxantrone), topoisomerase inhibitors (e.g., topotecan, irinotecan, etoposide (VP-16), and teniposide), cytotoxins (e.g., paclitaxel, vinblastine, and macromycin), anti-cytoskeletals (e.g., taxol and cholchicine) and angiogenesis inhibitors (e.g., VEGF inhibitors, anti-VEGF Abs). Summaries of cancer drugs, including information regarding approved indications, may be found via the National Cancer Institute at the National Institutes of Health, the FDA Approved Drug Product database and the National Comprehensive Cancer Network (NCCN) guidelines. In a specific embodiment, a treatment agent may be a chemotherapeutic. In another specific embodiment, a treatment agent may be a chemotherapeutic for pancreatic cancer. Other suitable treatment agents may include hormones (e.g., steroids), antibodies, antibody fragments, peptides, glycopeptides, peptidomimetic, drug mimic, metal chelating agents, radioactive agents, echogenic agents, various drugs (in addition to the ones specifically delineated), antisense molecules, and small inhibitory RNAs.

(c) Linkers

In certain embodiments, the imaging agent and/or treatment agent is conjugated to the linear peptide via one or more linkers. In other embodiments having more than one linear peptide or one or more cyclic peptides, the individual peptides may optionally be conjugated via one or more linkers.

A variety of linkers are suitable in the present invention, but typically the linker will impart a degree of flexibility to the compound of the invention. Generally speaking, the chain of atoms defining the linker can and will vary depending upon the embodiment. In certain embodiment, the linker will comprise one or more amino acids. Amino acid residue linkers are usually at least one residue and can be 50 or more residues. In an embodiment, a linker may be about 1 to about 10 amino acids. In another embodiment, a linker may be about 10 to about 20 amino acids. In still another embodiment, a linker may be about 20 to about 30 amino acids. In still yet another embodiment, a linker may be about 30 to about 40 amino acids. In different embodiments, a linker may be about 40 to about 50 amino acids. In other embodiments, a linker may be more than 50 amino acids. For instance, a linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. In a specific embodiment, a linker is 1 amino acid.

Any amino acid residue may be used for the linker. Typical amino acid residues used for linking are glycine, serine, alanine, leucine, lysine, glutamic and aspartic acid, or the like. For example, a linker may be $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. Accordingly, n may be 1, 2, 3, 4, 5, 6, 7, 8, 9, 10, 11, 12, 13, 14, 15, 16, 17, 18, 19 or 20. Thus, in certain embodiments, a linker includes, but is not limited to, $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. In a specific embodiment, a linker is one glycine.

In a further embodiment, the linker will comprise hydrocarbyl or substituted hydrocarbyl groups. In a typical alternative of this embodiment, the linker is from about 1 to about 50 atoms in length. Alternatively, the linker is from about 2 about 30 atoms in length. In an embodiment, the linker is from about 4 to about 20 atoms in length. The linker may comprise a variety of heteroatoms that may be saturated or unsaturated, substituted or unsubstituted, linear or cyclic, or straight or branched. The chain of atoms defining the linker will typically be selected from the group consisting of carbon, oxygen, nitrogen, sulfur, selenium, silicon and phosphorous. In an alternative embodiment, the chain of atoms is selected from the group consisting of carbon, oxygen, nitrogen, sulfur and selenium. In an embodiment, the linker will comprise substantially carbon and oxygen atoms. In addition, the chain of atoms defining the linker may be substituted or unsubstituted with atoms other than hydrogen, including, but not limited to, hydroxy, keto (=O), or acyl, such as acetyl. Thus, the chain may optionally include one or more ether, thioether, selenoether, amide, or amine linkages between hydrocarbyl or substituted hydrocarbyl regions. Exemplary linkers include ethylene glycol and aminohexanoic acid. More specifically, a linker may be a polyethylene glycol linker. Such a linker may be referred to as a heterobifunctional PEG linker or a homobifunctional PEG linker.

In certain embodiments, a linker further comprises one or more spacers. Spacers are known in the art. Non-limiting examples of spacers include 2-aminoethoxy-2-ethoxy acetic acid (AEEA) linkers, AEEEA linkers, and AEA linkers. In a specific embodiment, a linker further comprises one or more 2-aminoethoxy-2-ethoxy acetic acid (AEEA) linkers.

(d) Exemplary Compounds of the Invention

In one exemplary embodiment, the compound will have the characteristics detailed above and will be defined by formula (I):

wherein:
R$^1$ is an imaging agent;
R$^2$ is independently selected from the group consisting of a treatment agent, hydrogen, hydroxyl, NH$_2$, hydrocarbyl, and substituted hydrocarbyl;
X$^1$ and X$^2$ are independently selected from any amino acid residue;
X$^1_m$—R-D-X$^2_p$ together form a linear or cyclic peptide;
m is an integer from 1 to about 10;

n is an integer from 1 to about 10;
p is an integer from 1 to about 10; and
a dash (-) represent a covalent bond.

In an alternative embodiment, the compound will have formula (I) wherein:
n is from 1 to 5;
m is from 1 to 3;
p is from 1 to 3; and
$X^1$ and $X^2$ are selected from the group consisting of C, G, S, P, C, N, Q, D, E, K, R, T and H.

In a specific embodiment, $X^1$ is CG; m is 1; $X^2$ is SPC; p is 1; and n is 1. In another specific embodiment, the C of $X^1$ is D-cysteine and/or the C of $X^2$ is D-cysteine. In still another specific embodiment, the Y is D-tyrosine.

In certain embodiments, a cyclic peptide is [CGRDSPC] (SEQ ID NO:24), wherein the two cysteines cyclize the peptide by forming a disulfide bridge. The cysteines are both L-cysteine, both D-cysteine, or one is L-cysteine and one is D-cysteine. In other embodiments, one or more amino acid residues are inserted prior to or after the Y. In a specific embodiment, an amino acid residue is inserted after Y. In another specific embodiment, a Lys (K) is inserted after the Y.

In certain embodiments, the Y is halogenated. Halogens include fluorine, chlorine, bromine, iodine, and astatine. More specifically, the halogen is a radioisotope selected from the group consisting of $^{18}$F, $^{75}$Br, $^{77}$Br, $^{122}$I, $^{123}$I, $^{124}$I, $^{125}$I, $^{129}$I, $^{131}$I, and $^{211}$At.

In an exemplary embodiment, $[X^1_m\text{—R-D-}X^2_p]_n\text{—Y}$ is selected from the group consisting of:

| SEQ ID NO: | $[X^1_m\text{-R-D-}X^2_p]_n Y$ |
|---|---|
| 8 | [$_D$Cys-Gly-Arg-Asp-Ser-Pro-Cys]-Lys-Tyr |
| 9 | [$_D$Cys-Gly-Arg-Asp-Ser-Pro-Cys]-Tyr |
| 10 | [$_D$Cys-Gly-Arg-Asp-Ser-Pro-Cys]-Tyr-Lys |
| 11 | [$_D$Cys-Gly-Arg-Asp-Ser-Pro-$_D$Cys]-Tyr |
| 12 | [Cys-Gly-Arg-Asp-Ser-Pro-Cys]-Tyr |
| 17 | Gly-[$_D$Cys-Gly-Arg-Asp-Ser-Pro-Cys]-Tyr |
| 18 | Gly-[$_D$Cys-Gly-Arg-Asp-Ser-Pro-Cys]-$_D$Tyr |
| 19 | Gly-[$_D$Cys-Gly-Arg-Asp-Ser-Pro-Cys]-$_D$Tyr-Lys |
| 20 | Gly-[Cys-Gly-Arg-Asp-Ser-Pro-Cys]-$_D$Tyr-Lys |
| 21 | Gly-[$_D$Cys-Gly-Arg-Asp-Ser-Pro-$_D$Cys]-Tyr |
| 22 | Gly-[Cys-Gly-Arg-Asp-Ser-Pro-$_D$Cys]-Tyr |
| 23 | Gly-[$_D$Cys-Gly-Arg-Asp-Ser-Pro-$_D$Cys]-$_D$Tyr |

In certain embodiments, $R^2$ is selected from the group consisting of hydroxyl and $NH_2$. In a specific embodiment, $R^2$ is hydroxyl.

In an embodiment, $R^1$ is a carbocyanine dye or a derivative thereof. In another embodiment, $R^1$ is selected from the group consisting of Cypate (cypate 4), LS288, LS798, LS276, LS843, Cypate 3, and Cypate 2. In a specific embodiment, a derivative of a carbocyanine dye comprises an alkyne, azido ($N_3$), or a chelating agent. In still another specific embodiment, a derivative of a carbocyanine dye comprises a nanoparticle, a small organic molecule, a peptide, an organometallic, a metal chelate, a protein, a drug, an antibiotic, or a carbohydrate.

In each embodiment for compounds having formula (I), the compound may optionally comprise a linker, $L^1$, that conjugates $R^1$ to $X^1$. The compound may additionally comprise a linker, $L^2$, that conjugates $R^2$ to Y. In addition, the compound may additionally comprise a linker, $L^3$, that conjugates $R^1$ to $X^2$. The compound may additionally comprise a linker, $L^4$, that conjugates $R^2$ to $X^1$. The compound may additionally comprise a linker, $L^5$, that conjugates $X^1$ to $X^2$. Furthermore, the compound may additionally comprise a linker, $L^6$, that conjugates $R^1$ to $R^2$. In a specific embodiment, $L^1$ is glycine. In another specific embodiment, $L^1$ is polyethylene glycol.

In another exemplary embodiment, the compound will have the characteristics detailed above and will be defined by formula (II):

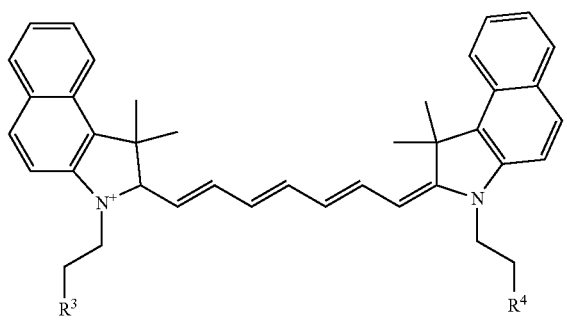

(II)

wherein:
$R^3$ is selected from the group consisting of nanoparticles, small organic molecules, peptides, organometallics, metal chelates, proteins, drugs, antibiotics, and carbohydrates; and
$R^4$ is $[X^1_m\text{—R-D-}X^2_p]_n\text{—}R^2$, wherein:
$R^2$ is independently selected from the group consisting of a hydrogen, hydroxyl, $NH_2$, hydrocarbyl, and substituted hydrocarbyl;
$X^1$ and $X^2$ are independently selected from any amino acid residue;
$X^1_m\text{—R-D-}X^2_p$ together form a linear or cyclic peptide;
m is an integer from 1 to about 10;
n is an integer from 1 to about 10;
p is an integer from 1 to about 10; and
a dash (-) represent a covalent bond.

In an alternative embodiment, the compound will have formula (II) wherein:
n is from 1 to 5;
m is from 1 to 3;
p is from 1 to 3; and
$X^1$ and $X^2$ are selected from the group consisting of C, G, S, P, C, N, Q, D, E, K, R, T and H.

In a specific embodiment, $X^1$ is CG; m is 1; $X^2$ is SPC; p is 1; and n is 1. In another specific embodiment, the C of $X^1$ is D-cysteine and/or the C of $X^2$ is D-cysteine. In still another specific embodiment, the Y is D-tyrosine.

In certain embodiments, a cyclic peptide is [CGRDSPC] (SEQ ID NO:24), wherein the two cysteines cyclize the peptide by forming a disulfide bridge. The cysteines are both L-cysteine, both D-cysteine, or one is L-cysteine and one is D-cysteine. In other embodiments, one or more amino acid residues are inserted prior to or after the Y. In a specific embodiment, an amino acid residue is inserted after Y. In another specific embodiment, a Lys (K) is inserted after the Y.

In certain embodiments, the Y is halogenated. Halogens include fluorine, chlorine, bromine, iodine, and astatine. More specifically, the halogen is a radioisotope selected from the group consisting of $^{18}$F, $^{75}$Br, $^{77}$Br, $^{122}$I, $^{123}$I, $^{124}$I, $^{125}$I, $^{129}$I, $^{131}$I, and $^{211}$At.

In an exemplary embodiment, $[X^1{}_m\text{—R-D-}X^2{}_p]_n$—Y is selected from the group consisting of:

| SEQ ID NO: | $[X^1{}_m\text{-R-D-}X^2{}_p]_n$Y |
|---|---|
| 8 | [$_D$Cys-Gly-Arg-Asp-Ser-Pro-Cys]-Lys-Tyr |
| 9 | [$_D$Cys-Gly-Arg-Asp-Ser-Pro-Cys]-Tyr |
| 10 | [$_D$Cys-Gly-Arg-Asp-Ser-Pro-Cys]-Tyr-Lys |
| 11 | [$_D$Cys-Gly-Arg-Asp-Ser-Pro-$_D$Cys]-Tyr |
| 12 | [Cys-Gly-Arg-Asp-Ser-Pro-Cys]-Tyr |
| 17 | Gly-[$_D$Cys-Gly-Arg-Asp-Ser-Pro-Cys]-Tyr |
| 18 | Gly-[$_D$Cys-Gly-Arg-Asp-Ser-Pro-Cys]-$_D$Tyr |
| 19 | Gly-[$_D$Cys-Gly-Arg-Asp-Ser-Pro-Cys]-$_D$Tyr-Lys |
| 20 | Gly-[Cys-Gly-Arg-Asp-Ser-Pro-Cys]-$_D$Tyr-Lys |
| 21 | Gly-[$_D$Cys-Gly-Arg-Asp-Ser-Pro-$_D$Cys]-Tyr |
| 22 | Gly-[Cys-Gly-Arg-Asp-Ser-Pro-$_D$Cys]-Tyr |
| 23 | Gly-[$_D$Cys-Gly-Arg-Asp-Ser-Pro-$_D$Cys]-$_D$Tyr |

In certain embodiments, $R^2$ is selected from the group consisting of hydroxyl and $NH_2$. In a specific embodiment, $R^2$ is hydroxyl.

In other embodiments, the compound will have the characteristics detailed above and will be defined by formula (II):

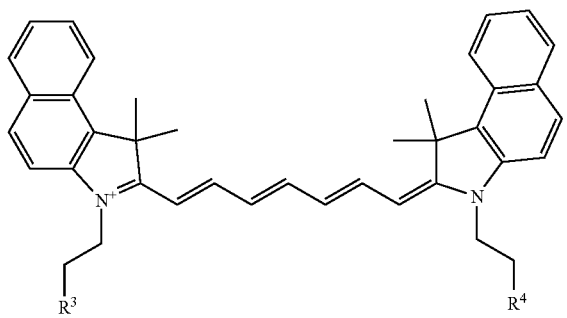

(II)

wherein:
$R^3$ is selected from the group consisting of nanoparticles, small organic molecules, peptides, organometallics, metal chelates, proteins, drugs, antibiotics, and carbohydrates; and
$R^4$ is selected from the group consisting of:

| SEQ ID NO: | $R^4$ |
|---|---|
| 8 | CONH-[$_D$Cys-Gly-Arg-Asp-Ser-Pro-Cys]-Lys-Tyr-OH |
| 9 | CONH-[$_D$Cys-Gly-Arg-Asp-Ser-Pro-Cys]-Tyr-OH |
| 10 | CONH-[$_D$Cys-Gly-Arg-Asp-Ser-Pro-Cys]-Tyr-Lys-OH |
| 11 | CONH-[$_D$Cys-Gly-Arg-Asp-Ser-Pro-$_D$Cys]-Tyr-OH |
| 12 | CONH-[Cys-Gly-Arg-Asp-Ser-Pro-Cys]-Tyr-OH |
| 13 | CONH-[Cys-Arg-Gly-Asp-Ser-Pro-Cys]-Tyr-OH |
| 14 | CONH-[$_D$Cys-Arg-Gly-Asp-Ser-Pro-Cys]-Tyr-OH |
| 15 | CONH-[$_D$Cys-Arg-Gly-Asp-Ser-Pro-$_D$Cys]-Tyr-OH |
| 17 | CONH-Gly-[$_D$Cys-Gly-Arg-Asp-Ser-Pro-Cys]-Tyr-OH |
| 18 | CONH-Gly-[$_D$Cys-Gly-Arg-Asp-Ser-Pro-Cys]-$_D$Tyr-OH |
| 19 | CONH-Gly-[$_D$Cys-Gly-Arg-Asp-Ser-Pro-Cys]-$_D$Tyr-Lys-OH |
| 20 | CONH-Gly-[Cys-Gly-Arg-Asp-Ser-Pro-Cys]-$_D$Tyr-Lys-OH |
| 21 | CONH-Gly-[$_D$Cys-Gly-Arg-Asp-Ser-Pro-$_D$Cys]-Tyr-OH |
| 22 | CONH-Gly-[Cys-Gly-Arg-Asp-Ser-Pro-$_D$Cys]-Tyr-OH |
| 23 | CONH-Gly-[$_D$Cys-Gly-Arg-Asp-Ser-Pro-$_D$Cys]-$_D$Tyr-OH |

In certain embodiments, the Y is halogenated. Halogens include fluorine, chlorine, bromine, iodine, and astatine. More specifically, the halogen is a radioisotope selected from the group consisting of $^{18}$F, $^{75}$Br, $^{77}$Br, $^{122}$I, $^{123}$I, $^{124}$I, $^{125}$I, $^{129}$I, $^{131}$I, and $^{211}$At.

Alternatively, for each embodiment for compounds having formula (I) or formula (II), the compound may optionally comprise at least one cyclic peptide having a RGD motif. Generally, the cyclic peptide has from about 4 amino acid residues to about 10 amino acid residues. In one embodiment, the cyclic peptide has 5 amino acid residues. In this embodiment, 3 of the amino acid residues will be the RGD motif and the other two amino acid residues may be selected from any amino acid residue detailed above. In an alternative embodiment, the cyclic peptide has 6 amino acid residues. In this embodiment, 3 of the amino acid residues will be the RGD motif and the other three may be selected from any amino acid residue detailed above.

In a further exemplary embodiment, the compound will have the characteristics detailed above and will be defined by formula (II):

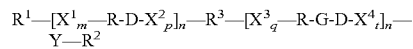

wherein:
$R^1$ is an imaging agent;
$R^2$ is independently selected from the group consisting of a treatment agent, hydrogen, hydroxyl, $NH_2$, hydrocarbyl, and substituted hydrocarbyl;
$R^3$ is a covalent bond or a linker;
$X^1$, $X^2$, $X^3$ and $X^4$ are independently selected from any amino acid residue;
$X^1{}_m$—R-D-$X^2{}_p$ together form a linear or cyclic peptide;
$X^3{}_q$—R-G-D-$X^4{}_t$ together form a cyclic peptide;

m is an integer from 1 to about 10;
n is an integer from 1 to about 10;
p is an integer from 1 to about 10;
q is an integer from about 1 to 5;
s is an integer from about 1 to 10;
t is an integer from about 1 to 5; and
a dash (-) represent a covalent bond.

In an alternative embodiment, the compound will have formula (II) wherein:
n is from 1 to 3;
m is from 1 to 3;
p is from 1 to 3;
q is 2 or 3;
s is from 1 to 3;
t is 2 or 3;
$X^1$ and $X^2$ are selected from the group consisting of G, S, N, Q, D, E, K, R, T, Y, C, P and H; and
$X^3$ and $X^4$ are selected from any amino acid residue.

In each embodiment for compounds having formula (II), the compound may optionally comprise a linker, $L^1$, that conjugates $R^1$ to $X^1$. In addition, the compound may additionally comprise a linker, $L^2$, that conjugates $R^2$ to Y.

Other exemplary compounds of the invention are illustrated in the Examples.

In addition, the compound(s) of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the compound(s) of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc and organic salts made from N, N'-dibenzylethylenediamine, chloroprocaine, choline, diethanolamine, ethylenediamine, meglumine-(N-methylglucamine) and procaine.

As will be appreciated by a skilled artisan, the compound(s) of the present invention can be administered by a number of different means that will deliver an effective dose for either detection or treatment purposes. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

II. Methods

The present invention encompasses a method for detecting, monitoring and/or treatment or prevention of a variety of integrin-mediated disorders in a subject. Specifically, the present invention encompasses a method for detecting a variety of integrin-mediated disorders in a subject.

In an aspect, the present invention encompasses a method for detecting expression of a β3 subunit of integrin in a cell. The method comprises contacting a population of cells with a compound of the invention and detecting the presence of a signal emitted from the imaging agent of the compound of the invention in the population of cells, the signal being emitted from a cell expressing a β3 subunit of integrin.

In another aspect, the present invention encompasses a method for detecting, monitoring and/or treatment or prevention of cancer. The method comprises administering an effective amount of a composition comprising a compound of the invention to a subject; and detecting the presence of a signal emitted from the imaging agent of the compound of the invention in the subject, wherein detection of signal above baseline indicates cancer. In a specific embodiment, the present invention encompasses a method for detecting cancer in a subject.

In still another aspect, the present invention encompasses a method for detecting, monitoring and/or treatment or prevention of pancreatic cancer. The method comprises administering an effective amount of a composition comprising a compound of the invention to a subject; and detecting the presence of a signal emitted from the imaging agent of the compound of the invention in the subject, wherein detection of signal above baseline indicates pancreatic cancer. In a specific embodiment, the present invention encompasses a method for detecting pancreatic cancer in a subject.

In still yet another aspect, the present invention encompasses a method for detecting, monitoring and/or treatment or prevention of early stage pancreatic ductal adenocarcinoma (PDAC) and precursor pancreatic intraepithelial neoplasia (PanIN). The method comprises administering an effective amount of a composition comprising a compound of the invention to a subject; and detecting the presence of a signal emitted from the imaging agent of the compound of the invention in the subject, wherein detection of signal above baseline indicates early stage pancreatic ductal adenocarcinoma (PDAC) or pancreatic intraepithelial neoplasia (PanIN). In a specific embodiment, the present invention encompasses a method for detecting early stage pancreatic ductal adenocarcinoma (PDAC) and precursor pancreatic intraepithelial neoplasia (PanIN).

In yet still another aspect, the present invention encompasses a method for differentiating pancreatic ductal adenocarcinoma (PDAC) and precursor pancreatic intraepithelial neoplasia (PanIN) from pancreatitis. The method comprises administering an effective amount of a composition comprising a compound of the invention to a subject; and detecting the presence of a signal emitted from the imaging agent of the compound of the invention in the subject, wherein detection of signal above baseline indicates PDAC or PanIN and detection of a signal at or below baseline indicates pancreatitis.

In yet still another aspect, the present invention encompasses a method for differentiating pancreatic ductal adenocarcinoma (PDAC) and PanIN-3 from PanIN-1/2 and ductal hyperplasia/metaplasia. The method comprises administering an effective amount of a composition comprising a compound of the invention to a subject; and detecting the presence of a signal emitted from the imaging agent of the compound of the invention in the subject, wherein detection of signal above baseline indicates PDAC or PanIN-3 and detection of a signal at or below baseline indicates PanIN-1/2 or ductal hyperplasia/metaplasia.

In a different aspect, the present invention encompasses a method for detecting and/or monitoring circulating tumor cells (CTCs). The method comprises administering an effective amount of a composition comprising a compound of the invention to a subject; and detecting the presence of a signal emitted from the imaging agent of the compound of the invention in the subject, wherein detection of signal above baseline indicates the presence of CTCs. In a specific embodiment, the present invention encompasses a method for detecting CTCs in a subject.

By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

Suitable subjects include, but are not limited to, a human, a livestock animal, a companion animal, a lab animal, and a zoological animal. A subject may or may not be known to have a tumor. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

The methods of the invention may be used to detect, monitor, treat or prevent a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a specific embodiment, the neoplasm or cancer is pancreatic cancer.

The invention comprises, in part, imaging a subject. Non-limiting examples of modalities of imaging may include magnetic resonance imaging (MRI), ultrasound (US), computed tomography (CT), Positron Emission Tomography (PET), Single Photon Emission Computed Tomography (SPECT), and optical imaging (OI, bioluminescence and fluorescence). Radioactive molecular probes are traditionally imaged with PET, SPECT or gamma (γ) cameras, by taking advantage of the capability of these imaging modalities to detect the high energetic γ rays. In contrast, OI generally detects low energy lights (visible or near-infrared lights) emitted from bioluminescence or fluorescence probes.

As used herein, "baseline" may be the background signal. Alternatively, baseline may be no signal. In a specific embodiment, baseline is the signal detected in uninvolved tissue. A skilled artisan would be able to determine the baseline of a signal. By above is meant that the signal is greater than the baseline signal. For example, the signal may be at least 2% greater than baseline. For example, the signal may be at least 2%, at least 5%, at least 10%, at least 20%, at least 30%, at least 40%, at least 50%, at least 60%, at least 70%, at least 80%, at least 90%, or at least 100% greater than baseline. In a specific embodiment, the signal is >20% above baseline. In other embodiments, the signal may be increased at least 2-fold over baseline. For example, the signal may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold over baseline.

The term "signal" as used herein, refers to a signal derived from an imaging agent that can be detected and quantitated with regards to its frequency and/or amplitude. The signal may be an optical signal. The signal can be generated from one or more imaging agents of the present disclosure. In an embodiment, the signal may need to be the sum of each of the individual signals. In an embodiment, the signal can be generated from a summation, an integration, or other mathematical process, formula, or algorithm, where the signal is from one or more imaging agent. In an embodiment, the summation, the integration, or other mathematical process, formula, or algorithm can be used to generate the signal so that the signal can be distinguished from background noise and the like. It should be noted that signals other than the signal of interest can be processed and/or obtained in a similar manner as that of the signal of interest.

Using a method of the invention, microscopic lesions of cancer may be detected in a subject. Such lesions are generally not visible with current imaging techniques. Further the compounds of the disclosure may be used to guide needle biopsy, assess surgical margins, and detect occult metastatic disease in real time.

In certain aspects, a pharmacologically effective amount of a compound of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the compounds useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the peptide being labeled, the imaging agent, labeling methods, the method of imaging and parameters related thereto, metabolism of the labeled drug in the subject, the stability of the label (e.g. the half-life of a radionuclide label), the time elapsed following administration of the compound prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount. A detectable amount may be visible from about 1 to about 120 hours or more. For example, a detectable amount may be visible from about 1 to about 110 hours, or from about 1 to about 100 hours. Accordingly, a detectable amount may be visible at about 1, about 2, about 3, about 4, about 5, about 6, about 7, about 8, about 9, about 10, about 11, about 12, about 16, about 24, about 36, about 48, about 60, about 72, about 84, about 96, about 108, or about 120 hours.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of peptide constructs, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

In certain aspects, the methods of the invention may further comprise administering therapeutic agents not conjugated to a compound of the invention for neoplasms and cancer. Suitable therapeutic agents for neoplasms and cancers are known in the art, and will depend upon the type and stage of cancer. Summaries of cancer drugs, including information regarding approved indications, may be found via the National Cancer Institute at the National Institutes of Health (www.cancer.gov/cancertopics/druginfo/alphalist)

and the FDA Approved Drug Product database (accessdata.fda.gov/scripts/cder/drugsatfda/).

Definitions

The term "detect" as used herein refers to diagnostic procedures and methods to image the compounds of the invention. These procedures include, but are not limited to, optical tomography, fluorescence endoscopy, imaging detection or measurement of or by fluorescence and imaging absorption, light scattering, acoustic, sonographic, magnetic resonance, or radiation means.

The term "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "localized therapy" is a procedure for administering a compound of the invention directly into pathological tissue. Treatment in localized therapy may be accomplished by photo-, chemical-, or biological activation of the compound of the invention. Photoactivation may be conducted with light within a specific wavelength range. Chemical activation may be induced cytotoxicity. Biological activation may be initiated by physiological and molecular processes, including enzymatic activation of the compound.

The term "monitoring" as used herein refers to the continued or intermittent detection and may be combined with treatment for purposes including, but not limited to, ascertaining the progress or mechanism of pathology and efficacy of a particular treatment regime.

The term "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "treat" or "treatment" includes partial or total inhibition of the progression of a particular disorder. For example when the disorder is cancer, treatment include partial or total inhibition of neoplasia growth, spreading or metastasis, as well as partial or total destruction of the neoplasia cells. Treatment also includes prevention of a neoplasia or related disorder. By way of further example when the disorder is inflammation, the term "treat" also includes partial or total inhibition of inflammation or an inflammation related disorder. Treatment also includes prevention of an inflammation or inflammation related disorder.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Improved RD Targeting Compounds

Figure 5:
FIG. 5 depicts images showing LS838 for fluorescence and nuclear (PET and or SPECT) imaging. 4T1 luc in Balb/c; 100 µl of 50 µM LS838.
Figure 6:
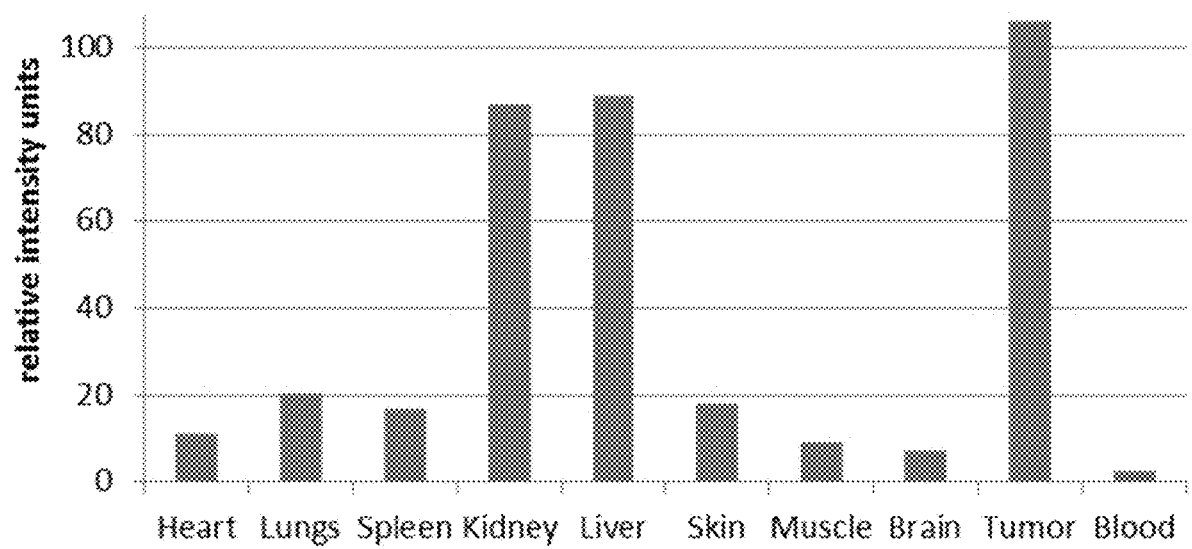
FIG. 6 depicts the distribution of LS838 in tissue at 24 hours.

Compare the Performance of the Different Sequences:

A variety of probes which have similar sequence compared to LS301 were designed and prepared (Table 1). The probes have different peptide sequences, D-, L-amino acid variations or different groups on C-terminus. The sequences of the probes were tested by LC-MS and the spectroscopy properties were recorded. The performances of the tumor targeting abilities were also tested in vivo. We discovered LS838 (FIG. 1) has better brightness after accumulation inside the cancer tumors and the targeting performance is similar to LS301. It was unexpected that LS838 would be brighter relative to LS301 and it is unknown to us why it does. However, the enhanced brightness allows the use of smaller amounts of material to achieve the same uptake kinetics and accumulation as LS301. FIG. 5 depicts the accumulation of LS838 in vivo and FIG. 6 graphically quantifies the intensity of LS838 in various organs. LS838 precisely accumulates in the tumor at 24 hours. LS838 labeled can be labeled with radionuclides such as radioiodine, bromine, or fluorine for combined optical and nuclear imaging. The labeling does not alter the excellent tumor localizing properties. Notably, in vivo administration of LS747 and LS758, both of which have a Tyr adjacent to the cypate, led to rapid loss of retention in tumors. These results suggest that the position of the Tyr residue is important.

TABLE 1

Compounds prepared for performance comparison with LS301 peptide

| No. | Sequence | SEQ ID NO |
|---|---|---|
| LS301 | Cypate-Cyclo($_D$Cys-Gly-Arg-Asp-Ser-Pro-Cys)-Lys-OH | 1 |
| LS651 | Cypate-Cyclo($_D$Cys-Gly-Arg-Asp-Ser-Pro-$_D$Cys)-Lys-OH | 2 |
| LS652 | Cypate-Cyclo(Cys-Gly-Arg-Asp-Ser-Pro-Cys)-Lys-OH | 3 |
| LS653 | Cypate-Cyclo(Cys-Arg-Gly-Asp-Ser-Pro-Cys)-Lys-OH | 4 |
| LS654 | Cypate-Cyclo($_D$Cys-Arg-Gly-Asp-Ser-Pro-Cys)-Lys-OH | 5 |

TABLE 1-continued

Compounds prepared for performance comparison with LS301 peptide

| No. | Sequence | SEQ ID NO |
|---|---|---|
| LS655 | Cypate-Cyclo($_D$Cys-Arg-Gly-Asp-Ser-Pro-$_D$Cys)-Lys-OH | 6 |
| LS747 | Cypate-Tyr-Cyclo($_D$Cys-Gly-Arg-Asp-Ser-Pro-Cys)-Lys-OH | 7 |
| LS748 | Cypate-Cyclo($_D$Cys-Gly-Arg-Asp-Ser-Pro-Cys)-Lys-Tyr-OH | 8 |
| LS758 | Tyr-Cypate-Cyclo($_D$Cys-Gly-Arg-Asp-Ser-Pro-Cys)-Lys-NH$_2$ | 1 |
| LS837 | Cypate-Cyclo($_D$Cys-Gly-Arg-Asp-Ser-Pro-Cys)-Lys-NH$_2$ | 1 |
| LS838 | Cypate-Cyclo($_D$Cys-Gly-Arg-Asp-Ser-Pro-Cys)-Tyr-OH | 9 |
| LS839 | Cypate-Cyclo($_D$Cys-Gly-Arg-Asp-Ser-Pro-Cys)-Tyr-Lys-OH | 10 |
| LS839-2 | Cypate-Cyclo($_D$Cys-Gly-Arg-Asp-Ser-Pro-Cys)-Lys-Tyr-NH$_2$ | 8 |

Compare the Performance of the LS301 Derivative with Fluorophores with Different Hydrophobicity:

LS301 derivatives with fluorophores with different hydrophobicity were prepared to test if the hydrophobicity of the dye on the same peptide sequence will affect the targeting performance. Four of the NIR dyes with different hydrophobicity (FIG. 2) beside cypate were attached to the same GRD peptide (Table 2). These probes were tested in vivo to compare with LS301.

TABLE 2

Compounds prepared with fluorophores with different hydrophobicity

| No. | Sequence | SEQ ID NO |
|---|---|---|
| LS636 | LS288-Cyclo($_D$Cys-Gly-Arg-Asp-Ser-Pro-Cys)-Lys-OH | 1 |
| LS840 | LS798-Cyclo($_D$Cys-Gly-Arg-Asp-Ser-Pro-Cys)-Lys-OH | 1 |
| LS841 | LS276-Cyclo($_D$Cys-Gly-Arg-Asp-Ser-Pro-Cys)-Lys-OH | 1 |
| LS844 | LS843-Cyclo($_D$Cys-Gly-Arg-Asp-Ser-Pro-Cys)-Lys-OH | 1 |

Figure 4A:
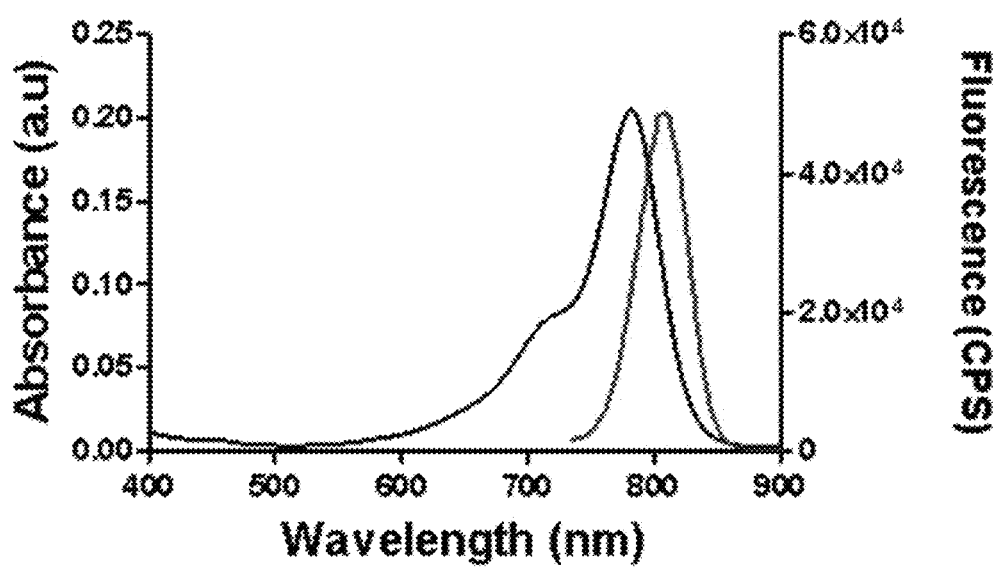
FIG. 4A, FIG. 4B and FIG. 4C depict the absorption and emission spectra of cypates.
Figure 4B:
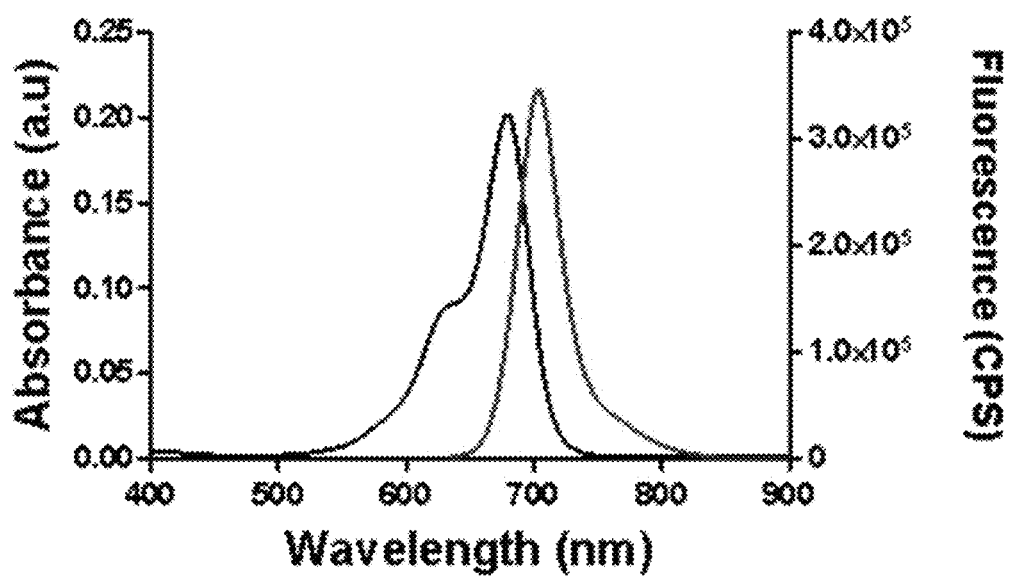
Figure 4C:
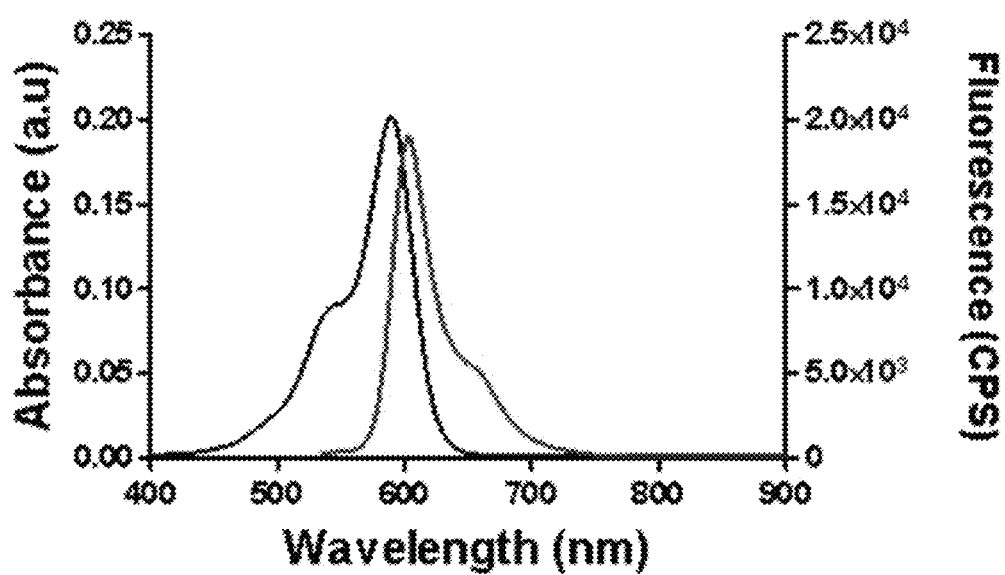

Multicolor LS301 Derivatives for Non-Invasive Molecular Imaging:

LS301 derivatives were prepared with different cyanine dyes (cypate 3 and cypate 2, FIG. 3 and FIG. 4) which have emission wavelength (Table 3). These probes were tested in vivo and will allow the use of different wavelengths for the optical imaging.

TABLE 3

Compounds prepared with cyanine dyes with different emission wavelength

| No. | Sequence | SEQ ID NO |
|---|---|---|
| LS789 | Cypate 3-Cyclo($_D$Cys-Gly-Arg-Asp-Ser-Pro-Cys)-Lys-OH | 1 |
| LS858 | Cypate 2-Cyclo($_D$Cys-Gly-Arg-Asp-Ser-Pro-Cys)-Lys-OH | 1 |

Figure 13:
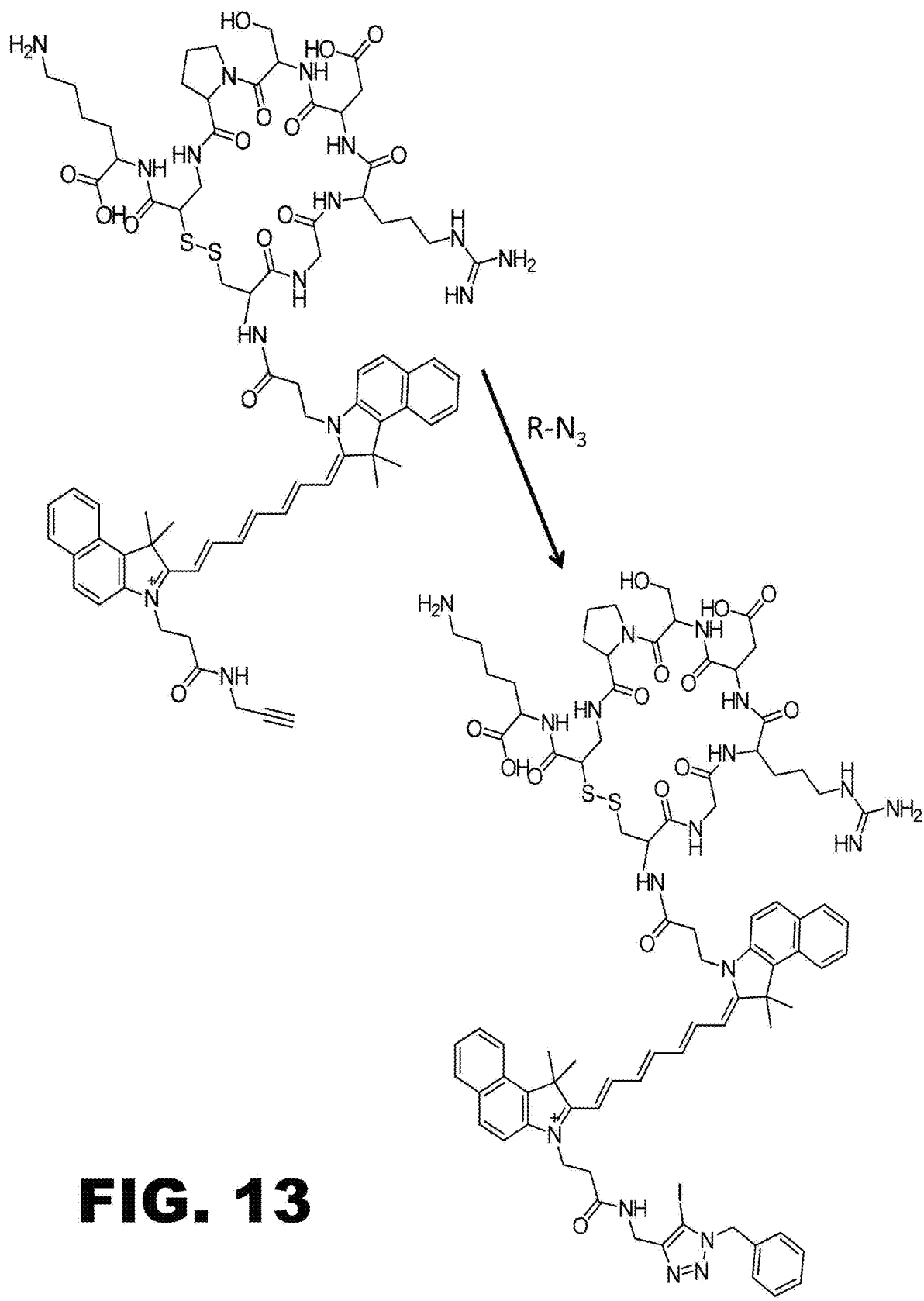
FIG. 13 depicts further derivatization of compounds for drug delivery. The alkyne group can react with any azido group selectively. We envisage using this molecular as a versatile reagent to incorporate drugs and other biologically active molecules. The method can also be used to introduce stable radio-halogens.

Multimodality LS301 Derivatives for Non-Invasive Molecular Imaging:

A variety of the multimodality LS301 derivatives readily available for radio-isotope labeling were designed and prepared (Table 4). These probes can be used for nuclear-imaging with the superior performance of targeted optical imaging, providing versatile application in different type of cancer diseases. The cold labeled probes were prepared and tested in vivo to compare with LS301. FIG. 13 provides an example of derivatization of the cypate for incorporation of drugs, biologically active molecules and/or radio-halogens.

TABLE 4

Compounds prepared for multimodal imaging.

| No. | Compound | Structures | SEQ ID NO |
|---|---|---|---|
| LS838 | | Cypate-Cyclo($_D$Cys-Gly-Arg-Asp-Ser-Pro-Cys)-Tyr-OH | 9 |
| LS848 | alkyne-LS301 | alkyne-Cypate-Cyclo($_D$Cys-Gly-Arg-Asp-Ser-Pro-Cys)-Lys-OH | 1 |
| LS859 | Azido-LS301 | N3-Cypate-Cyclo($_D$Cys-Gly-Arg-Asp-Ser-Pro-Cys)-Lys-OH | 1 |
| LS861 | DTPA-LS301 | DTPA-Cypate-Cyclo($_D$Cys-Gly-Arg-Asp-Ser-Pro-Cys)-Lys-OH | 1 |
| LS862 | DTPA-LS838 | DTPA-Cypate-Cyclo($_D$Cys-Gly-Arg-Asp-Ser-Pro-Cys)-Tyr-OH | 9 |

Example 2. Design and Identification of LS838 as a Pancreatic Ductal Adenocarcinoma (PDAC) Imaging Agent The current strategy to develop molecular probes with high binding affinity to a protein receptor overexpressed on tumor cells has allowed imaging of bulk tumor masses in vivo. Identifying gross tumors is straightforward in most cases. Unlike the bulk tumor, however, small tumors are surrounded by non-tumor tissue which also expresses the target receptor. Although the target protein is usually expressed at lower levels, the large surface area of the surrounding tissue increases the net background fluorescence, significantly decreasing the contrast between pathologic and uninvolved tissues. This concern was realized when previous attempts to use a dye-labeled RGD peptide or octreotate to target αvβ3 integrin or somatostatin receptors, respectively, reportedly overexpressed in PDAC, were not successful in identifying early stage PDAC. It was concluded that what is needed is a secondary trapping mechanism that can longitudinally retain a molecular probe in malignant cells while it clears from non-target tissue.

Figure 7A:
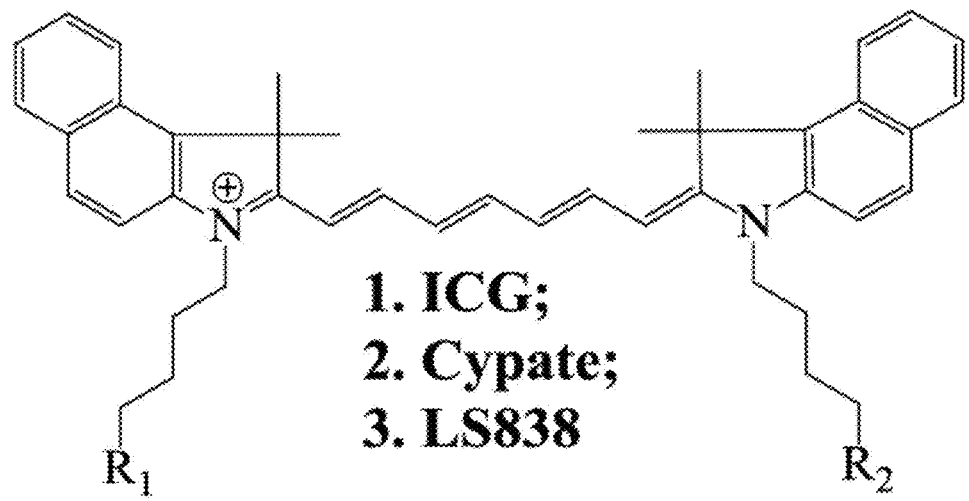
FIG. 7A, FIG. 7B and FIG. 7C depict structures of molecular imaging agents.

A new fluorescent molecular probe, LS838 (FIG. 7A) selectively targets early and late stages of PDAC. LS838 is a small molecule (<1.6 kDa) consisting of a NIR fluorescent dye (cypate) and an octapeptide that is cyclized through a disulfide bond. Cypate has a biological clearance profile and spectral properties (absorption, emission, quantum yield) similar to the FDA-approved indocyanine green (ICG; FIG. 7A), which is not tumor selective and does not react with biomolecules for targeted delivery to tumors. The spectral properties of LS838 are suitable for NIR fluorescence imaging studies (excitation/emission 785/810 nm in serum and 20% aq. DMSO solution; molar absorptivity, ε, 240,000 $M^{-1}$; $cm^{-1}$; and fluorescence quantum yield, iv, 10%). Cypate binds reversibly to the hydrophobic pocket of albumin, a source of nitrogen and energy for tumors. Unlike covalently dye-labeled albumin, cypate is released in tumors under mild acidic conditions as it traffics through the endosomal pathway. The released cypate is only transiently retained in tumors before efflux, limiting the tumor-to-background contrast.

To overcome this problem, the use of peptides as a tumor-trapping mechanism was explored. The highly reducing environment of tumor cells is known to reduce disulfide bonds to thiols, which can trans-thiolate with cysteine-containing intracellular proteins to trap the molecular probe. Therefore, a variety of disulfide-containing peptides were conjugated to cypate and the compounds were screened in mice with advanced stage PDAC. Results showed that LS838 was selectively retained in tumors for over 48 h, longer than the other peptide conjugates. Structure-tumor retention analysis revealed that the unnatural D-Cysteine linked to cypate confers high stability on the molecular probe because of its resistance to degradation by proteases. Replacement of the D-Cysteine with the natural L-Cysteine residue abrogates this retention.

Figure 8A:
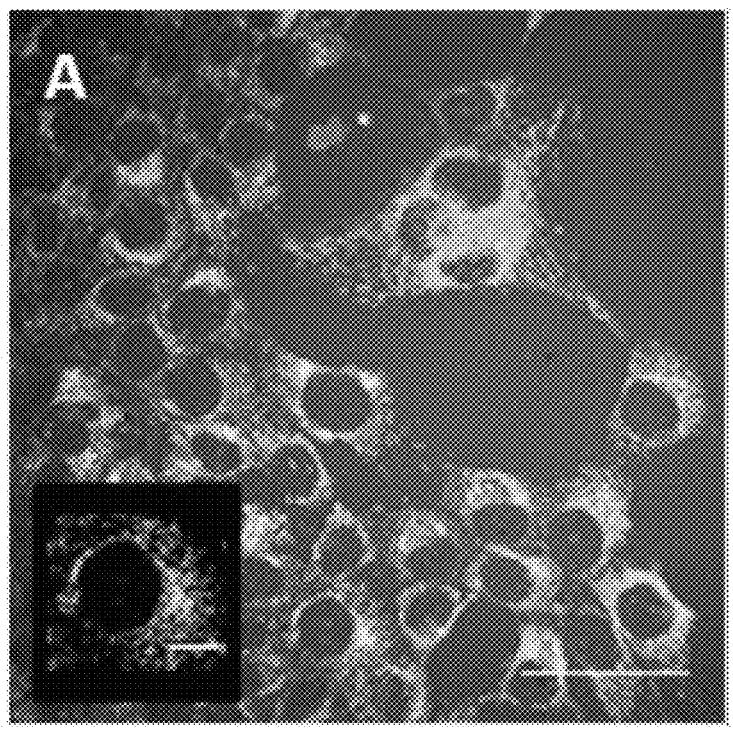
FIG. 8A and FIG. 8B depict uptake of LS838 in 4T1 luc cells showing internalization of the probe in the cells at 1 h (FIG. 8A) and 4 h (FIG. 8B) post incubation. Most cells show localization in the lysosomes at early time points, but the punctate fluorescence became more diffuse at 24 h, indicating translocation to the cytosol. Uptake in the mitochondria was negligible. Color scheme: cyan, Mitotracker; green, lysotracker; and red, LS838.
Figure 8B:
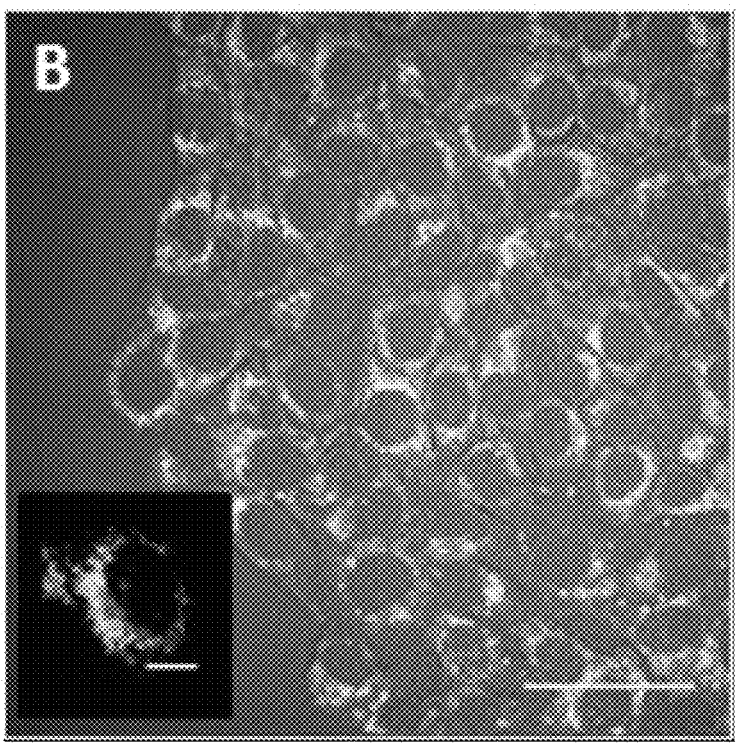
Figure 8C:
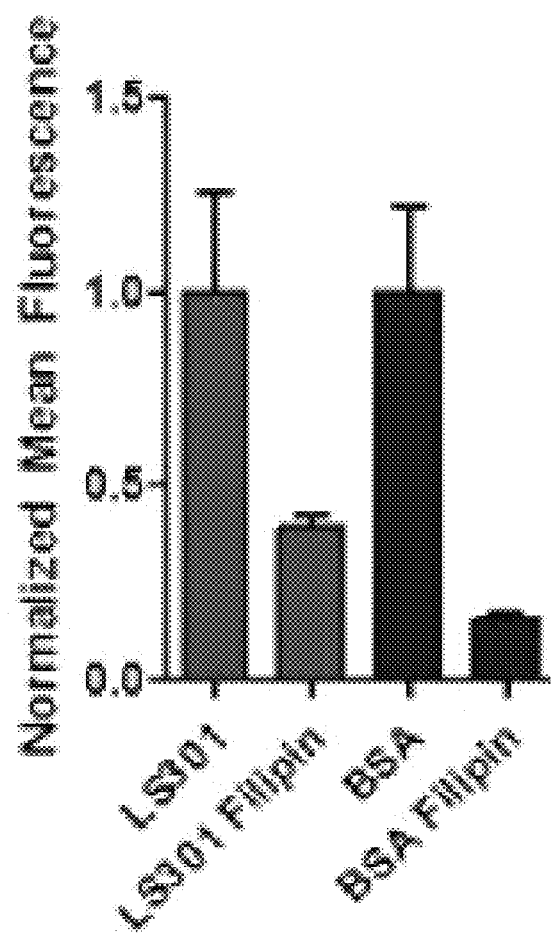
(FIG. 8C) Internalization of LS838 in cells was inhibited by Filipinin, an inhibitor of albumin endocytosis via the gp60 pathway. A similar inhibition was observed when Alexa-680 dye labeled albumin (BSA; blue) was mixed with LS838.

NIR fluorescence microscopy of LS838 in diverse tumor cells showed punctate intracellular fluorescence typical of receptor-mediated endocytosis (FIG. 8) and that the fluorescence uptake was barely visible in non-tumor cells (not shown). At early time points, LS838 is largely in the lysosomes, but it translocates to the cytosol in a time-dependent manner. Western blot, proteomic analysis, and blocking studies in cells with diverse inhibitors of albumin endocytosis point to albumin-mediated endocytosis (data not shown). This mechanism of uptake was further supported in vitro and in vivo by co-incubation of Alexa 680 labeled bovine serum albumin (BSA) with LS838, which showed colocalization of the two fluorophores in cancer cells at early time points, followed by divergence of the signals, indicating retention of LS838 and efflux of the Alexa 680.

Figures 9A, 9B, 9C:
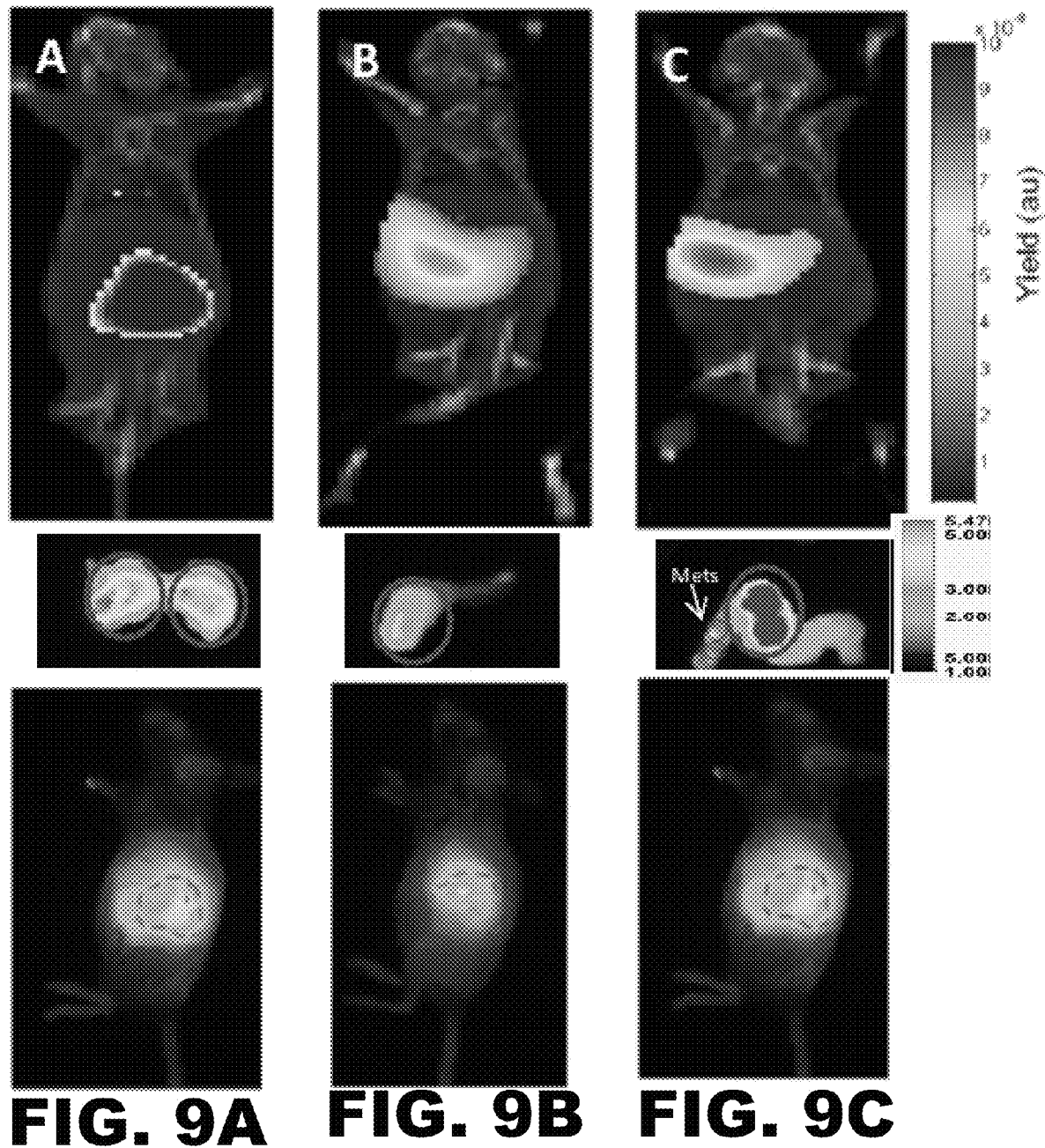
Figure 10A:
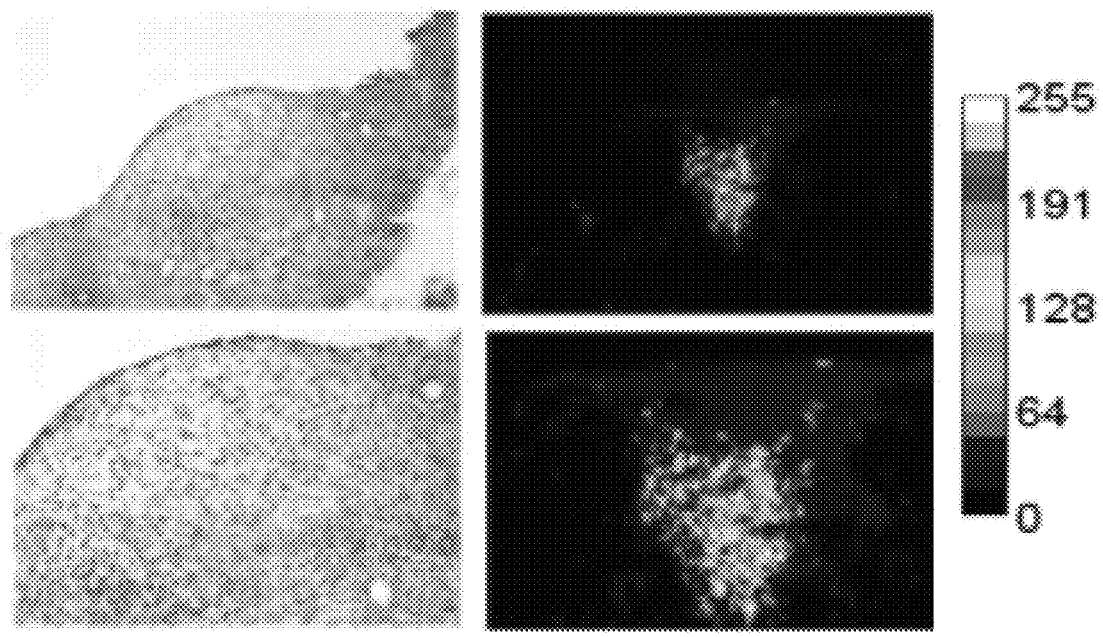
FIG. 10A, FIG. 10B, FIG. 10C, FIG. 10D and FIG. 10E depict H&E staining (left) and corresponding immunefluorescence (right) of pancreatic tissues from FIG. 9 after noninvasive in vivo imaging studies.
Figure 10B:
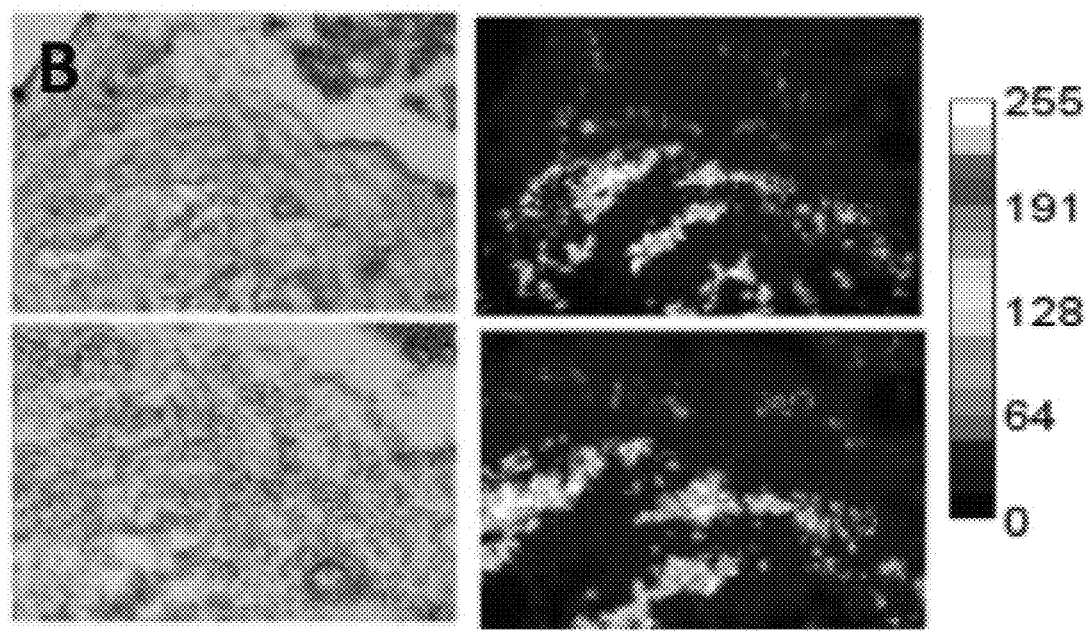
Figure 10C:
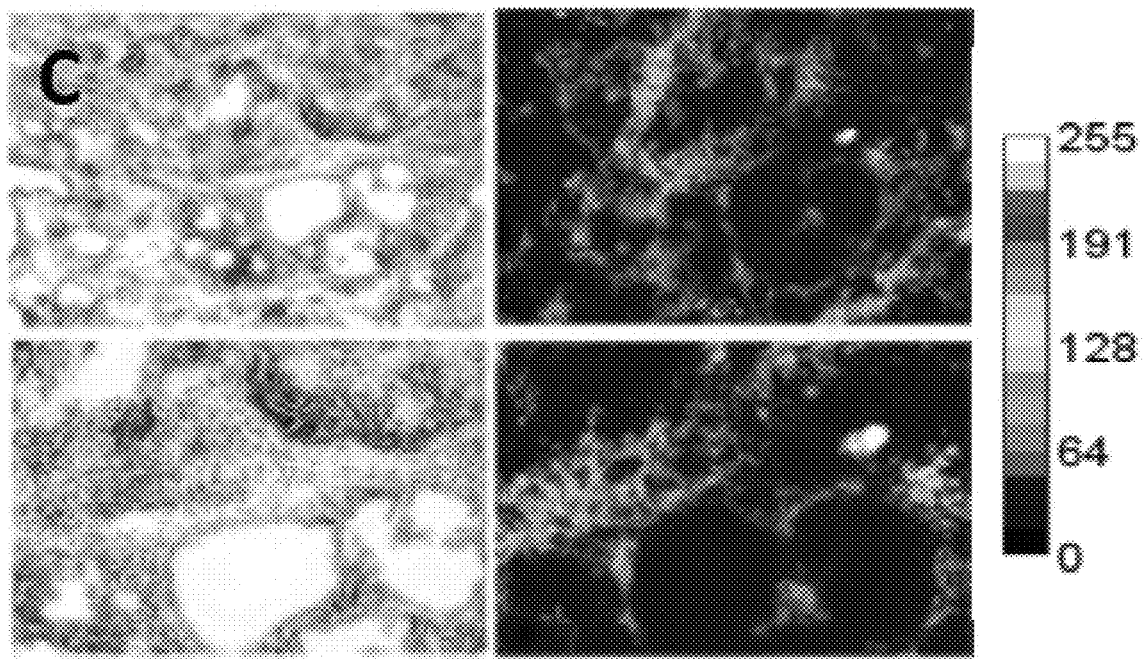
Figure 10D:
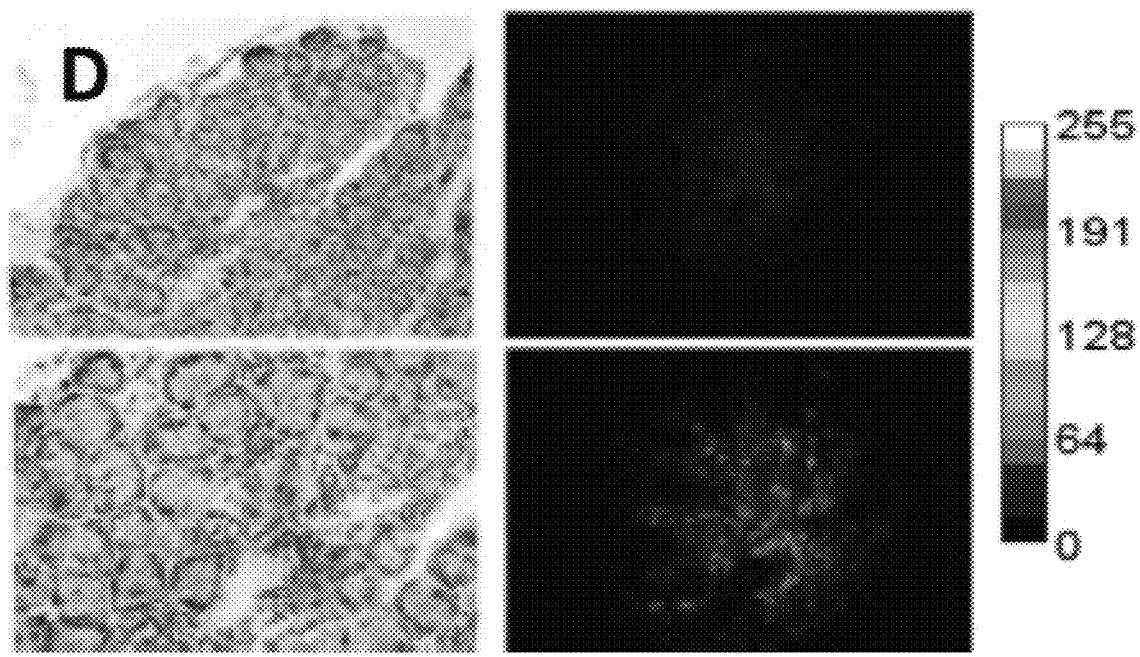
Figure 10E:
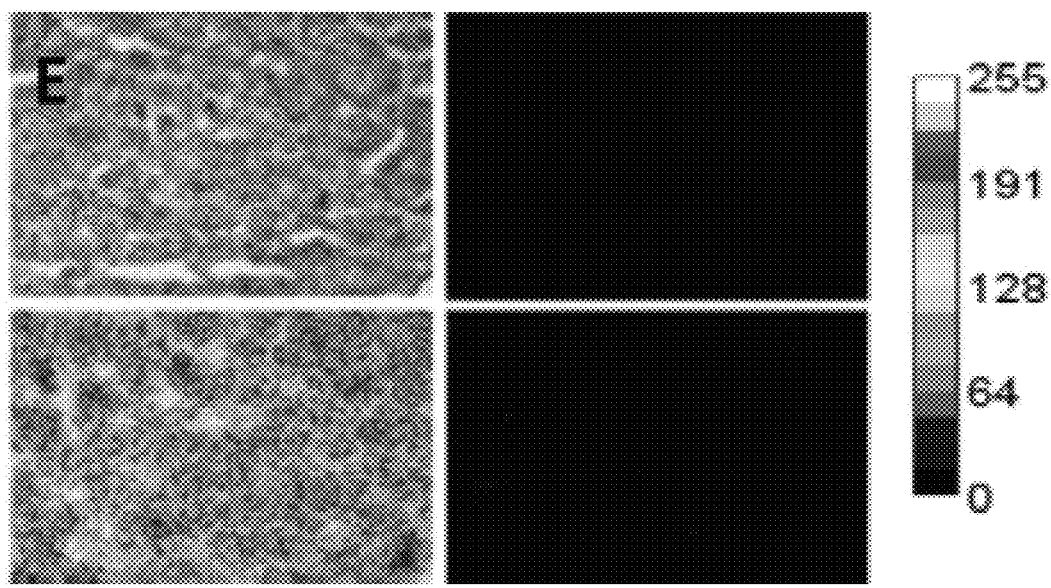

Example 3. LS838 Selectively Detects PDAC and Precursor Pancreatic Intraepithelial Neoplasia (PanIN) Cells with High Accuracy, and Distinguishes these Lesions from Acute and Chronic Pancreatitis LS838, genetically engineered KPC mice (p48-CRE/LSL-Kras$^{G12D}$/p53$^{Flox/+}$; activate KRAS and inactivate p53), and noninvasive fluorescence molecular tomography (FMT) were used to delineate pancreatic lesions. A high-speed FMT system was developed for quantitative imaging of molecular processes in vivo. Using quantitative FMT, results show that intravenous (i.v.) administration of LS838 allowed the detection of PDAC/PanIN lesions, which can be differentiated from acute and chronic pancreatitis (FIG. 9A-E). Reconstructed images 10 mm from the dorsal sides are shown for the different mice models. NIR fluorescence in the pancreatic region was drastically lower in both pancreatitis and Matrigel control models compared to that in PDAC and early neoplasia. The pancreas from different animal models was excised and imaged ex vivo. For the orthotopically implanted PDAC, fluorescence in the pancreas head was seen within a week of implantation, and the intensity increased by a factor of two within 2 weeks post-implant (FIG. 9A-B). Unlike the focal orthotopic tumor in the pancreas, the spontaneous model (PanIN/KPC) showed diffuse fluorescence in the pancreas (FIG. 9C). This is not surprising because this model readily transforms the majority of the pancreas into fully malignant tissue by the time the animals are 3-4 months of age. In contrast, LS838 fluorescence was barely detectable in the chronic and acute pancreatitis models, as well as in the control orthotopic Matrigel implant (FIG. 9D-E).

Histologic validation of the presence of pancreatic tumor cells in the LS838 fluorescent regions was performed by comparing the NIR fluorescence in tissue sections with hematoxylin and eosin (H&E) stained tissues (FIG. 10). The results confirmed the accurate detection of PDAC and precursor PDAC cells by LS838. Importantly, ex vivo tissue analysis of the chronic pancreatitis model showed significant fluorescence in a few areas of the pancreas which appears to correlate with PanIN-3 lesions that are known to progress to PDAC (FIG. 10D).

Figure 11A:
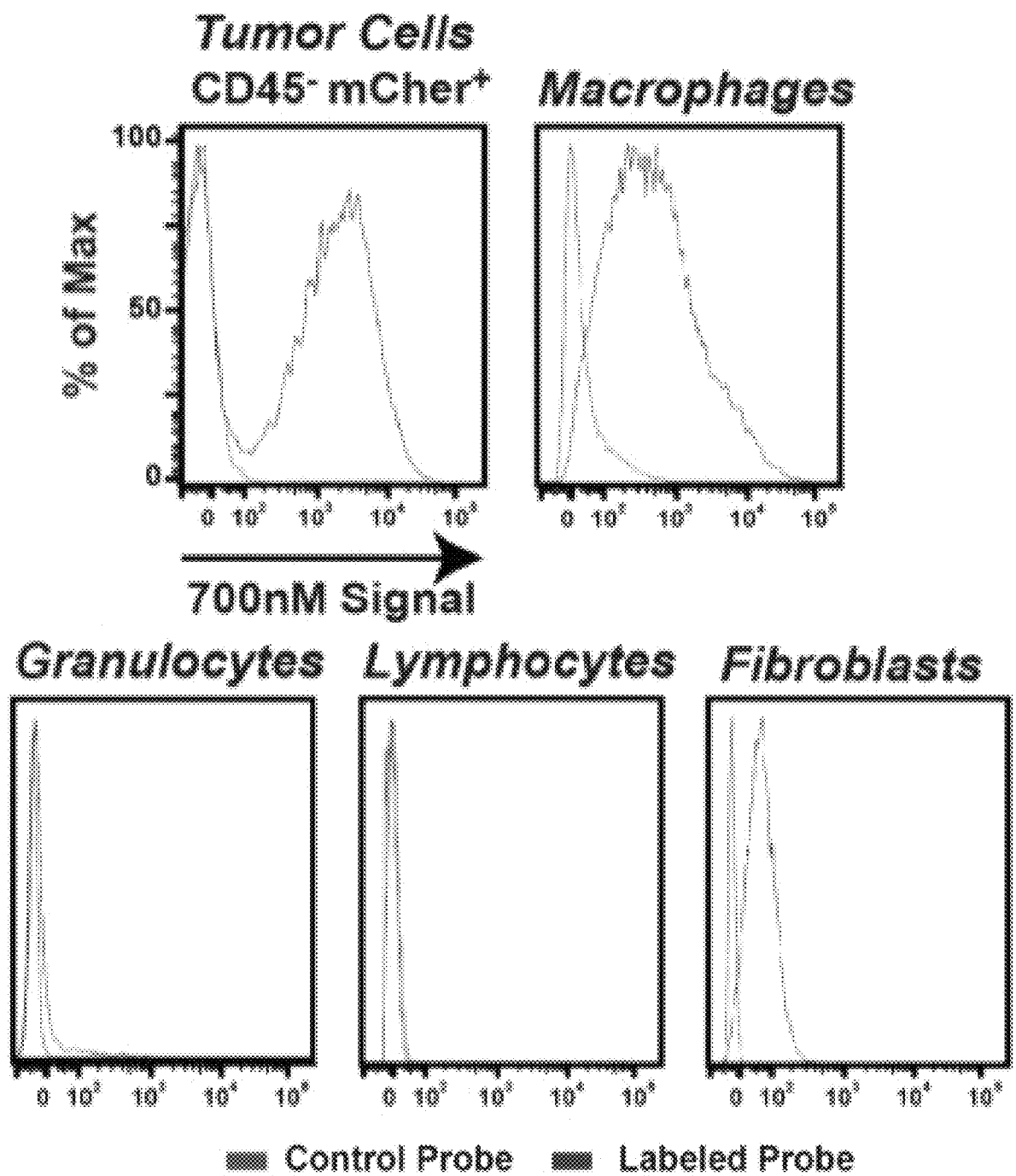
FIG. 11A depicts representative flow cytometry plots pre-gated for each cell type depicted. Cells are derived from established PDAC tumors treated with LS838.
Figure 11B:
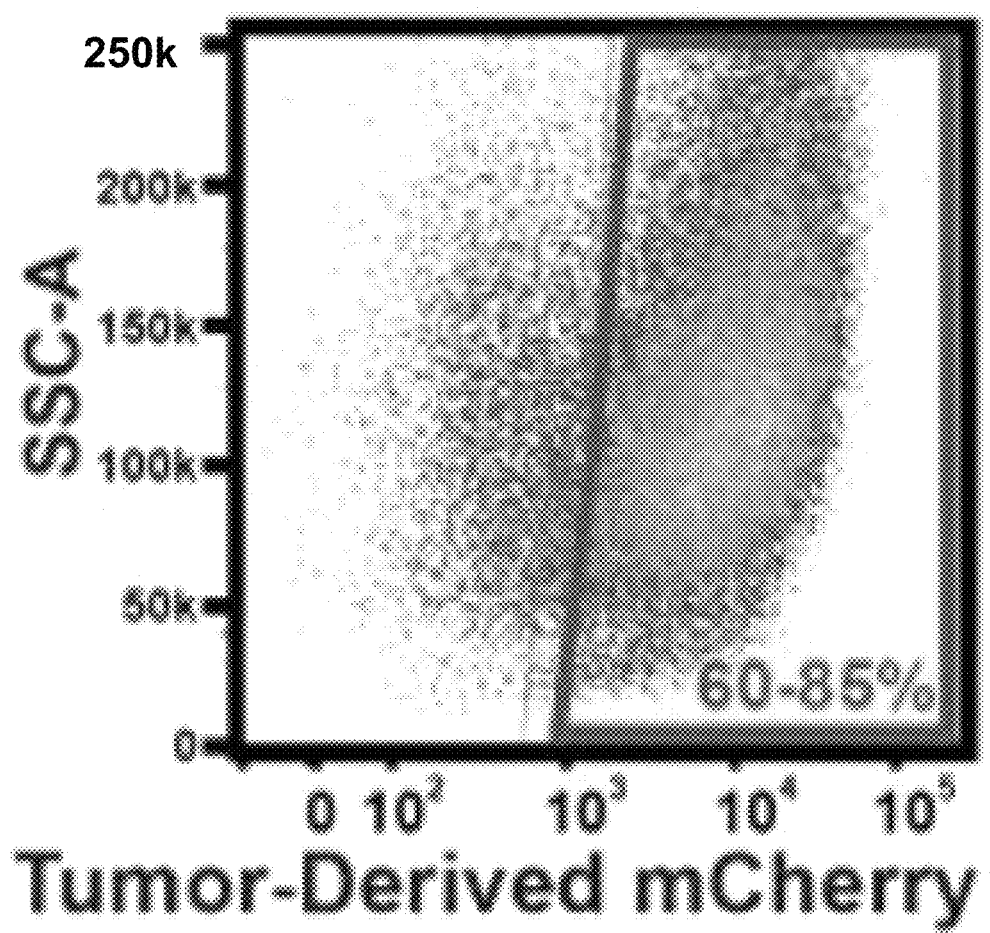
FIG. 11B, Tumor-derived mCherry signal is shown in tumor-infiltrating macrophages.

To determine the cell type(s) that take up LS838 in vivo, mice bearing established PDAC tumors stably transfected with a KP mCher$^+$ fluorescence reporter were treated with LS838. Tumor tissue was harvested and dissociated by collagenase digestion to obtain single-cell suspensions for analysis by flow cytometry. Using mCherry to identify PDAC tumor cells, it was found that uptake by these malignant cells was 100 to 1,000 times higher than in other cell types (FIG. 11A). Modest uptake was also seen in tumor infiltrating macrophages, but these macrophages were also labeled with mCherry derived from the tumor cells themselves, suggesting this fluorescence was a product of phagocytosis of PDAC cells (FIG. 11B).

Figure 12A:
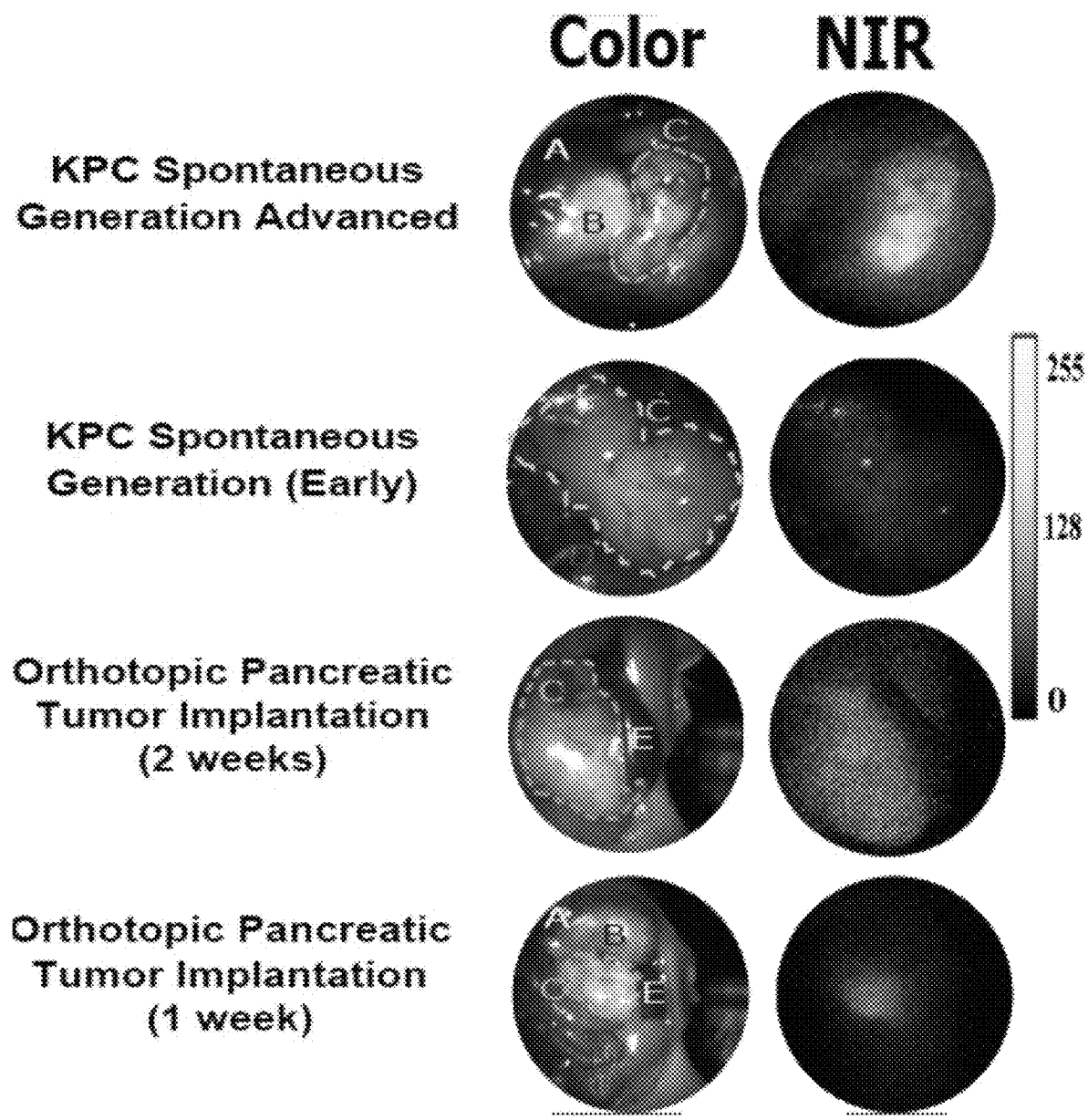
FIG. 12A and FIG. 12B depict laparoscopy of the pancreas and pancreatic lesions using different animal models and controls.
Figure 12B:
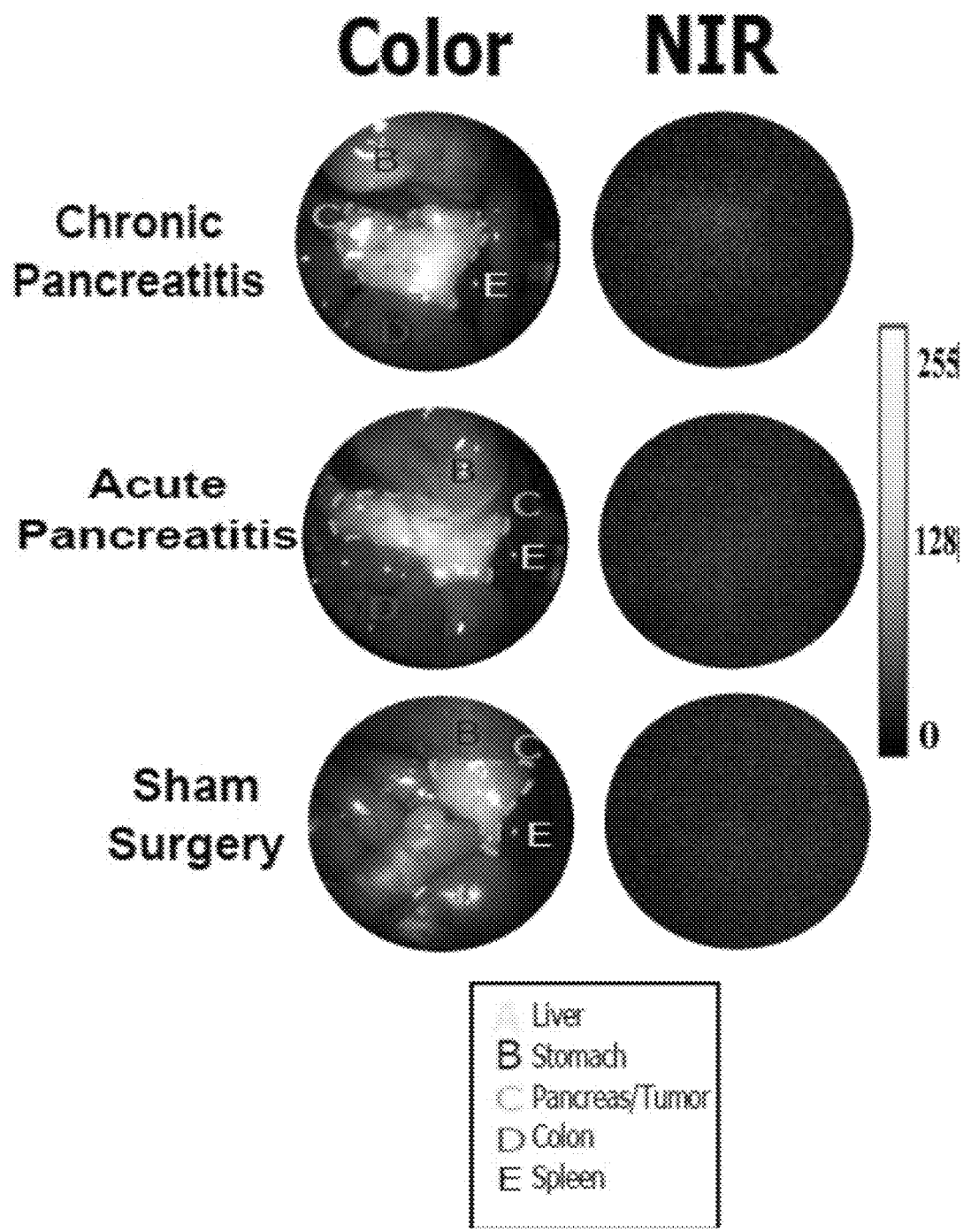

Example 4. NIR Fluorescence Laparoscopy Using LS838 Accurately Detects PDAC and Premalignant Neoplasia and Delineates these Lesions from Pancreatitis For laparoscopy, the Karl Storz rigid, straightforward telescope was modified so that it was capable of imaging in both visible (color; RGB) and NIR fluorescence modes. In the RGB mode, an endoscopic cold light fountain (Xenon Nova 175) with adjustable light intensity was used as the light source. The light cable was coupled to the illumination channel on a 0-degree Hopkins straightforward telescope. Images were captured by an NIR-sensitive CCD camera (Fluorvivo) with an RGB Bayer filter. A telescope coupler with a focus ring focused the CCD camera on the image formation plane at the back of the telescope. In the fluorescence mode, the cold light fountain source was replaced by a 780-nm excitation laser source with an incident light of 5 mW reaching the tissue. An 800-nm long-pass emission filter was placed behind the telescope in a slit of a custom-made adapter designed to couple the macro lens to the telescope. Images were captured using the Fluorvivo CCD camera with a quantum efficiency of 30% at 800 nm. Using this setup, the four murine models were investigated to provide validity to this approach. A midline incision was made to expose the peritoneal cavity of the mouse and the cavity was imaged at 90 degrees with a fixed distance of 4 cm. As shown in FIG. 12, the pancreas can be readily visualized by the conventional color image, but the LS838 NIR fluorescence selectively highlighted tumor tissues. Fluorescence in uninvolved pancreas and acute pancreatitis was below the detection limit of our device. Particularly exciting is the differential fluorescence in the involved and uninvolved pancreas, suggesting the ability to use this method to guide needle biopsy, assess surgical margins, and detect occult metastatic disease in real time. The detection sensitivity of the endoscope is low relative to a commercial system recently developed by Karl Storz, the Image 1H3-Z NIR fluorescence endoscope.

The encouraging results support the development of LS838 for detection of pancreatic lesions. In addition to delivering optical imaging agents and potentially drugs to PDAC lesions, the presence of tyrosine in LS838 structure allows for future radiolabeling of the molecule for noninvasive nuclear imaging applications.

Example 5. Synthesize and Characterize LS838 Analogues to Understand the Mechanism of LS838 Uptake and Retention in PDAC Relative to Uninvolved Pancreatic Cells The unprecedented retention of LS838 in pancreatic cells undergoing oncogenic transformation and PDAC cells requires further understanding of the retention mechanism. This is more so because the compound is not trapped in cells undergoing inflammation—as in acute or wound healing models. When some cells lit up in the chronic pancreatitis model, these cells were in the late stage of PanIN, thereby identifying the onset of PDAC. These studies were carried out in different animal models of pancreatic cancer with similar outcomes. The objectives of this study are to determine the trapping mechanism of LS838 in PDAC/PanIN tissues, improve the biodistribution profile of the compound so that fluorescence in adjacent organs and uninvolved pancreas will be minimal within an hour post injection of the agent, and formulate the compound for ease of administration and reduced uptake in non-target tissues.

Determine the Effects of Dyes and Peptides on the Uptake and Retention of LS838 in PDAC/PanIN.

Data strongly suggests albumin-mediated facilitated transport of LS838 into PDAC/PanIN-2/3 cells.

Figure 7B:
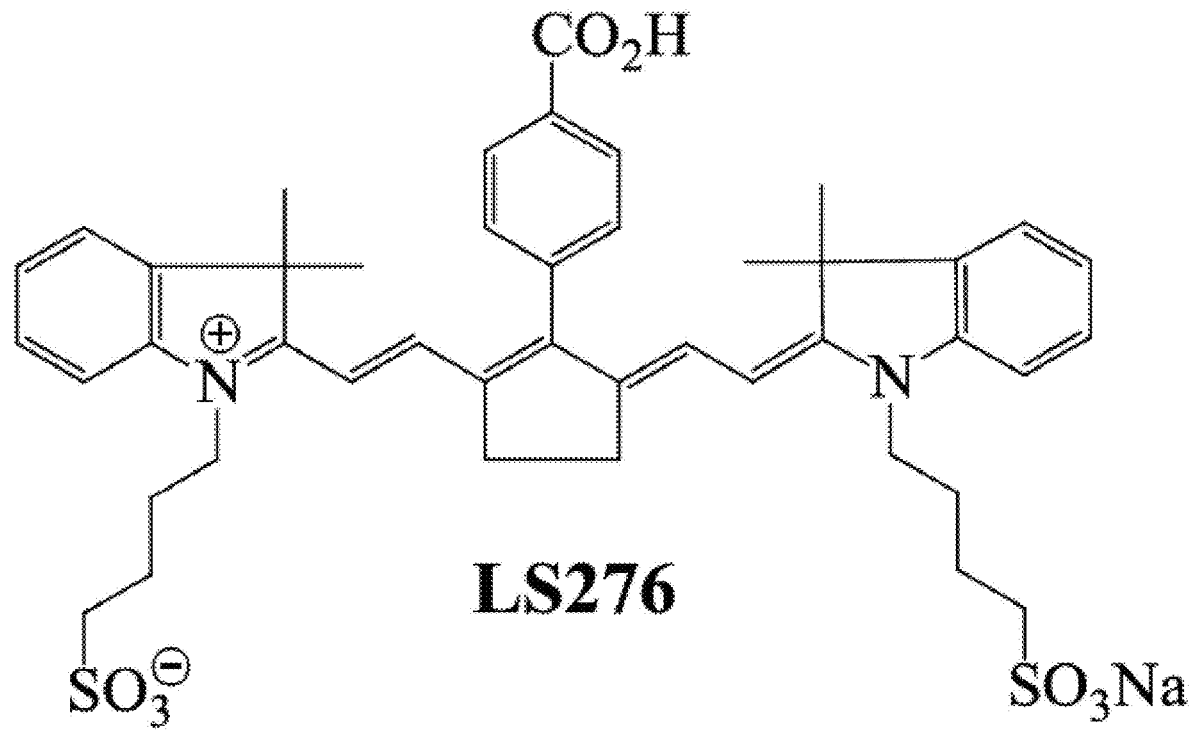
Figure 7C:
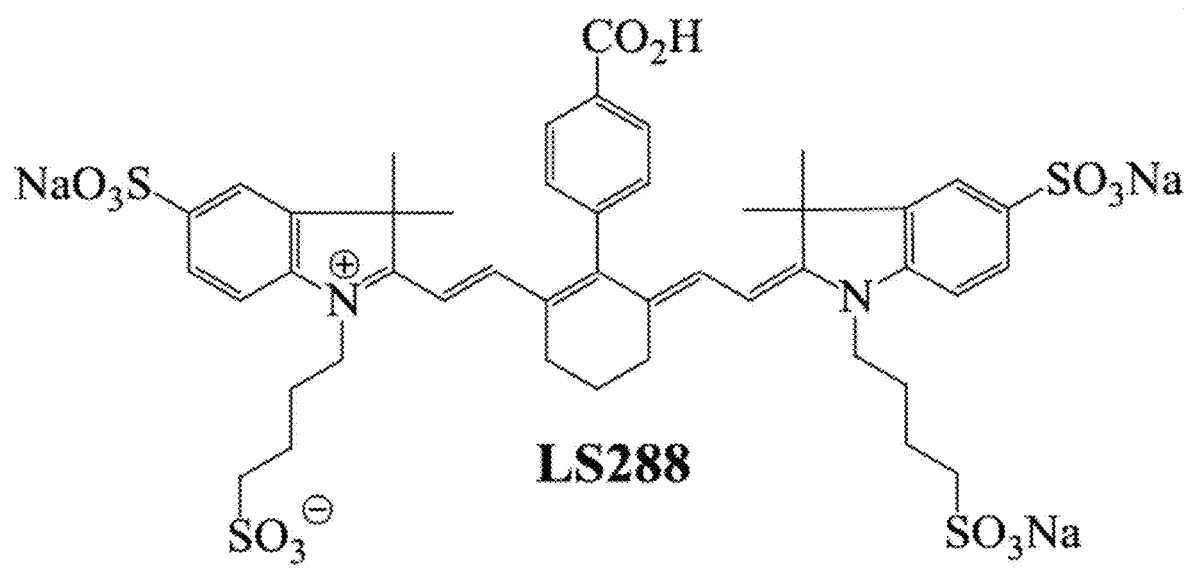

Dye Effect:

The hypothesis is that the binding of cypate to albumin facilitates the internalization of LS838 in PDAC/PanIN lesions. In a previous study, the binding of some carbocyanine dyes to albumin was compared. It was found that ICG and cypate possessed the strongest binding constant (K) to albumin, with values of 554,000 $M^{-1}$ and 556,000 $M^{-1}$ respectively, followed by LS276 (135,000 $M^{-1}$); LS288 bound the weakest (12,100 $M^{-1}$). The structures of LS288 and LS276 are shown in FIG. 7B-C. It was also shown that conjugation of peptides to the dyes decreases the K by a factor of ~10. Using the same method, we determined the K value of LS838 to be 86,000 $M^{-1}$.

By conjugating dyes with disparate albumin-binding constants to the same peptide sequence, this will validate the role of the dyes in the uptake, and possible retention, of the molecular probes. This will allow for the design of alternative compounds to LS838, if needed. The functionalizable dyes (Cypate, LS288, and LS276) will be conjugated to the LS838 peptide (denoted as GRD peptide; note that this is not the conventional RGD peptide).

For cell studies, each of the LS288 and LS276 conjugates of the RGD peptides (1 μM) will be incubated with the established PDAC cells. Flow cytometry will be used to quantitatively determine the rate of internalization by calculating the slope of a plot of fluorescence vs. time in 1000 cells (0.5, 1, 2, 4, and 8 h post incubation). Intracellular retention will be determined by washing the cells after 24 h incubation (when cytosolic fluorescence can be seen in cells treated with LS838). The cells will be incubated in fresh medium and the efflux rate (rate of fluorescence decrease with time at 0.5, 1, 2, 4, and 8 h post incubation after washing) will be determined by NIR flow cytometry using 1000 cells. The results will be compared with that of LS838 to establish the role of dyes in PDAC uptake and retention. By using a rate constant to report uptake and retention, bias in data analysis caused differences in the brightness (quantum yield×molar absorptivity) of each dye will be avoided. It is expected that the rate of internalization will correlate with the dye-albumin binding affinity, but that the retention rate will be similar if this parameter is mediated by the peptide (the same peptide is used) or aggresome (cell type effect; see below). Statistically significant differences in retention rates will indicate that the dyes also play a role in this parameter. This information will be used to optimize the molecular probe by combining features that favor fast internalization with those that promote high intracellular retention. If these parameters conflict, high retention rate over internalization rate will be chosen to achieve high fluorescence in tumor cells compared to non-tumor cells.

Peptide Effect:

Data shows that cypate dye alone internalizes in tumor cells, but then rapidly effluxes when the cells are transferred to a new culture medium. A similar trend is observed in vivo, where preferential uptake in PDAC relative to uninvolved pancreas is not observed. It was also found that replacement of D-cysteine with L-cysteine abrogated retention of LS838 in PDAC. Similarly, use of other cypate-labeled disulfide cyclic octapeptides, such as octreotate, did not achieve statistically significant contrast between PDAC and the surrounding pancreas. These results suggest that the peptide plays an important role in the selective retention of LS838 in PDAC tissue. Permutation of the arginine-aspartic acid sequence results in a loss of PDAC-selective uptake. It has been shown that cypate binds to the hydrophobic pockets of albumin, irrespective of the source (human, murine, or bovine). The reduction in binding constant upon conjugation with peptides suggests that the peptides perturb the albumin-dye interaction. Thus, the primary goal of this study is to determine the role of the peptide in tumor cell internalization or retention. Based on preliminary data, this question can be addressed by preparing the following cypate-labeled peptides (underlined amino acids are changes made to LS838):

```
                                        (SEQ ID NO: 11)
cyclo(DCys-Gly-Arg-Asp-Ser-Pro-DCys)-Tyr-OH;

(SEQ ID NO: 12)
cyclo(Cys-Gly-Arg-Asp-Ser-Pro-Cys)-Tyr-OH;

(SEQ ID NO: 13)
cyclo(Cys-Aro-Gly-Asp-Ser-Pro-Cys)-Tyr-OH;

(SEQ ID NO: 14)
cyclo(DCys-Arg-Gly-Asp-Ser-Pro-Cys)-Tyr-OH;
and
                                        (SEQ ID NO: 15)
cyclo(DCys-Arg-Gly-Asp-Ser-Pro-DCys)-Tyr-OH.
```

The peptides will be prepared and labeled with cypate at the N-terminus. The albumin binding constants will be determined as described above to assess the perturbation of the dye-albumin interaction, which could affect cell uptake. Using the internalization and retention rates described above, whether loss of contrast is due to poor uptake or poor retention in tumors will be determined. The data will allow the determination if loss of PDAC selectivity is caused by a poor internalization rate due to perturbation of the dye-albumin binding. In that case, spacers will be incorporated, such as various lengths of polyethyleneglycols, between the dye and the peptide to minimize this perturbation. If the loss of uptake is caused by a high efflux rate, the intracellular target of LS838 will be determined, as described below.

Determine the Mechanism of Selective Trapping of LS838 in Pancreatic Lesions.

Data indicate that LS838 rapidly internalizes in the pancreas within 1 h post injection, but then remains primarily in the tumor cells (up to 100 h) relative to non-tumor cells. Cellular studies suggest that LS838 undergoes time-dependent translocation from the lysosome to the cytosol in cancer cells, but remains in the lysosomes in non-tumor cells before efflux from the cells. This trafficking profile was not observed with the control probes nor with the cypate dye alone, which showed transient retention in tumor cells before efflux in a similar manner as non-tumor cells. Proteomics studies show the association of LS838 with a protein determined to possess a significant albumin peptide sequence. Western blot analysis indicated the association of LS838 fluorescence with α-actinin-4 protein and a fatty acid receptor protein. Therefore, to understand why LS838 is able to be selectively retained by pancreatic tumors, two hypotheses will be tested.

Hypothesis 1: A Dysfunction in the Clearance of LS838 from Cancer Cells Will Decrease the Efflux Rate, Thereby Increasing the Selective and Longitudinal Retention of the Imaging Agent in Cancer Cells.

Data show that a significant amount of LS838 is retained in the lysosomes for over 24 h in tumor cells, but lies in a perinuclear inclusion in normal cells. Aggresomes are microtubule-catalyzed aggregates of lysosomes that are used to degrade particularly stable and aggregated proteins. It is postulated that LS838 forms stable aggregates with albumin which may require the formation of aggresomes for their removal. It will be evaluated if tumors have a lower ability to form aggresomes because of microtubule dysfunction, leading to prolonged retention in tumor cells compared to normal cells. If LS838 induces aggresome formation in tumor cells, but not fibroblasts will first be determined. Using the ProteoStat Aggresome detection kit, an assay for aggresome formation will be performed using literature methods. It will also be determined if aggresomes form in vivo using a literature method. LS838 will be injected into mice and they will be euthanized 24 h post injection. Aggresome formation will be determined by staining muscle, skin, and tumors for anti-ubiquitin protein. Aggresome formation will be confirmed by TEM visualization of perinuclear inclusions. Control studies with LS838N and cypate will be conducted. The hypothesis will be positively tested by demonstrating that the rate of aggresome formation in PDAC cells is slower than in non-tumor pancreatic cells, with a p≤0.05.

Hypothesis 2: Longitudinal Retention of LS838 in Cancer Cells is Mediated by Trans-Thiolation with Intracellular Biomolecules Via the Stable (Unnatural) D-Cysteine Amino Acid Linked to Cypate.

Data show that LS838 can be internalized in tumors, but rapidly clears before attaining significant tumor-to-background contrast if any one of the D-cysteine, lysine, or aspartic acid residues is replaced with different amino acids. In one set of proteomic data, which was confirmed by Western blot, α-actinin-4 protein (~104 kDa) and fatty acid receptor proteins (~37 kDa; 15 kDa) were identified as potential intracellular targets for LS838. It is expected that under the high reducing intracellular environment of cancer cells, the reduced thiol groups of α-actinin-4 can cross-link with the thiol from the D-cysteine of LS838 peptide. It is likely that the hydrophobic cypate dye interacts with the fatty acid receptor, providing sufficient resident time in cells for trans-thiolation to occur.

A proteomic approach will be utilized to identify the intracellular biomolecules that bind strongly with LS838 in cancer cells. The cells will be trypsinized and lysed, and then the lysed protein will be fractionated and analyzed for NIR fluorescence. Compared to non-treated cell protein distributions along the anionic exchange column, bound proteins will be slightly shifted in their anionic charge in the treated cells. The combination of anionic shift and overlap in NIR fluorescence will help identify candidate proteins for binding affinity. Proteins shifted in anionic charge by LS838, but not shifted by cypate, will be used to identify candidates for proteins involved in retention. The identified proteins that match the above criteria will then be analyzed for binding affinity using a competitive binding assay. To normalize the data, the binding affinity will be expressed as apparent binding constants. Confirmation of a protein's retention effect will be determined by pre-incubating tumor cells with competitive inhibitors of the protein. It is expected that there will be a significant loss of LS838 retention in tumor cells, which will be expressed as percent inhibition. Additionally, siRNA may be used to knockout/down the target protein to establish functional validation of the retention mechanism. All experiments will be conducted with cypate and dye-labeled peptide derivatives.

Determination of the Cytotoxicity of LS838:

To assess the cytotoxicity of LS838, commercially available normal (non-tumor) human primary pancreatic cells (T0199 from ABM), and non-tumor cell lines from the two major excretion organs, the kidneys (HK-2) and liver (Fa2N-4) will be used. Primary pancreatic adenocarcinoma (BXPC3) or other cancer cell lines will also be used to assess potential toxicity in tumors. The cytotoxicity tests will be performed by the 3-(4,5-dimethylthiazol-2-yl)-2,5-diphenyltetrazolium bromide (MTT) assay. Based on a previous study, it is expected that the molecular probes will have a lethal dose (LD50)>100 μM in cells, which is orders of magnitude above what is expected to be used for in vivo imaging. The NIR confocal microscope (FV1000, Olympus) will be used to assess the intracellular distribution of the probes. All the methods for these assays are standard.

LS838 currently clears through the liver. While this is not a problem in the proposed laparoscopy, the excretion route to the kidneys can be altered by conjugating positively charged moieties (—$^+$NMe$_3$) or nonionic groups (e.g. PEG) to the free carboxylic acid group of cypate. It was found that conjugation of small molecules (<500 Da) does not affect LS838 binding to tumors. In the unlikely event that the cyanine dyes are photo-unstable, they will be replaced with NIR pyrrolopyrrole cyanine dyes (PPCy), which are highly photostable and have exceptionally high fluorescence quantum yields (up to 80%).

Example 6. Determine the Role of Kras-Induced Oncogenic Transformation on the Selective Uptake and Retention of LS838 by PDAC/PanIN-2/3

The detection and differentiation of advanced lesions (PanIN-3 and PDAC) from more indolent disease (PanIN-1/2) and ductal hyperplasia/metaplasia would inform more aggressive treatment decisions. It will also be determined if activated Kras-mediated oncogenic transformation of non-malignant pancreatic cells to PDAC drives specific uptake and retention of LS838 in malignant cells. Information on in vivo imaging methods is summarized in Example 7.

Determine the Specificity and Sensitivity of LS838 in Detecting Early PanIN and PDAC Lesions:

Data show that LS838 identifies advanced PDAC tumors and microscopic PanIN3$^+$ lesions. However, it is not yet known the earliest stage of disease that LS838 can differentiate from non-tumor tissue. This is an important clinical question, as the ability to non-invasively detect early PanIN lesions would allow for increased surveillance in these individuals without further major surgical procedures. In particular, the detection and differentiation of advanced lesions such as PanIN3 and PDAC from more indolent disease, i.e. PanIN1-2 and ductal hyperplasia/metaplasia, would inform more aggressive treatment decisions. Thus, the disease stages detected by LS838 will be defined.

Mouse models for PDAC, indolent and aggressive PanIN, and chronic pancreatitis will be used in these studies. While LS838 is visible in histologic sections, this signal is significantly reduced during tissue processing for standard immunohistochemistry, making co-localization with cell type specific markers in tissue sections difficult. To overcome this barrier, KPC-Y mice (p48-CRE/LSL-Kras$^{G12D}$/p53$^{Flox/+}$; YFP+) will be employed. This model will allow the specific detection of LS838$^+$/YFP$^+$ transformed cells even in very early PanIN lesions. Using KPC-Y mice aged to 2, 3 or 4 months of age, LS838 signal intensity will be assessed using a combination of non-invasive quantitative FMT (FIG. 9) in vivo and high resolution ex vivo imaging of the pancreas to assess the distribution of LS838 in these early stage tissues. Using YFP-positivity to identify transformed cells (Kras$^{G12D}$+ cells), the spectrum of LS838 retention in pre-malignant and malignant cells will be assessed by flow cytometry. Additionally, co-localization of LS838 and YFP+ will be analyzed in frozen tissue sections, and fluorescence intensity in individual PanIN-1, -2, -3 and PDAC lesions (using MetaMorf) will be determined and compared to histology as the Gold Standard. Together, these data will determine at what stage of PDAC progression LS838 is selectively retained in pre-malignant cells and when disease is discernable by non-invasive imaging.

To determine if LS838 selective uptake and retention is increased as Kras-transformed pancreas cells move from indolent to progressive disease, pancreatitis-induced disease progression in p48-CRE/LSL-Kras$^{G12D}$/LSL-YFP mice will be analyzed. Without the loss of p53, the majority of these mice will have stable early stage PanIN disease that will not progress to PDAC. However in the context of Caerulein induced pancreatitis, disease will progress stochastically. LS838 signal intensity will be assessed using a combination of non-invasive quantitative FMT and ex vivo imaging of the pancreas in 2-month-old p48-CRE/LSL-Kras$^{G12D}$/LSL-YFP and control (p48-negative) mice treated with Caerulein (50 mg/kg×3/week) or vehicle for 1 and 3 months. Pancreatic tissues from these mice will be analyzed by flow cytometry and immunofluorescence microscopy for LS838 in YFP+ cells, as described above. Nine mice will be analyzed for each group at each stage. These experiments will determine if LS838 selective uptake and retention is increased as transformed cells move from indolent to progressive disease during pancreatitis.

Determine if Kras-Induced Oncogenic Transformation Leads to LS838 Selective Uptake and Retention:

Activating mutations in Kras are present in >90% of pancreatic adenocarcinomas, but are often also found in indolent hyperplastic or dysplastic pancreas tissue. To determine if oncogenic transformation by activated Kras drives malignant cell specific uptake and retention of LS838, the effects of Kras mutation on LS838 retention in vitro will be assessed. To accomplish this goal, normal pancreatic ductal epithelial cells from LSL-KrasG12D mice will be isolated using standard protocols. To rearrange wild-type Kras into oncogenic Kras$^{G12D}$, isolated pancreatic epithelial cells will be infected with Adenovirus encoding CRE and GFP or GFP only (as control). About 48 h after infection, GFP+ cells will be FACS sorted for use. The uptake and retention of LS838 will be assessed in Kras$^{G12D+}$ and negative pancreatic epithelial cells. The data will be compared to cell lines isolated from late stage KPC mice. Both imaging and flow cytometry will be used to determine uptake and retention every 3 h for 36 h. These data are important because they will determine if oncogenetic transformation alone is sufficient to induce specific LS838 uptake and retention. Direct correlation will provide an indirect method to report the expression level of Kras necessary to stimulate oncogenic processes in cells.

The sensitivity and specificity for detecting cancer and neoplasia will be analyzed. The relative contrast of tumor to surrounding healthy tissue will be measured for each tumor to determine specificity of the molecular probe and sensitivity of the endoscope. The relative contrast of tumor to surrounding healthy tissue will also be measured for each tumor to determine specificity and sensitivity of the molecular probe. The statistical significance of tumor-specific contrast will be analyzed using Student's t-test with alpha=0.05 and P<0.05 considered significant. It is expected that LS838 will produce high sensitivity (>90%) and specificity (>90%) for PDAC and will distinguish these lesions from pancreatitis.

Kras expression may not correlate with the uptake of LS838. In that case, the results will indicate the earliest PanIN cell phenotype detected by LS838. An alternative hypothesis is that the uptake of LS838 may correlate with an increase in the proliferation state of transforming pancreatic cells. In this case, the relationship between LS838 uptake and the metabolic status of tumors will be determined by correlating LS838 uptake with uptake of [$^{18}$F]-2-fluorodeoxyglucose, a reporter of glucose metabolism, using PET.

Example 7. Determine the Accuracy of Detecting PDAC/PanIN in Human Patient-Derived PDAC and Mouse Models that Recapitulate Different Stages of PDAC Genetic models of PDAC progression in mice as well as acute and chronic pancreatitis models will be used for this study. This model will be used to assess the translation of findings using LS838 in mouse to human models of PDAC. It is expected that LS838 will accurately characterize pancreatic lesions and potentially identify occult metastatic disease at the time of surgery.

Determination of the Accuracy of Imaging PDAC and Chronic Pancreatitis Mouse Models Using LS838:

PDAC, premalignant neoplasia, and chronic pancreatitis models will be employed in this study. The optimal injection dose to obtain the best tumor/normal tissue contrast will be determined. It is expected that tumors <0.5 mm diameter will be detected. LS838 and a nonspecific control [LS838N: Cypate-cyclo(Tyr-Gly-Arg-Asp-Ser-Pro-$_D$Cys)-Lys-NH$_2$] (SEQ ID NO:16), will be administered intravenously (i.v.) using 10 nmol of the molecular probe dissolved in PBS containing 2% mouse serum albumin per 25 g mouse (this concentration was used in preliminary studies, but will be varied to optimize dosage: 1, 5, 10, and 20 nmol/25 g mouse). We will use KPC mice at 3 different stages of PDAC development: (a) PanIN-1/2-1-2 months; PanIN-2/3-2-3 months; and advanced PDAC→4 months. The animals will first be imaged longitudinally and noninvasively with the fluorescence molecular tomography (FMT) system. A side view will be used to image the pancreas using the LICOR planar NIR imaging system. Non-invasive imaging will be performed at 0.5, 1, 4, 8, 18, 24, 48, 72, and 96 h after injection to determine the longitudinal retention of the agent in PDAC. Imaging will be stopped when fluorescence in the tumor and adjacent pancreas are similar or indistinguishable by the imaging systems. Noninvasive FMT will first be used to image the mice at 1, 4, 8, 24, and 48 h post injection before exposing the pancreas by skin incision and gentle retraction with blunt dissection. Using a Karl Storz Image 1H3-Z color-NIR fluorescence endoscope, endoscopy of the pancreas will be simulated to determine the detection and delineation of pancreatic lesions. A cholangiopancreatoscope will be used to identify areas of high fluorescence intensity (FIG. 12), a feature that is useful for image-guided surgery. Acquired images will be processed via the controlling software to measure the fluorescence intensity from areas identified as tumor or normal. These values will be used to establish thresholds for tumor detection. Receiver Operating Characteristic curve (ROC) analysis will be used to determine the threshold fluorescence contrast for detecting PDAC cells. Based on preliminary data, it is expected that >20% NIR fluorescence in PDAC cells relative to the intensity in uninvolved pancreas will serve as an internal control to delineate this lesion. Suspicious areas, including highly fluorescent and non-fluorescent pancreatic tissues with and without obvious tumors, will be excised and snap-frozen for cryosectioning. Frozen tissues will be examined by fluorescence microscopy and data will be referenced to histopathology as the gold standard.

Determination of Biodistribution of the Molecular Probes:

A simple method for fluorescence-based biodistribution studies will be used. Briefly, after completing endoscopy at the time points indicated above, mice will be euthanized by cervical dislocation. Aliquots of blood and all major organs (pancreas, heart, kidney, lung, spleen, stomach, intestine, muscle, kidney, adrenals, liver, skin, bone, and brain) will be harvested, washed with PBS, dried and weighed. The organs and a small glass vial containing a known volume of blood will be imaged with the LICOR NIR planar imaging system. Using a reference tissue model (a known concentration of the molecular probe is injected into similar tissues from untreated mice) as fiducial markers, the relative uptake of the probe in various tissues will be determined. This approach will allow normalization of differences in the optical properties of tissue. The imaging system has software that calculates the mean fluorescence count plus or minus standard error of mean within any chosen area on the fluorescence image. The relative uptake as percent fluorescence per gram tissue relative to the pancreas will be reported. Organs will be processed for histopathology. Tissue classification as PDAC/PanIN vs. pancreatitis by LS838 fluorescence will be compared with histopathology to determine the diagnostic accuracy of our approach.

Determination of the Detection of Microscopic PDAC Using LS838-Aided NIR Laparoscopy to Improve the Diagnostic Yield of Pancreatic Biopsies:

A potential advantage of using LS838 is the potential to detect microscopic PDAC cells when visual inspection or white light is not capable of identifying these lesions.

LS838-aided biopsy of the pancreas will be simulated by using early stage PDAC in the KPC mouse model, when a significant number of cells are in the PanIN-2/3 stage, as reported by the KPC-Y model. Based on the point of highest contrast between PDAC and uninvolved pancreas as determined above, the NIR laparoscope will be utilized to identify PDAC cells, (as described above) to simulate tissue biopsy (n=9). Resected tissue will be analyzed and scored by histopathology. It is expected that the NIR fluorescence-aided tissue sample collection will improve the yield of pancreatic biopsy with accuracy approaching 100% relative to conventional biopsy.

Determination of the Distribution and Uptake of New Molecular Probes Synthesized in Example 5 by PDAC:

New compounds will be prepared as described in Example 5. When they become available, the optimized imaging time point and injected dose of LS838 will be used to determine the in vivo biodistribution and retention of the new compounds. Specifically, these parameters will be determined for LS276 and LS288 dye-labeled analogues of LS838 (role of dye in retention), as well as for two molecular probes from the modified peptide analogues of LS838 based on the in vitro results (role of peptide in retention). Thus, in addition to LS838, four new molecular probes will be imaged and the data compared with those of LS838. The animals will be imaged at 1, 4, and 24 h post injection before excising their organs for biodistribution studies, as described above. It is expected that the in vivo results will confirm the findings of the cell studies. Together, the information can be used to optimize the structural features of LS838 for rapid uptake and retention in tumors, with the highest contrast between tumor and uninvolved pancreas within 4 h post injection.

Determination of the Potential Use of LS838 Fluorescence to Detect PDAC from Human Patients:

The PCBC SCC has established >30 PDAC lines from resected pancreatic cancer specimens and has developed heterotopic and orthotopic PDXs (Patient Derived Xenografts) in NOD-SCID mice. PDXs and their derivatives are attractive model systems. PDXs are typically generated by subcutaneous implantation of human tumors directly from patients (via biopsy or surgery) into immunodeficient mice (generally mice based on the non-obese diabetic—severe combined immunodeficient, or NOD-SCID, background). Tumors can then be passaged serially in NOD-SCID mice via heterotopic (subcutaneously) or orthotopic (into the originating organ) transplantation and used as a model system for various aspects of cancer research. Some advantages of PDXs and their derivatives include: (1) their human tumor origin, (2) the ability to correlate findings in PDX models with the clinical outcomes of the patients from which the PDXs and derivatives were established, and (3) the potential to use PDXs to develop translational oncology model systems to study, for example, metastatic biology and to evaluate novel therapeutics.

27 mice each of heterotopic and orthotopic PDX bearing NOD-SCID mice from the PCBC SCC will be obtained for this study. The accuracy of identifying PDX in both models (n=9 for each model) will be determined as described above using LS838 and the non-PDAX specific control compound, LS838N. Imaging will commence when tumor size reaches ≥5 mm (determined by caliper measurement for the heterotopic model and established growth rate for the orthotopic model). After administering the imaging agent (10 nmol/20 g mouse), longitudinal FMT imaging will be performed at 0.5, 1, 4, 8, 18, and 24 h. At 24 h, laparoscopy will be conducted as described above and the animal will be euthanized for biodistribution analysis and histopathology. Because LS838 is intended to be used in patients scheduled to undergo surgery or exploratory laparoscopy, another set of 9 mice will be used for laparoscopy and biodistribution/histology to simulate clinical settings. A similar study will be conducted with LS838N. Data will be processed and analyzed as descried above. It is expected that LS838 will have similar accuracy in detecting PDX as mouse PDAC. The results will provide preclinical data to determine potential translation of the compound in humans. The sensitivity and specificity (accuracy) will be calculated as well as positive and negative predictive values of PDAC/PanIN detection using LS838 based on the histology data.

Data strongly supports the feasibility of using LS838 to delineate PDAC and premalignant neoplasia from pancreatitis. LS838 fluorescence may not correlate with presence of disease determined by histology. In this case, YFP fluorescence from the KPC-YFP model will be used to determine early PDAC lesions. The quantitative accuracy of FMT system and NIR laparoscope may be affected by differences in tissue optical properties. Since LS838 has a tyrosine residue, the compound could be radiolabeled with $^{125}$I for SPECT imaging and biodistribution studies (note that thyroid uptake of iodine will be considered in data analysis).

The methodologies described herein result in the following, non-limiting innovations:

1: A novel imaging agent, LS838, has been developed which detects PDAC and PanIN 2/3 lesions with high accuracy. A new uptake mechanism involves facilitated uptake mediated by the energy needs of these metabolically active cells, followed by intracellular trapping under the highly reducing environment of these cells.

2: Application of LS838 to distinguish PDAC and transforming PanIN from chronic pancreatitis with high accuracy represents significant progress in the management of this disease.

3: The NIR fluorescence allows detection of microscopic lesions, which are not visible with current clinical imaging techniques. In addition, the fluorescence of LS838 is brighter than LS301, allowing us to use smaller amounts of the material to achieve the same uptake kinetics as LS301.

4: LS838 can be radiolabeled at a tyrosine residue for combined intravital fluorescence microscopy and noninvasive PDAC imaging. Unlike LS301, the tyrosine within LS838 allows the labeling of LS838 with radionuclides such as fluorine-18, iodine-123, I-124, I-125, and I-131. This allows the imaging of cancer in the human body noninvasively using nuclear imaging methods, and then the use of optical methods to guide tissue biopsy, surgery, and assessment of surgical margins. This combination of noninvasive and invasive methods opens new opportunity for the use of this compound. The placement of the tyrosine is important in the retention of LS838 in tumors.

5: Conjugation of chemotherapeutics to the free carboxylic acid group of LS838 will allow highly selective treatment of PDAC with minimal off-target effect on the healthy pancreatic cells.

6: LS838 selectively remains in diverse tumors without significant loss of fluorescence over time.

7: The high specificity of LS838 for cancer cells in the presence of healthy white blood cells creates a unique opportunity to use the same agent for detecting circulating tumor cells (CTCs) without resorting to additional tagging steps with multiple expensive antibodies.

What is claimed is:

1. A compound having the formula:

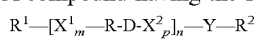

wherein:
- $R^1$ is a carbocyanine dye selected from Cypate (cypate 4), LS288, LS798, LS276, LS843, Cypate 3, and Cypate 2;
- $R^2$ is selected from a treatment agent, hydrogen, hydroxyl, $NH_2$, hydrocarbyl, and substituted hydrocarbyl; wherein the treatment agent selected from daunorubicin, adriamycin, paclitaxel, docetaxel, vinblastine, vincristine, vinorelbine, 5-fluorouracil, capecitabine, 6-mercaptopurine, methotrexate, gemcitabine, cytarabine, fludarabine, pemetrexed, cytosine arabinoside, methotrexate, aminopterin, busulfan, cisplatin, carboplatin, chlorambucil, cyclophosphamide, ifosfamide, dacarbazine, mechlorethamine, melphalan, temozolomide, carmustine, lomustine, daunorubicin, doxorubicin, epirubicin, idarubicin, mitoxantrone, topotecan, irinotecan, etoposide, teniposide, cytotoxins, macromycin, taxol, cholchicine, VEGF inhibitors, and anti-VEGF antibodies;
- $[X^1_m—R-D-X^2_p]_n—Y$ together form a linear or cyclic peptide selected from the group consisting of

| SEQ ID NO: | $[X^1_m-R-D-X^2_p]_nY$ |
|---|---|
| 8 | [$_D$Cys-Gly-Arg-Asp-Ser-Pro-Cys]-Lys-Tyr |
| 9 | [$_D$Cys-Gly-Arg-Asp-Ser-Pro-Cys]-Tyr |
| 10 | [$_D$Cys-Gly-Arg-Asp-Ser-Pro-Cys]-Tyr-Lys |
| 11 | [$_D$Cys-Gly-Arg-Asp-Ser-Pro-$_D$Cys]-Tyr |

| SEQ ID NO: | $[X^1_m\text{-}R\text{-}D\text{-}X^2_p]_n Y$ |
|---|---|
| 12 | [Cys-Gly-Arg-Asp-Ser-Pro-Cys]-Tyr |
| 17 | Gly-[$_D$Cys-Gly-Arg-Asp-Ser-Pro-Cys]-Tyr |
| 18 | Gly-[$_D$Cys-Gly-Arg-Asp-Ser-Pro-Cys]-$_D$Tyr |
| 19 | Gly-[$_D$Cys-Gly-Arg-Asp-Ser-Pro-Cys]-$_D$Tyr-Lys |
| 20 | Gly-[Cys-Gly-Arg-Asp-Ser-Pro-Cys]-$_D$Tyr-Lys |
| 21 | Gly-[$_D$Cys-Gly-Arg-Asp-Ser-Pro-$_D$Cys]-Tyr |
| 22 | Gly-[Cys-Gly-Arg-Asp-Ser-Pro-$_D$Cys]-Tyr |
| 23 | Gly-[$_D$Cys-Gly-Arg-Asp-Ser-Pro-$_D$Cys]-$_D$Tyr | and
a dash (-) represent a covalent bond.

2. The compound of claim 1, further comprising a polyethylene glycol moiety conjugated to the carbocyanine dye.

3. The compound of claim 1, wherein the Y is radiolabeled.

4. The compound of claim 3, wherein the radiolabel is fluorine or iodine radionuclide.

5. The compound of claim 1, further comprising a linker, $L^1$, that conjugates $R^1$ to $X^1$ and a linker, $L^2$, that conjugates $R^2$ to Y.

6. The compound of claim 5, wherein the linker is selected from an amino acid residue, a hydrocarbyl and a substituted hydrocarbyl.

7. A compound having formula (II):

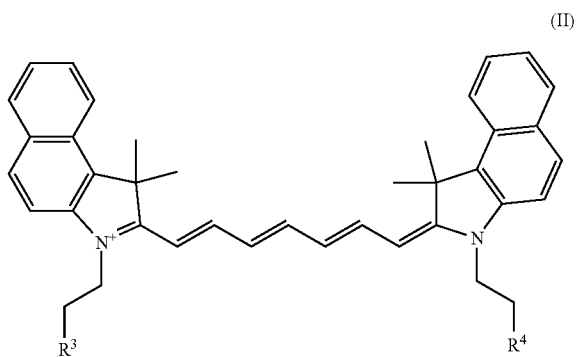

(II)

wherein:
$R^3$ is selected from daunorubicin, adriamycin, paclitaxel, docetaxel, vinblastine, vincristine, vinorelbine, 5-fluorouracil, capecitabine, 6-mercaptopurine, methotrexate, gemcitabine, cytarabine, fludarabine, pemetrexed, cytosine arabinoside, methotrexate, aminopterin, busulfan, cisplatin, carboplatin, chlorambucil, cyclophosphamide, ifosfamide, dacarbazine, mechlorethamine, melphalan, temozolomide, carmustine, lomustine, daunorubicin, doxorubicin, epirubicin, idarubicin, mitoxantrone, topotecan, irinotecan, etoposide, teniposide, cytotoxins, macromycin, taxol, cholchicine, VEGF inhibitors, and anti-VEGF antibodies; and $R^4$ is selected from the group consisting of:

| SEQ ID NO: | $R^4$ |
|---|---|
| 8 | CONH-[$_D$Cys-Gly-Arg-Asp-Ser-Pro-Cys]-Lys-Tyr-OH |
| 9 | CONH-[$_D$Cys-Gly-Arg-Asp-Ser-Pro-Cys]-Tyr-OH |
| 10 | CONH-[$_D$Cys-Gly-Arg-Asp-Ser-Pro-Cys]-Tyr-Lys-OH |
| 11 | CONH-[$_D$Cys-Gly-Arg-Asp-Ser-Pro-$_D$Cys]-Tyr-OH |
| 12 | CONH-[Cys-Gly-Arg-Asp-Ser-Pro-Cys]-Tyr-OH |
| 13 | CONH-[Cys-Arg-Gly-Asp-Ser-Pro-Cys]-Tyr-OH |
| 14 | CONH-[$_D$Cys-Arg-Gly-Asp-Ser-Pro-Cys]-Tyr-OH |
| 15 | CONH-[$_D$Cys-Arg-Gly-Asp-Ser-Pro-$_D$Cys]-Tyr-OH |
| 17 | CONH-Gly-[$_D$Cys-Gly-Arg-Asp-Ser-Pro-Cys]-Tyr-OH |
| 18 | CONH-Gly-[$_D$Cys-Gly-Arg-Asp-Ser-Pro-Cys]-$_D$Tyr-OH |
| 19 | CONH-Gly-[$_D$Cys-Gly-Arg-Asp-Ser-Pro-Cys]-$_D$Tyr-Lys-OH |
| 20 | CONH-Gly-[Cys-Gly-Arg-Asp-Ser-Pro-Cys]-$_D$Tyr-Lys-OH |
| 21 | CONH-Gly-[$_D$Cys-Gly-Arg-Asp-Ser-Pro-$_D$Cys]-Tyr-OH |
| 22 | CONH-Gly-[Cys-Gly-Arg-Asp-Ser-Pro-$_D$Cys]-Tyr-OH |
| 23 | CONH-Gly-[$_D$Cys-Gly-Arg-Asp-Ser-Pro-$_D$Cys]-$_D$Tyr-OH. |

8. The compound of claim 7, wherein $R^4$ is selected from SEQ ID NOS 18, 19, 20, 21, and 23.

9. The compound of claim 7, wherein one or more amino acid residues are inserted prior to or after the Tyr of $R^4$.

10. The compound of claim 9, wherein a Lys is inserted after the Tyr.

11. The compound of claim 7, wherein the Tyr is halogenated.

12. The compound of claim 11, wherein the halogen is a radioisotope selected from $^{18}$F, $^{75}$Br, $^{77}$Br, $^{122}$I, $^{123}$I, $^{124}$I, $^{125}$I, $^{129}$I, $^{131}$I, and $^{211}$At.

13. The compound of claim 1, wherein $[X^1_m\text{—}R\text{-}D\text{-}X^2_p]_n\text{—}Y$ is SEQ ID NO: 9.

14. The compound of claim 1, wherein $[X^1_m\text{—}R\text{-}D\text{-}X^2_p]_n\text{—}Y$ is SEQ ID NO: 11.

* * * * *

SEQUENCE LISTING

<160> NUMBER OF SEQ ID NOS: 25

<210> SEQ ID NO 1
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<400> SEQUENCE: 1

Xaa Gly Arg Asp Ser Pro Cys Lys
1               5

<210> SEQ ID NO 2
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<220> FEATURE:
<221> NAME/KEY: MISC_FEATURE
<222> LOCATION: (7)..(7)
<223> OTHER INFORMATION: Xaa=D-Cysteine
<400> SEQUENCE: 2

Xaa Gly Arg Asp Ser Pro Xaa Lys
1               5

<210> SEQ ID NO 3
<211> LENGTH: 8
<212> TYPE: PRT
<213> ORGANISM: Artificial Sequence
<220> FEATURE:
<223> OTHER INFORMATION: SYNTHESIZED
<400> SEQUENCE: 3

Cys Gly Arg Asp Ser Pro Cys Lys
1               5

<210> SEQ ID NO 4
<211> LENGTH: 8
<212> TYPE: PRT
<213> ORGANISM: Artificial Sequence
<220> FEATURE:
<223> OTHER INFORMATION: SYNTHESIZED
<400> SEQUENCE: 4

Cys Arg Gly Asp Ser Pro Cys Lys
1               5

<210> SEQ ID NO 5
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<400> SEQUENCE: 5

```
Xaa Arg Gly Asp Ser Pro Cys Lys
1               5

<210> SEQ ID NO 6
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<220> FEATURE:
<221> NAME/KEY: MISC_FEATURE
<222> LOCATION: (7)..(7)
<223> OTHER INFORMATION: Xaa=D-Cysteine

<400> SEQUENCE: 6

Xaa Arg Gly Asp Ser Pro Xaa Lys
1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa=D-Cysteine

<400> SEQUENCE: 7

Tyr Xaa Gly Arg Asp Ser Pro Cys Lys
1               5

<210> SEQ ID NO 8
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine

<400> SEQUENCE: 8

Xaa Gly Arg Asp Ser Pro Cys Lys Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine

<400> SEQUENCE: 9

Xaa Gly Arg Asp Ser Pro Cys Tyr
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine

<400> SEQUENCE: 10

Xaa Gly Arg Asp Ser Pro Cys Tyr Lys
1               5

<210> SEQ ID NO 11
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<220> FEATURE:
<221> NAME/KEY: MISC_FEATURE
<222> LOCATION: (7)..(7)
<223> OTHER INFORMATION: Xaa=D-Cysteine

<400> SEQUENCE: 11

Xaa Gly Arg Asp Ser Pro Xaa Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 12

Cys Gly Arg Asp Ser Pro Cys Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 13

Cys Arg Gly Asp Ser Pro Cys Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine

<400> SEQUENCE: 14

Xaa Arg Gly Asp Ser Pro Cys Tyr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<220> FEATURE:
<221> NAME/KEY: MISC_FEATURE
<222> LOCATION: (7)..(7)
<223> OTHER INFORMATION: Xaa=D-Cysteine

<400> SEQUENCE: 15

Xaa Arg Gly Asp Ser Pro Xaa Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (7)..(7)
<223> OTHER INFORMATION: Xaa=D-Cysteine

<400> SEQUENCE: 16

Tyr Gly Arg Asp Ser Pro Xaa Lys
1               5

<210> SEQ ID NO 17
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa=D-Cysteine

<400> SEQUENCE: 17

Gly Xaa Gly Arg Asp Ser Pro Cys Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa=D-Cysteine
<220> FEATURE:
<221> NAME/KEY: MISC_FEATURE
<222> LOCATION: (9)..(9)
<223> OTHER INFORMATION: Xaa=D-Tyrosine

<400> SEQUENCE: 18

Gly Xaa Gly Arg Asp Ser Pro Cys Xaa
1               5

<210> SEQ ID NO 19
<211> LENGTH: 10
<212> TYPE: PRT
```

```
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa=D-Cysteine
<220> FEATURE:
<221> NAME/KEY: MISC_FEATURE
<222> LOCATION: (9)..(9)
<223> OTHER INFORMATION: Xaa=D-Tyrosine

<400> SEQUENCE: 19

Gly Xaa Gly Arg Asp Ser Pro Cys Xaa Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (9)..(9)
<223> OTHER INFORMATION: Xaa=D-Tyrosine

<400> SEQUENCE: 20

Gly Cys Gly Arg Asp Ser Pro Cys Xaa Lys
1               5                   10

<210> SEQ ID NO 21
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (2)..(2)
<223> OTHER INFORMATION: Xaa=D-Cysteine
<220> FEATURE:
<221> NAME/KEY: MISC_FEATURE
<222> LOCATION: (8)..(8)
<223> OTHER INFORMATION: Xaa=D-Cysteine

<400> SEQUENCE: 21

Gly Xaa Gly Arg Asp Ser Pro Xaa Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (8)..(8)
<223> OTHER INFORMATION: Xaa=D-Cysteine

<400> SEQUENCE: 22

Gly Cys Gly Arg Asp Ser Pro Xaa Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: SYNTHESIZED
```

```
<220> FEATURE:
<221> NAME/KEY: MISC_FEATURE
<222> LOCATION: (2)..(2)
<223> OTHER INFORMATION: Xaa=D-Cysteine
<220> FEATURE:
<221> NAME/KEY: MISC_FEATURE
<222> LOCATION: (8)..(8)
<223> OTHER INFORMATION: Xaa=D-Cysteine
<220> FEATURE:
<221> NAME/KEY: MISC_FEATURE
<222> LOCATION: (9)..(9)
<223> OTHER INFORMATION: Xaa=D-Tyrosine

<400> SEQUENCE: 23

Gly Xaa Gly Arg Asp Ser Pro Xaa Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine

<400> SEQUENCE: 24

Xaa Gly Arg Asp Ser Pro Cys
1               5

<210> SEQ ID NO 25
<211> LENGTH: 7
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa=D-Cysteine
<220> FEATURE:
<221> NAME/KEY: MISC_FEATURE
<222> LOCATION: (7)..(7)
<223> OTHER INFORMATION: Xaa=D-Cysteine

<400> SEQUENCE: 25

Xaa Gly Arg Asp Ser Pro Xaa
1               5
```